(12) United States Patent
Freschauf et al.

(10) Patent No.: US 11,207,181 B2
(45) Date of Patent: *Dec. 28, 2021

(54) HEART VALVE SEALING DEVICES AND DELIVERY DEVICES THEREFOR

(71) Applicant: Edwards Lifesciences Corporation, Irvine, CA (US)

(72) Inventors: Lauren R. Freschauf, Mission Viejo, CA (US); Sergio Delgado, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 233 days.

This patent is subject to a terminal disclaimer.

(21) Appl. No.: 16/385,701

(22) Filed: Apr. 16, 2019

(65) Prior Publication Data

US 2019/0321166 A1 Oct. 24, 2019

Related U.S. Application Data

(60) Provisional application No. 62/659,253, filed on Apr. 18, 2018.

(51) Int. Cl.
*A61F 2/24* (2006.01)

(52) U.S. Cl.
CPC ............ *A61F 2/246* (2013.01); *A61F 2/2466* (2013.01)

(58) Field of Classification Search
CPC ...... A61F 2/246; A61F 2/2442; A61F 2/2466; A61F 2220/016
See application file for complete search history.

(56) References Cited

U.S. PATENT DOCUMENTS

| 3,874,388 | A | 4/1975 | King et al. |
| 4,340,091 | A | 7/1982 | Skelton et al. |
| 4,506,669 | A | 3/1985 | Blake, III |
| 4,590,937 | A | 5/1986 | Deniega |
| 4,693,248 | A | 9/1987 | Failla |
| 4,803,983 | A | 2/1989 | Siegel |
| 5,125,895 | A | 6/1992 | Buchbinder et al. |
| 5,171,252 | A | 12/1992 | Friedland |

(Continued)

FOREIGN PATENT DOCUMENTS

| CN | 1142351 A | 2/1997 |
| CN | 102395331 A | 3/2012 |

(Continued)

OTHER PUBLICATIONS

Batista RJ et al., "Partial left ventriculectomy to treat end-stage heart disease", Ann Thorac Surg., vol. 64, Issue—3, pp. 634-638, Sep. 1997.

(Continued)

*Primary Examiner* — Melanie R Tyson
(74) *Attorney, Agent, or Firm* — Thomas C. Richardson

(57) ABSTRACT

A valve repair device for repairing a native heart valve of a patient includes a pair of clasps, where each clasp is configured to attach to native valve leaflet. The ends of the pair of clasps can move away from one another to a partially open position when the native valve leaflets open during a diastolic phase of a cardiac cycle, and the ends of the pair of clasps can move toward one another when the native valve leaflets close during a systolic phase of a cardiac cycle.

13 Claims, 76 Drawing Sheets

(56) References Cited

U.S. PATENT DOCUMENTS

| | | |
|---|---|---|
| 5,195,962 A | 3/1993 | Martin et al. |
| 5,292,326 A | 3/1994 | Green et al. |
| 5,327,905 A | 7/1994 | Avitall |
| 5,363,861 A | 11/1994 | Edwards et al. |
| 5,370,685 A | 12/1994 | Stevens |
| 5,389,077 A | 2/1995 | Melinyshyn et al. |
| 5,411,552 A | 5/1995 | Andersen et al. |
| 5,450,860 A | 9/1995 | O'Connor |
| 5,456,674 A | 10/1995 | Bos et al. |
| 5,474,057 A | 12/1995 | Makower et al. |
| 5,478,353 A | 12/1995 | Yoon |
| 5,487,746 A | 1/1996 | Yu et al. |
| 5,565,004 A | 10/1996 | Christoudias |
| 5,607,462 A | 3/1997 | Imran |
| 5,609,598 A | 3/1997 | Laufer et al. |
| 5,611,794 A | 3/1997 | Sauer et al. |
| 5,626,607 A | 5/1997 | Malecki et al. |
| 5,695,504 A | 12/1997 | Gifford, III et al. |
| 5,716,417 A | 2/1998 | Girard et al. |
| 5,727,569 A | 3/1998 | Benetti et al. |
| 5,741,297 A | 4/1998 | Simon |
| 5,782,746 A | 7/1998 | Wright |
| 5,797,960 A | 8/1998 | Stevens et al. |
| 5,836,311 A | 11/1998 | Borst et al. |
| 5,843,076 A | 12/1998 | Webster, Jr. et al. |
| 5,855,590 A | 1/1999 | Malecki et al. |
| 5,885,271 A | 3/1999 | Hamilton et al. |
| 5,888,247 A | 3/1999 | Benetti |
| 5,891,017 A | 4/1999 | Swindle et al. |
| 5,891,112 A | 4/1999 | Samson |
| 5,894,843 A | 4/1999 | Benetti et al. |
| 5,921,979 A | 7/1999 | Kovac et al. |
| 5,944,738 A | 8/1999 | Amplatz et al. |
| 5,957,835 A | 9/1999 | Anderson et al. |
| 5,972,020 A | 10/1999 | Carpentier et al. |
| 5,980,534 A | 11/1999 | Gimpelson |
| 6,004,329 A | 12/1999 | Myers et al. |
| 6,010,531 A | 1/2000 | Donlon et al. |
| 6,017,358 A | 1/2000 | Yoon et al. |
| 6,086,600 A | 7/2000 | Kortenbach |
| 6,120,496 A | 9/2000 | Whayne et al. |
| 6,132,370 A | 10/2000 | Furnish et al. |
| 6,162,239 A | 12/2000 | Manhes |
| 6,165,183 A | 12/2000 | Kuehn et al. |
| 6,182,664 B1 | 2/2001 | Cosgrove |
| 6,193,732 B1 | 2/2001 | Frantzen et al. |
| 6,193,734 B1 | 2/2001 | Bolduc et al. |
| 6,200,315 B1 | 3/2001 | Gaiser et al. |
| 6,228,032 B1 | 5/2001 | Eaton et al. |
| 6,241,743 B1 | 6/2001 | Levin et al. |
| 6,269,819 B1 | 8/2001 | Oz et al. |
| 6,269,829 B1 | 8/2001 | Chen et al. |
| 6,312,447 B1 | 11/2001 | Grimes |
| 6,458,153 B1 | 10/2002 | Bailey et al. |
| 6,461,366 B1 | 10/2002 | Seguin |
| 6,468,285 B1 | 10/2002 | Hsu et al. |
| 6,508,806 B1 | 1/2003 | Hoste |
| 6,508,825 B1 | 1/2003 | Selmon et al. |
| 6,530,933 B1 | 3/2003 | Yeung et al. |
| 6,537,290 B2 | 3/2003 | Adams et al. |
| 6,544,215 B1 | 4/2003 | Bencini et al. |
| 6,626,930 B1 | 9/2003 | Mien et al. |
| 6,629,534 B1 | 10/2003 | St. Goar et al. |
| 6,695,866 B1 | 2/2004 | Kuehn et al. |
| 6,719,767 B1 | 4/2004 | Kimblad |
| 6,752,813 B2 | 6/2004 | Goldfarb et al. |
| 6,764,510 B2 | 7/2004 | Vidlund et al. |
| 6,770,083 B2 | 8/2004 | Seguin |
| 6,837,867 B2 | 1/2005 | Kortelling |
| 6,855,137 B2 | 2/2005 | Bon |
| 6,875,224 B2 | 4/2005 | Grimes |
| 6,913,614 B2 | 7/2005 | Marino et al. |
| 6,939,337 B2 | 9/2005 | Parker et al. |
| 6,945,956 B2 | 9/2005 | Waldhauser et al. |
| 7,011,669 B2 | 3/2006 | Kimblad |
| 7,048,754 B2 | 5/2006 | Martin et al. |
| 7,101,395 B2 | 9/2006 | Tremulis et al. |
| 7,112,207 B2 | 9/2006 | Allen et al. |
| 7,125,421 B2 | 10/2006 | Tremulis et al. |
| 7,226,467 B2 | 6/2007 | Lucatero et al. |
| 7,288,097 B2 | 10/2007 | Seguin |
| 7,371,210 B2 | 5/2008 | Brock et al. |
| 7,464,712 B2 | 12/2008 | Oz et al. |
| 7,509,959 B2 | 3/2009 | Oz et al. |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,604,646 B2 | 10/2009 | Goldfarb et al. |
| 7,608,091 B2 | 10/2009 | Goldfarb et al. |
| 7,635,329 B2 | 12/2009 | Goldfarb et al. |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,704,269 B2 | 4/2010 | St. Goar et al. |
| 7,731,706 B2 | 6/2010 | Potter |
| 7,736,388 B2 | 6/2010 | Goldfarb et al. |
| 7,744,609 B2 | 6/2010 | Allen et al. |
| 7,748,389 B2 | 7/2010 | Salahieh et al. |
| 7,753,923 B2 | 7/2010 | St. Goar et al. |
| 7,753,932 B2 | 7/2010 | Gingrich et al. |
| 7,758,596 B2 | 7/2010 | Oz et al. |
| 7,780,723 B2 | 8/2010 | Taylor |
| 7,803,185 B2 | 9/2010 | Gabbay |
| 7,811,296 B2 | 10/2010 | Goldfarb et al. |
| 7,824,443 B2 | 11/2010 | Salahieh et al. |
| 7,981,123 B2 | 7/2011 | Seguin |
| 7,988,724 B2 | 8/2011 | Salahieh et al. |
| 7,998,151 B2 | 8/2011 | Goar et al. |
| 8,029,518 B2 | 10/2011 | Goldfarb et al. |
| 8,052,592 B2 | 11/2011 | Goldfarb et al. |
| 8,052,749 B2 | 11/2011 | Salahieh et al. |
| 8,052,750 B2 | 11/2011 | Tuval et al. |
| 8,057,493 B2 | 11/2011 | Goldfarb et al. |
| 8,070,805 B2 | 12/2011 | Vidlund et al. |
| 8,096,985 B2 | 1/2012 | Legaspi et al. |
| 8,104,149 B1 | 1/2012 | McGarity |
| 8,123,703 B2 | 2/2012 | Martin et al. |
| 8,133,239 B2 | 3/2012 | Oz et al. |
| 8,147,542 B2 | 4/2012 | Maisano et al. |
| 8,172,856 B2 | 5/2012 | Eigler et al. |
| 8,187,299 B2 | 5/2012 | Goldfarb et al. |
| 8,206,437 B2 | 6/2012 | Bonhoeffer et al. |
| 8,216,256 B2 | 7/2012 | Raschdorf, Jr. et al. |
| 8,216,301 B2 | 7/2012 | Bonhoeffer et al. |
| 8,303,608 B2 | 11/2012 | Goldfarb et al. |
| 8,303,653 B2 | 11/2012 | Bonhoeffer et al. |
| 8,313,525 B2 | 11/2012 | Tuval et al. |
| 8,323,334 B2 | 12/2012 | Deem et al. |
| 8,343,174 B2 | 1/2013 | Goldfarb et al. |
| 8,348,995 B2 | 1/2013 | Tuval et al. |
| 8,348,996 B2 | 1/2013 | Tuval et al. |
| 8,409,273 B2 | 4/2013 | Thornton et al. |
| 8,414,643 B2 | 4/2013 | Tuval et al. |
| 8,425,404 B2 | 4/2013 | Wilson et al. |
| 8,449,599 B2 | 5/2013 | Chau et al. |
| 8,449,606 B2 | 5/2013 | Eliasen et al. |
| 8,460,368 B2 | 6/2013 | Taylor et al. |
| 8,470,028 B2 | 6/2013 | Thornton et al. |
| 8,480,730 B2 | 7/2013 | Maurer et al. |
| 8,500,761 B2 | 8/2013 | Goldfarb et al. |
| 8,540,767 B2 | 9/2013 | Zhang |
| 8,579,965 B2 | 11/2013 | Bonhoeffer et al. |
| 8,585,756 B2 | 11/2013 | Bonhoeffer et al. |
| 8,652,202 B2 | 2/2014 | Alon et al. |
| 8,668,733 B2 | 3/2014 | Haug et al. |
| 8,721,665 B2 | 5/2014 | Oz et al. |
| 8,734,505 B2 | 5/2014 | Goldfarb et al. |
| 8,740,918 B2 | 6/2014 | Seguin |
| 8,740,920 B2 | 6/2014 | Goldfarb et al. |
| 8,747,460 B2 | 6/2014 | Tuval et al. |
| 8,764,774 B2 | 7/2014 | Sigmon, Jr. |
| 8,771,345 B2 | 7/2014 | Tuval et al. |
| 8,771,346 B2 | 7/2014 | Tuval et al. |

(56) References Cited

U.S. PATENT DOCUMENTS

| | | |
|---|---|---|
| 8,771,347 B2 | 7/2014 | DeBoer et al. |
| 8,778,017 B2 | 7/2014 | Eliasen et al. |
| 8,834,564 B2 | 9/2014 | Tuval et al. |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,926,691 B2 | 1/2015 | Chau et al. |
| 8,945,177 B2 | 2/2015 | Dell et al. |
| 9,011,468 B2 | 4/2015 | Ketai et al. |
| 9,034,032 B2 | 5/2015 | McLean et al. |
| 9,044,246 B2 | 6/2015 | Goldfarb et al. |
| 9,138,312 B2 | 9/2015 | Tuval et al. |
| 9,198,757 B2 | 12/2015 | Schroeder et al. |
| 9,220,507 B1 | 12/2015 | Patel et al. |
| 9,259,317 B2 | 2/2016 | Wilson et al. |
| 9,282,972 B1 | 3/2016 | Patel et al. |
| 9,301,834 B2 | 4/2016 | Tuval et al. |
| 9,308,360 B2 | 4/2016 | Bishop et al. |
| 9,387,071 B2 | 7/2016 | Tuval et al. |
| 9,414,918 B2 | 8/2016 | Chau et al. |
| 9,427,237 B2 | 8/2016 | Oz et al. |
| 9,427,327 B2 | 8/2016 | Parrish |
| 9,439,763 B2 | 9/2016 | Geist et al. |
| 9,510,829 B2 | 12/2016 | Goldfarb et al. |
| 9,510,837 B2 | 12/2016 | Seguin |
| 9,510,946 B2 | 12/2016 | Chau et al. |
| 9,572,660 B2 | 2/2017 | Braido et al. |
| 9,642,704 B2 | 5/2017 | Tuval et al. |
| 9,700,445 B2 | 7/2017 | Martin et al. |
| 9,775,963 B2 | 10/2017 | Miller |
| D809,139 S | 1/2018 | Marsot et al. |
| 9,889,002 B2 | 2/2018 | Bonhoeffer et al. |
| 9,949,824 B2 | 4/2018 | Bonhoeffer et al. |
| 10,076,327 B2 | 9/2018 | Ellis et al. |
| 10,076,415 B1 | 9/2018 | Metchik et al. |
| 10,099,050 B2 | 10/2018 | Chen et al. |
| 10,105,221 B2 | 10/2018 | Siegel |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,188,392 B2 | 1/2019 | Wei |
| 10,226,309 B2 | 3/2019 | Ho et al. |
| 10,231,837 B1 | 3/2019 | Metchik et al. |
| 10,238,493 B1 | 3/2019 | Metchik et al. |
| 10,238,494 B2 | 3/2019 | McNiven et al. |
| 10,238,495 B2 | 3/2019 | Marsot et al. |
| 10,299,924 B2 | 5/2019 | Kizuka |
| 10,376,673 B2 | 8/2019 | Van Hoven et al. |
| 10,575,841 B1 | 3/2020 | Paulos |
| 2001/0005787 A1 | 6/2001 | Oz et al. |
| 2002/0013571 A1 | 1/2002 | Goldfarb et al. |
| 2002/0107531 A1 | 8/2002 | Schreck et al. |
| 2002/0173811 A1 | 11/2002 | Tu et al. |
| 2002/0183787 A1 | 12/2002 | Wahr et al. |
| 2003/0144573 A1 | 7/2003 | Heilman et al. |
| 2003/0187467 A1 | 10/2003 | Schreck |
| 2003/0208231 A1 | 11/2003 | Williamson et al. |
| 2004/0003819 A1 | 1/2004 | St. Goar et al. |
| 2004/0030382 A1 | 2/2004 | St. Goar et al. |
| 2004/0034365 A1 | 2/2004 | Lentz et al. |
| 2004/0039442 A1 | 2/2004 | St. Goar et al. |
| 2004/0044350 A1 | 3/2004 | Martin et al. |
| 2004/0044365 A1 | 3/2004 | Bachman |
| 2004/0049207 A1* | 3/2004 | Goldfarb ........... A61F 2/246 606/139 |
| 2004/0122448 A1 | 6/2004 | Levine |
| 2004/0127981 A1 | 7/2004 | Rahdert et al. |
| 2004/0127982 A1 | 7/2004 | Machold et al. |
| 2004/0147943 A1 | 7/2004 | Kobayashi |
| 2004/0167539 A1 | 8/2004 | Kuehn et al. |
| 2004/0181206 A1 | 9/2004 | Chiu et al. |
| 2004/0181238 A1 | 9/2004 | Zarbatany et al. |
| 2004/0210307 A1 | 10/2004 | Khairkhahan |
| 2004/0220593 A1 | 11/2004 | Greenhalgh |
| 2005/0010287 A1 | 1/2005 | Macoviak et al. |
| 2005/0033446 A1 | 2/2005 | Deem et al. |
| 2005/0049618 A1 | 3/2005 | Masuda et al. |
| 2005/0070926 A1 | 3/2005 | Ortiz |
| 2005/0137690 A1 | 6/2005 | Salahieh et al. |
| 2005/0143767 A1 | 6/2005 | Kimura et al. |
| 2005/0165429 A1 | 7/2005 | Douglas et al. |
| 2005/0216039 A1 | 9/2005 | Lederman |
| 2005/0251183 A1 | 11/2005 | Buckman et al. |
| 2005/0288786 A1 | 12/2005 | Chanduszko |
| 2006/0020275 A1 | 1/2006 | Goldfarb et al. |
| 2006/0089671 A1 | 4/2006 | Goldfarb et al. |
| 2006/0100649 A1 | 5/2006 | Hart |
| 2006/0122647 A1 | 6/2006 | Callaghan et al. |
| 2006/0142694 A1 | 6/2006 | Bednarek et al. |
| 2006/0178700 A1 | 8/2006 | Quinn |
| 2006/0224169 A1 | 10/2006 | Weisenburgh et al. |
| 2006/0229708 A1* | 10/2006 | Powell .................. A61F 2/2478 623/1.24 |
| 2007/0010800 A1 | 1/2007 | Weitzner et al. |
| 2007/0010877 A1 | 1/2007 | Salahieh et al. |
| 2007/0016286 A1 | 1/2007 | Herrmann et al. |
| 2007/0021779 A1 | 1/2007 | Garvin et al. |
| 2007/0032807 A1 | 2/2007 | Ortiz et al. |
| 2007/0038293 A1 | 2/2007 | St.Goar et al. |
| 2007/0093857 A1 | 4/2007 | Rogers et al. |
| 2007/0093890 A1 | 4/2007 | Eliasen et al. |
| 2007/0100356 A1 | 5/2007 | Lucatero et al. |
| 2007/0129737 A1 | 6/2007 | Goldfarb et al. |
| 2007/0156197 A1 | 7/2007 | Root et al. |
| 2007/0191154 A1 | 8/2007 | Genereux et al. |
| 2007/0197858 A1 | 8/2007 | Goldfarb et al. |
| 2007/0198038 A1 | 8/2007 | Cohen et al. |
| 2007/0265700 A1 | 11/2007 | Eliasen et al. |
| 2007/0282414 A1 | 12/2007 | Soltis et al. |
| 2007/0293943 A1 | 12/2007 | Quinn |
| 2007/0299387 A1 | 12/2007 | Williams et al. |
| 2007/0299424 A1 | 12/2007 | Cumming et al. |
| 2008/0039743 A1 | 2/2008 | Fox et al. |
| 2008/0039953 A1 | 2/2008 | Davis et al. |
| 2008/0065149 A1 | 3/2008 | Thielen et al. |
| 2008/0077144 A1 | 3/2008 | Crofford |
| 2008/0091169 A1 | 4/2008 | Heideman et al. |
| 2008/0140089 A1 | 6/2008 | Kogiso et al. |
| 2008/0147093 A1 | 6/2008 | Roskopf et al. |
| 2008/0147112 A1 | 6/2008 | Sheets et al. |
| 2008/0149685 A1 | 6/2008 | Smith et al. |
| 2008/0167713 A1 | 7/2008 | Bolling |
| 2008/0167714 A1 | 7/2008 | St. Goar et al. |
| 2008/0177300 A1 | 7/2008 | Mas et al. |
| 2008/0208332 A1 | 8/2008 | Lamphere et al. |
| 2008/0221672 A1 | 9/2008 | Lamphere et al. |
| 2008/0255427 A1 | 10/2008 | Satake et al. |
| 2008/0281411 A1 | 11/2008 | Berreklouw |
| 2008/0287862 A1 | 11/2008 | Weitzner et al. |
| 2008/0294247 A1 | 11/2008 | Yang et al. |
| 2008/0312506 A1 | 12/2008 | Spivey et al. |
| 2008/0319455 A1 | 12/2008 | Harris et al. |
| 2009/0005863 A1 | 1/2009 | Goetz et al. |
| 2009/0024110 A1 | 1/2009 | Heideman et al. |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. et al. |
| 2009/0166913 A1 | 7/2009 | Guo et al. |
| 2009/0177266 A1 | 7/2009 | Powell et al. |
| 2009/0275902 A1 | 11/2009 | Heeps et al. |
| 2009/0287304 A1 | 11/2009 | Dahlgren et al. |
| 2010/0022823 A1 | 1/2010 | Goldfarb et al. |
| 2010/0057192 A1 | 3/2010 | Celermajer |
| 2010/0094317 A1 | 4/2010 | Goldfarb et al. |
| 2010/0106141 A1 | 4/2010 | Osypka et al. |
| 2010/0121433 A1 | 5/2010 | Bolling et al. |
| 2010/0121434 A1 | 5/2010 | Pau et al. |
| 2010/0217283 A1 | 8/2010 | St. Goar et al. |
| 2010/0249497 A1 | 9/2010 | Peine et al. |
| 2010/0298929 A1 | 11/2010 | Thornton et al. |
| 2010/0324595 A1 | 12/2010 | Linder et al. |

(56) References Cited

U.S. PATENT DOCUMENTS

| | | |
|---|---|---|
| 2011/0082538 A1 | 4/2011 | Dahlgren et al. |
| 2011/0137410 A1 | 6/2011 | Hacohen |
| 2011/0245855 A1 | 10/2011 | Matsuoka et al. |
| 2011/0257723 A1 | 10/2011 | McNamara |
| 2011/0295281 A1 | 12/2011 | Mizumoto et al. |
| 2012/0010461 A1 | 1/2012 | Goldfarb et al. |
| 2012/0022633 A1 | 1/2012 | Olson et al. |
| 2012/0046741 A1 | 2/2012 | Tuval et al. |
| 2012/0089125 A1 | 4/2012 | Scheibe et al. |
| 2012/0109160 A1 | 5/2012 | Martinez et al. |
| 2012/0116419 A1 | 5/2012 | Sigmon, Jr. |
| 2012/0209318 A1 | 8/2012 | Qadeer |
| 2012/0277853 A1 | 11/2012 | Rothstein |
| 2013/0035759 A1 | 2/2013 | Gross et al. |
| 2013/0041314 A1 | 2/2013 | Dillon |
| 2013/0066341 A1 | 3/2013 | Ketai et al. |
| 2013/0066342 A1 | 3/2013 | Dell et al. |
| 2013/0072945 A1 | 3/2013 | Terada |
| 2013/0073034 A1 | 3/2013 | Wilson et al. |
| 2013/0110254 A1 | 5/2013 | Osborne |
| 2013/0190798 A1 | 7/2013 | Kapadia |
| 2013/0190861 A1 | 7/2013 | Chau et al. |
| 2013/0268069 A1 | 10/2013 | Zakai et al. |
| 2013/0282059 A1 | 10/2013 | Ketai et al. |
| 2013/0304197 A1 | 11/2013 | Buchbinder et al. |
| 2013/0325110 A1 | 12/2013 | Khalil et al. |
| 2014/0031928 A1 | 1/2014 | Murphy et al. |
| 2014/0046433 A1 | 2/2014 | Kovalsky |
| 2014/0046434 A1 | 2/2014 | Rolando et al. |
| 2014/0052237 A1 | 2/2014 | Lane et al. |
| 2014/0058411 A1 | 2/2014 | Soutorine et al. |
| 2014/0066693 A1 | 3/2014 | Goldfarb et al. |
| 2014/0067048 A1 | 3/2014 | Chau et al. |
| 2014/0067052 A1 | 3/2014 | Chau et al. |
| 2014/0094903 A1 | 4/2014 | Miller et al. |
| 2014/0135685 A1 | 5/2014 | Kabe et al. |
| 2014/0194975 A1 | 7/2014 | Quill et al. |
| 2014/0200662 A1 | 7/2014 | Eftel et al. |
| 2014/0207231 A1 | 7/2014 | Hacohen et al. |
| 2014/0236198 A1 | 8/2014 | Goldfarb et al. |
| 2014/0243968 A1 | 8/2014 | Padala |
| 2014/0251042 A1 | 9/2014 | Asselin et al. |
| 2014/0277404 A1 | 9/2014 | Wilson et al. |
| 2014/0277411 A1 | 9/2014 | Bortlein et al. |
| 2014/0277427 A1 | 9/2014 | Ratz et al. |
| 2014/0316428 A1 | 10/2014 | Golan |
| 2014/0324164 A1 | 10/2014 | Gross et al. |
| 2014/0330368 A1 | 11/2014 | Gloss et al. |
| 2014/0336751 A1 | 11/2014 | Kramer |
| 2014/0371843 A1 | 12/2014 | Wilson et al. |
| 2015/0039084 A1 | 2/2015 | Levi et al. |
| 2015/0057704 A1 | 2/2015 | Takahashi |
| 2015/0094802 A1 | 4/2015 | Buchbinder et al. |
| 2015/0100116 A1 | 4/2015 | Mohl et al. |
| 2015/0105804 A1 | 4/2015 | Dell et al. |
| 2015/0105808 A1 | 4/2015 | Gordon et al. |
| 2015/0148896 A1 | 5/2015 | Karapetian et al. |
| 2015/0157268 A1 | 6/2015 | Winshtein et al. |
| 2015/0182223 A1 | 7/2015 | Ketai et al. |
| 2015/0196390 A1 | 7/2015 | Ma et al. |
| 2015/0223793 A1 | 8/2015 | Goldfarb et al. |
| 2015/0230919 A1 | 8/2015 | Chau et al. |
| 2015/0238313 A1 | 8/2015 | Spence et al. |
| 2015/0257757 A1 | 9/2015 | Powers et al. |
| 2015/0257877 A1 | 9/2015 | Hernandez |
| 2015/0257883 A1 | 9/2015 | Basude et al. |
| 2015/0313592 A1 | 11/2015 | Coillard-Lavirotte et al. |
| 2015/0351904 A1 | 12/2015 | Cooper et al. |
| 2015/0366666 A1 | 12/2015 | Khairkhahan et al. |
| 2016/0008131 A1 | 1/2016 | Christianson et al. |
| 2016/0022970 A1 | 1/2016 | Forcucci et al. |
| 2016/0051796 A1 | 2/2016 | Kanemasa et al. |
| 2016/0106539 A1 | 4/2016 | Buchbinder et al. |
| 2016/0113762 A1 | 4/2016 | Clague et al. |
| 2016/0113764 A1 | 4/2016 | Sheahan et al. |
| 2016/0113766 A1 | 4/2016 | Ganesan et al. |
| 2016/0155987 A1 | 6/2016 | Yoo et al. |
| 2016/0174979 A1* | 6/2016 | Wei .................. A61B 17/08 606/151 |
| 2016/0174981 A1 | 6/2016 | Fago et al. |
| 2016/0242906 A1 | 8/2016 | Morriss et al. |
| 2016/0287387 A1 | 10/2016 | Wei |
| 2016/0317290 A1 | 11/2016 | Chau et al. |
| 2016/0324634 A1 | 11/2016 | Gabbay |
| 2016/0331523 A1 | 11/2016 | Chau et al. |
| 2016/0354082 A1 | 12/2016 | Oz et al. |
| 2017/0020521 A1 | 1/2017 | Krone et al. |
| 2017/0035561 A1 | 2/2017 | Rowe et al. |
| 2017/0035566 A1 | 2/2017 | Krone et al. |
| 2017/0042456 A1 | 2/2017 | Budiman |
| 2017/0042678 A1 | 2/2017 | Ganesan et al. |
| 2017/0049455 A1 | 2/2017 | Seguin |
| 2017/0100236 A1 | 4/2017 | Robertson et al. |
| 2017/0239048 A1 | 8/2017 | Goldfarb et al. |
| 2017/0252154 A1 | 9/2017 | Tubisheviiz et al. |
| 2017/0281330 A1 | 10/2017 | Liljegren et al. |
| 2017/0348102 A1 | 12/2017 | Cousins et al. |
| 2018/0000582 A1 | 1/2018 | Tuval et al. |
| 2018/0008311 A1 | 1/2018 | Shiroff et al. |
| 2018/0021044 A1 | 1/2018 | Miller et al. |
| 2018/0021129 A1 | 1/2018 | Peterson et al. |
| 2018/0021134 A1 | 1/2018 | McNiven et al. |
| 2018/0078271 A1 | 3/2018 | Thrasher, III |
| 2018/0126124 A1 | 5/2018 | Winston et al. |
| 2018/0146964 A1 | 5/2018 | Garcia et al. |
| 2018/0146966 A1 | 5/2018 | Hernandez et al. |
| 2018/0153552 A1 | 6/2018 | King et al. |
| 2018/0161159 A1 | 6/2018 | Lee et al. |
| 2018/0168803 A1 | 6/2018 | Pesce et al. |
| 2018/0221147 A1 | 8/2018 | Ganesan et al. |
| 2018/0235657 A1 | 8/2018 | Abunassar |
| 2018/0243086 A1 | 8/2018 | Barbarino et al. |
| 2018/0253665 A1 | 9/2018 | Reddy et al. |
| 2018/0263767 A1 | 9/2018 | Chau et al. |
| 2018/0296326 A1 | 10/2018 | Dixon et al. |
| 2018/0296327 A1 | 10/2018 | Dixon et al. |
| 2018/0296328 A1 | 10/2018 | Dixon et al. |
| 2018/0296329 A1 | 10/2018 | Dixon et al. |
| 2018/0296330 A1 | 10/2018 | Dixon et al. |
| 2018/0296331 A1 | 10/2018 | Dixon et al. |
| 2018/0296332 A1 | 10/2018 | Dixon et al. |
| 2018/0296333 A1 | 10/2018 | Dixon et al. |
| 2018/0296334 A1 | 10/2018 | Dixon et al. |
| 2018/0325661 A1 | 11/2018 | Delgado et al. |
| 2018/0325671 A1 | 11/2018 | Abunassar et al. |
| 2018/0333259 A1 | 11/2018 | Dibie |
| 2018/0344457 A1 | 12/2018 | Gross et al. |
| 2018/0353181 A1 | 12/2018 | Wei |
| 2019/0000613 A1 | 1/2019 | Delgado et al. |
| 2019/0000623 A1 | 1/2019 | Pan et al. |
| 2019/0008638 A1 | 1/2019 | Siegel et al. |
| 2019/0008642 A1 | 1/2019 | Delgado et al. |
| 2019/0008643 A1 | 1/2019 | Delgado et al. |
| 2019/0015199 A1 | 1/2019 | Delgado et al. |
| 2019/0015200 A1 | 1/2019 | Delgado et al. |
| 2019/0015207 A1 | 1/2019 | Delgado et al. |
| 2019/0015208 A1 | 1/2019 | Delgado et al. |
| 2019/0021851 A1 | 1/2019 | Delgado et al. |
| 2019/0021852 A1 | 1/2019 | Delgado et al. |
| 2019/0029498 A1 | 1/2019 | Mankowski et al. |
| 2019/0029810 A1 | 1/2019 | Delgado et al. |
| 2019/0029813 A1 | 1/2019 | Delgado et al. |
| 2019/0030285 A1 | 1/2019 | Prabhu et al. |
| 2019/0053803 A1 | 2/2019 | Ketai et al. |
| 2019/0053810 A1 | 2/2019 | Griffin |
| 2019/0060058 A1 | 2/2019 | Delgado et al. |
| 2019/0060059 A1 | 2/2019 | Delgado et al. |
| 2019/0060072 A1 | 2/2019 | Zeng |
| 2019/0060073 A1 | 2/2019 | Delgado et al. |
| 2019/0060074 A1 | 2/2019 | Delgado et al. |
| 2019/0060075 A1 | 2/2019 | Delgado et al. |
| 2019/0069991 A1 | 3/2019 | Metchik et al. |
| 2019/0069992 A1 | 3/2019 | Delgado et al. |
| 2019/0069993 A1 | 3/2019 | Delgado et al. |

(56) References Cited

U.S. PATENT DOCUMENTS

| | | |
|---|---|---|
| 2019/0105156 A1 | 4/2019 | He et al. |
| 2019/0111239 A1 | 4/2019 | Bolduc et al. |
| 2019/0142589 A1 | 5/2019 | Basude |
| 2019/0159782 A1 | 5/2019 | Kamaraj et al. |
| 2019/0167197 A1 | 6/2019 | Abunassar et al. |
| 2019/0209323 A1 | 7/2019 | Metchik et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0314155 A1 | 10/2019 | Franklin et al. |
| 2020/0113683 A1 | 4/2020 | Dale et al. |
| 2020/0237512 A1 | 7/2020 | McCann et al. |
| 2020/0337842 A1 | 10/2020 | Metchik et al. |
| 2021/0186698 A1 | 6/2021 | Abunassar et al. |

FOREIGN PATENT DOCUMENTS

| | | |
|---|---|---|
| EP | 0098100 A2 | 1/1984 |
| EP | 0879069 B1 | 8/2003 |
| EP | 1281375 A3 | 12/2003 |
| EP | 1301235 B1 | 10/2004 |
| EP | 1583577 B1 | 5/2007 |
| EP | 1408850 B1 | 9/2009 |
| EP | 0930845 B1 | 10/2009 |
| EP | 1624810 B1 | 3/2011 |
| EP | 1804686 B1 | 9/2015 |
| EP | 2428169 B1 | 10/2016 |
| EP | 2266503 B1 | 1/2017 |
| EP | 2266504 B1 | 3/2017 |
| FR | 2146050 A5 | 2/1973 |
| FR | 2 768 324 A1 | 3/1999 |
| JP | 2014000417 A | 1/2014 |
| WO | 9802103 A1 | 1/1998 |
| WO | 9900059 A1 | 1/1999 |
| WO | 9913777 A1 | 3/1999 |
| WO | 0060995 A3 | 4/2001 |
| WO | 03001893 A2 | 1/2003 |
| WO | 2004103162 A2 | 12/2004 |
| WO | 2004103434 A2 | 12/2004 |
| WO | 2005112792 A2 | 12/2005 |
| WO | 2006086434 A1 | 8/2006 |
| WO | 2006116558 A2 | 11/2006 |
| WO | 2006138173 A3 | 3/2007 |
| WO | 2006047709 A3 | 7/2007 |
| WO | 2008147964 A1 | 12/2008 |
| WO | 2008150529 A1 | 12/2008 |
| WO | 2009024859 A3 | 5/2009 |
| WO | 2009108942 A1 | 9/2009 |
| WO | 2009053952 A3 | 12/2009 |
| WO | 2009116041 A3 | 3/2010 |
| WO | 2010098804 A1 | 9/2010 |
| WO | 2010128502 A1 | 11/2010 |
| WO | 2011034628 A1 | 3/2011 |
| WO | 2013059747 A1 | 4/2013 |
| WO | 2016110760 A1 | 7/2016 |
| WO | 2017015632 A1 | 1/2017 |
| WO | 2018013856 A1 | 1/2018 |
| WO | 2018050200 A1 | 3/2018 |
| WO | 2018050203 A1 | 3/2018 |
| WO | 2018195015 A1 | 10/2018 |
| WO | 2018195201 A1 | 10/2018 |
| WO | 2018195215 A2 | 10/2018 |
| WO | 2019139904 A1 | 7/2019 |
| WO | 2020106705 A1 | 5/2020 |
| WO | 2020106827 A1 | 5/2020 |
| WO | 2020112622 A1 | 6/2020 |
| WO | 2020167677 A1 | 8/2020 |
| WO | 2020168081 A1 | 8/2020 |
| WO | 2020172224 A1 | 8/2020 |
| WO | 2020176410 A1 | 9/2020 |

OTHER PUBLICATIONS

Beall AC Jr. et al.,"Clinical experience with a dacron velour-covered teflon-disc mitral-valve prosthesis", Ann Thorac Surg., vol. 5, issue 5, pp. 402-410, May 1968.

Fucci et al., "Improved results with mitral valve repair using new surgical techniques", Eur J Cardiothorac Surg. 1995;Issue 9, vol. 11, pp. 621-626.

Maisano F et al., 'The edge-to-edge technique: a simplified method to correct mitral insufficiency', Eur J Cardiothorac Surg., vol. 13, Issue—3, pp. 240-245, Mar. 1998.

Reul RM et al., "Mitral valve reconstruction for mitral insufficiency", Prog Cardiovasc Dis., vol. 39, Issue—6, May-Jun. 1997.

Umaña JP et al., Bow-tie' mitral valve repair: an adjuvant technique for ischemic mitral regurgitation', Ann Thorac Surg., vol. 66, Issue—6, pp. 1640-1646, Nov. 1998.

Al-Khaja et al., "Eleven Years' Experience with Carpentier-Edwards Biological Valves in Relation to Survival and Complications", European Journal of Cardio-thoracic Surgery 3: pp. 305-311,1989.

Almagor et al., "Balloon Expandable Stent Implantation in Stenotic Right Heart Valved Conduits", Journal of the American College of Cardiology, vol. 16, No. 6, pp. 1310-1314, Nov. 15, 1990.

Al Zaibag et al., "Percutaneous Balloon Valvotomy in Tricuspid Stenosis", British Heart Journal, vol. 57, No. 1, Jan. 1987.

Andersen, H.R. "History of Percutaneous Aortic Valve Prosthesis," Herz No. 34. pp 343-346. 2009.

Andersen, et al., "Transluminal implantation of artificial heart valves. Description of a new expandable aortic valve and initial results with implantation by catheter technique in closed chest pigs." European Heart Journal (1992), 13, 704-708.

Benchimol et al., "Simultaneous Left Ventricular Echocardiography and Aortic Blood Velocity During Rapid Right Ventricular Pacing in Man", The American Journal of the Medical Sciences, vol. 273, No. 1, pp. 55-62, 1977.

Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.

Dotter et al., "Transluminal Treatment of Arteriosclerotic Obstruction: Description of a New Technic and a Preliminary Report of Its Application", Circulation, vol. XXX, pp. 654-670, 1964.

Kolata, Gina "Device that Opens Clogged Arteries Gets a Failing Grade in a New Study", The New York Times, http://www.nytimes.com/1991/01/03/health/device-that-opens-clogged-arteries-gets-a-faili . . . , pp. 1-2, wrriten January 3, 199, web page access Jul. 29, 2009.

Inoune, M.D., Kanji, et al., "Clinical Application of Transvenous Mitral Commissurotomy by a New Balloon Catheter," The Journal of Thoracic and Cardiovascular Surgery 87:394-402, 1984.

Lawrence, Jr., et al., "Percutaneous Endovascular Graft: Experimental Evaluation", Cardiovascular Radiology 163, pp. 357-360, May 1987.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Praz et al., "Compassionate use of the PASCAL transcatheter mitral valve repair system for patients with severe mitral regurgitation: a multicentre, prospective, observational, first-in-man study," Lancet vol. 390, pp. 773-780, 2017.

Porstmann et al., "Der Verschluß des Ductus Arteriosus Persistens Ohne Thorakotomie", Thoraxchirurgie Vaskuläre Chirurgie, Band 15, Heft 2, Stuttgart, im Apr. 1967, pp. 199-203.

Rashkind et al., "Creation of an Atrial Septal Defect Without Thoracotomy: A Pallative Approach to Complete Transposition of the Great Arteries", The Journal of the American Medical Association, vol. 196, No. 11, pp. 173-174, Jun. 13, 1956.

Rashkind et al., "Historical Aspects of Interventional Cardiology: Past, Present, and Future", Texas Heart Institute Journal, Interventional Cardiology, pp. 363-367.

Rosch, M.D., Josef, "The Birth, Early Years and Future of Interventional Radiology," J Vasc Interv Radiol 2003; 14:841-853.

(56) References Cited

OTHER PUBLICATIONS

Ross, D.N, "Aortic Valve Surgery", Surgery of the Aortic Valves, Guy's Hospital, London, pp. 192-197.
Sabbah et al., "Mechanical Factors in the Degeneration of Porcine Bioprosthetic Valves: An Overview", Journal of Cardiac Surgery, vol. 4, No. 4, pp. 302-309, Dec. 1989.
Selby et al., "Experience with New Retrieval Forceps for Foreign Body Removal in the Vascular, Urinary, and Biliary Systems", Radiology: 176. pp. 535-538, 1990.
Serruys et al., "Stenting of Coronary Arteries. Are we the Sorcerer's Apprentice?", European Heart Journal, 10, 774-782, pp. 37-45, 1989.
Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.
Uchida et al., "Modifications of Giantuico Expandable Wire Stents", Technical Note, American Roentgen Ray Society, pp. 1185-1187, May 1988.
Urban, Philip MD, "Coronary Artery Stenting", Editions Medecine et Hygiene, Geneve, pp. 1-47, 1991.
Watt et al., "Intravenous Adenosine in the Treatment of Supraventricular Tachycardia: A Dose-Ranging Study and Interaction with Dipyridamole", Br. J. Clin. Pharmac. 21, pp. 227-230, 1986.
Wheatley, David J., "Valve Prosthesis", Rob & Smith's Operative Surgery, pp. 415-424, 1986.

\* cited by examiner

HEART VALVE SEALING DEVICES AND DELIVERY DEVICES THEREFOR

CROSS-REFERENCE TO RELATED APPLICATIONS

The present application claims the benefit of U.S. provisional patent application Ser. No. 62/659,253, filed on Apr. 18, 2018, incorporated herein by reference in its entirety.

FIELD OF THE INVENTION

The present application relates generally to prosthetic devices and related methods for helping to seal native heart valves and prevent or reduce regurgitation therethrough, as well as devices for helping to seal native heart valves while maintaining leaflet mobility and effective orifice area of the native valve after implantation of a device.

BACKGROUND OF THE INVENTION

The native heart valves (i.e., the aortic, pulmonary, tricuspid, and mitral valves) serve critical functions in assuring the forward flow of an adequate supply of blood through the cardiovascular system. These heart valves can be damaged, and thus rendered less effective, by congenital malformations, inflammatory processes, infectious conditions, or disease. Such damage to the valves can result in serious cardiovascular compromise or death. For many years the definitive treatment for such damaged valves was surgical repair or replacement of the valve during open heart surgery. However, open heart surgeries are highly invasive and are prone to many complications. Therefore, elderly and frail patients with defective heart valves often went untreated. More recently, transvascular techniques have been developed for introducing and implanting prosthetic devices in a manner that is much less invasive than open heart surgery. One particular transvascular technique that is used for accessing the native mitral and aortic valves is the transseptal technique. The transseptal technique comprises inserting a catheter into the right femoral vein, up the inferior vena cava and into the right atrium. The septum is then punctured and the catheter passed into the left atrium.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle. The mitral valve has a very different anatomy than other native heart valves. The mitral valve includes an annulus portion, which is an annular portion of the native valve tissue surrounding the mitral valve orifice, and a pair of cusps, or leaflets, extending downward from the annulus into the left ventricle. The mitral valve annulus can form a "D"-shaped, oval, or otherwise out-of-round cross-sectional shape having major and minor axes. The anterior leaflet can be larger than the posterior leaflet, forming a generally "C"-shaped boundary between the abutting sides of the leaflets when they are closed together.

When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates (also referred to as "ventricular diastole" or "diastole"), the oxygenated blood that is collected in the left atrium flows into the left ventricle. When the muscles of the left atrium relax and the muscles of the left ventricle contract (also referred to as "ventricular systole" or "systole"), the increased blood pressure in the left ventricle urges the sides of the two leaflets together, thereby closing the one-way mitral valve so that blood cannot flow back to the left atrium and is instead expelled out of the left ventricle through the aortic valve. To prevent the two leaflets from prolapsing under pressure and folding back through the mitral annulus toward the left atrium, a plurality of fibrous cords called chordae tendineae tether the leaflets to papillary muscles in the left ventricle.

Mitral regurgitation occurs when the native mitral valve fails to close properly and blood flows into the left atrium from the left ventricle during the systolic phase of heart contraction. Mitral regurgitation is the most common form of valvular heart disease. Mitral regurgitation has different causes, such as leaflet prolapse, dysfunctional papillary muscles and/or stretching of the mitral valve annulus resulting from dilation of the left ventricle. Mitral regurgitation at a central portion of the leaflets can be referred to as central jet mitral regurgitation and mitral regurgitation nearer to one commissure (i.e., location where the leaflets meet) of the leaflets can be referred to as eccentric jet mitral regurgitation. Central jet regurgitation occurs when the edges of the leaflets do not meet in the middle and thus the valve does not close and regurgitation is present.

Some prior techniques for treating mitral regurgitation in patients include surgically stitching the edges of the native mitral valve leaflets directly to one another. A catheter delivered clip has been used to attempt to clip the sides of the leaflets together at the end portions of the leaflets, similar to the surgical stitching method. However, this clip has shortcomings, since it can only be used to clip the middle of the leaflets where they overlap by about 2 mm or more. Alternately, attempts have been made to use multiple clips on the commissures of the mitral valve, where there may be more overlap of the leaflets. This technique results in a longer operation time and also joins the patient's leaflets at the sides, restricting blood flow. Additionally, both the surgical and clip treatments are thought to create stress on patient leaflets.

Despite these prior techniques, there is a continuing need for improved devices and methods for treating mitral valve regurgitation.

SUMMARY

In view of the foregoing, a valve repair device for repairing a native heart valve of a patient includes a pair of clasps, where each clasp is configured to attach to native valve leaflet. The ends of the pair of clasps are configured to move away from one another to a partially open position when the native valve leaflets open during a diastolic phase of a cardiac cycle, and the ends of the pair of clasps are configured to move toward one another when the native valve leaflets close during a systolic phase of the cardiac cycle.

These and other aspects of the exemplary embodiments will become apparent from the following detailed description, taken in conjunction with the accompanying drawings, illustrating by way of example the principles of the various exemplary embodiments.

BRIEF DESCRIPTION OF THE DRAWINGS

To further clarify various aspects of embodiments of the present disclosure, a more particular description of the certain embodiments will be made by reference to various aspects of the appended drawings. It is appreciated that these drawings depict only typical embodiments of the present disclosure and are therefore not to be considered limiting of the scope of the disclosure. Moreover, while the figures can be drawn to scale for some embodiments, the figures are not necessarily drawn to scale for all embodiments. Embodiments and other features and advantages of the present disclosure will be described and explained with additional specificity and detail through the use of the accompanying drawings in which.

DETAILED DESCRIPTION

The following description refers to the accompanying drawings, which illustrate specific embodiments of the present disclosure. Other embodiments having different structures and operation do not depart from the scope of the present disclosure.

Exemplary embodiments of the present disclosure are directed to devices and methods for repairing a defective heart valve. It should be noted that various embodiments of native valve reparation devices and systems for delivery are disclosed herein, and any combination of these options can be made unless specifically excluded. In other words, individual components of the disclosed devices and systems can be combined unless mutually exclusive or otherwise physically impossible.

As described herein, when one or more components are described as being connected, joined, affixed, coupled, attached, or otherwise interconnected, such interconnection may be direct as between the components or may be indirect such as through the use of one or more intermediary components. Also as described herein, reference to a "member," "component," or "portion" shall not be limited to a single structural member, component, or element but can include an assembly of components, members, or elements. Also as described herein, the terms "substantially" and "about" are defined as at least close to (and includes) a given value or state (preferably within 10% of, more preferably within 1% of, and most preferably within 0.1% of).

Figure 1:
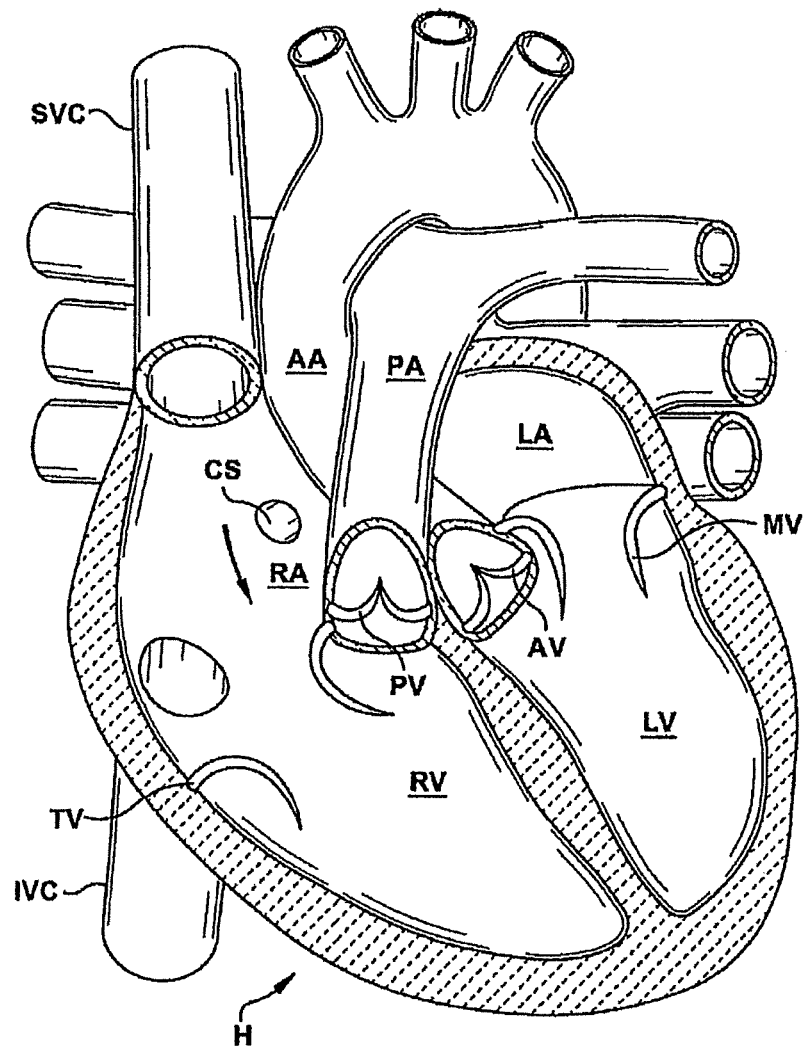
FIG. 1 illustrates a cutaway view of the human heart in a diastolic phase.
Figure 2:
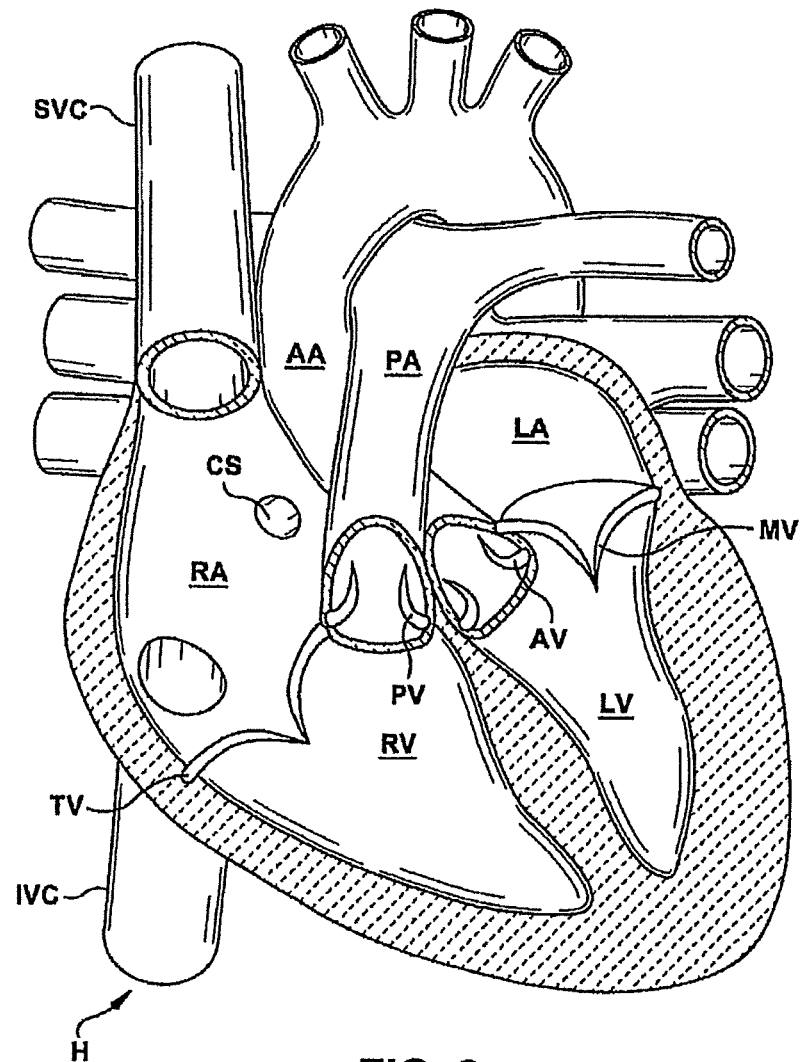
FIG. 2 illustrates a cutaway view of the human heart in a systolic phase.

FIGS. 1 and 2 are cutaway views of the human heart H in diastolic and systolic phases, respectively. The right ventricle RV and left ventricle LV are separated from the right atrium RA and left atrium LA, respectively, by the tricuspid valve TV and mitral valve MV; i.e., the atrioventricular valves. Additionally, the aortic valve AV separates the left ventricle LV from the ascending aorta AA, and the pulmonary valve PV separates the right ventricle from the pulmonary artery PA. Each of these valves has flexible leaflets (e.g., leaflets 20, 22 shown in FIGS. 4 and 5) extending inward across the respective orifices that come together or "coapt" in the flowstream to form the one-way, fluid-occluding surfaces. The native valve repair systems of the present application are described primarily with respect to the mitral valve MV. Therefore, anatomical structures of the left atrium LA and left ventricle LV will be explained in greater detail. It should be understood that the devices described herein may also be used in repairing other native valves, e.g., the devices can be used in repairing the tricuspid valve TV, the aortic valve AV, and the pulmonary valve PV.

The left atrium LA receives oxygenated blood from the lungs. During the diastolic phase, or diastole, seen in FIG. 1, the blood that was previously collected in the left atrium LA (during the systolic phase) moves through the mitral valve MV and into the left ventricle LV by expansion of the left ventricle LV. In the systolic phase, or systole, seen in FIG. 2, the left ventricle LV contracts to force the blood through the aortic valve AV and ascending aorta AA into the body. During systole, the leaflets of the mitral valve MV close to prevent the blood from regurgitating from the left ventricle LV and back into the left atrium LA, and blood is collected in the left atrium from the pulmonary vein. In one exemplary embodiment, the devices described by the present application are used to repair the function of a defective mitral valve MV. That is, the devices are configured to help close the leaflets of the mitral valve to prevent blood from regurgitating from the left ventricle LV and back into the left atrium LA. The devices described in the present application are designed to easily grasp and secure the native leaflets and assist them in coapting together in the regurgitant orifice.

Figure 3:
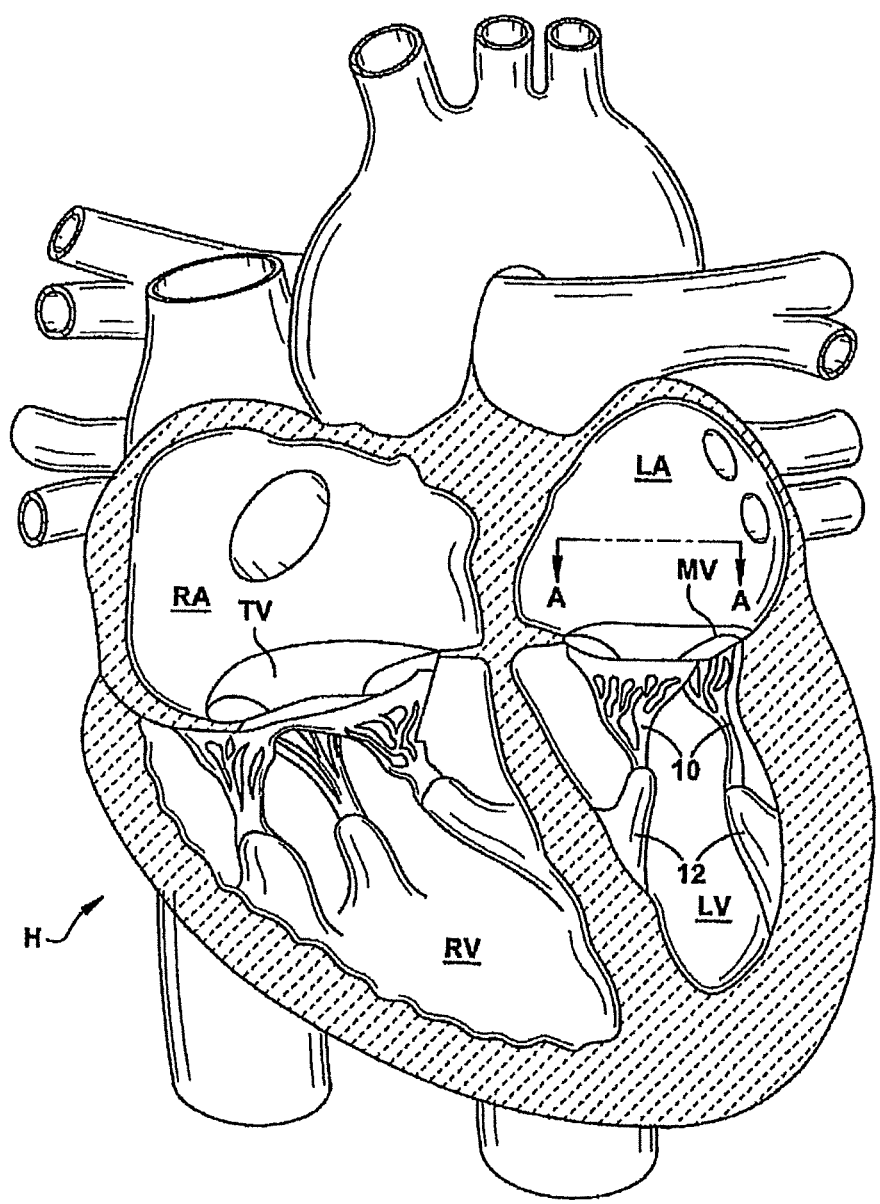
FIG. 3 illustrates a cutaway view of the human heart in a diastolic phase, in which the chordae tendineae are shown attaching the leaflets of the mitral and tricuspid valves to ventricle walls.

Referring now to FIGS. 1-7, the mitral valve MV includes two leaflets, the anterior leaflet 20 and the posterior leaflet 22. The mitral valve MV also includes an annulus 24, which is a variably dense fibrous ring of tissues that encircles the leaflets 20, 22. Referring to FIG. 3, the mitral valve MV is anchored to the wall of the left ventricle LV by chordae tendineae 10. The chordae tendineae 10 are cord-like tendons that connect the papillary muscles 12 (i.e., the muscles located at the base of the chordae tendineae and within the walls of the left ventricle) to the leaflets 20, 22 of the mitral valve MV. The papillary muscles 12 serve to limit the movements of the mitral valve MV and prevent the mitral valve from being reverted. The mitral valve MV opens and closes in response to pressure changes in the left atrium LA and the left ventricle LV. The papillary muscles do not open or close the mitral valve MV. Rather, the papillary muscles brace the mitral valve MV against the high pressure needed to circulate blood throughout the body. Together the papillary muscles and the chordae tendineae are known as the subvalvular apparatus, which functions to keep the mitral valve MV from prolapsing into the left atrium LA when the mitral valve closes.

Various disease processes can impair proper function of one or more of the native valves of the heart H. These disease processes include degenerative processes (e.g., Barlow's Disease, fibroelastic deficiency), inflammatory processes (e.g., Rheumatic Heart Disease), and infectious processes (e.g., endocarditis). In addition, damage to the left ventricle LV or the right ventricle RV from prior heart attacks (i.e., myocardial infarction secondary to coronary artery disease) or other heart diseases (e.g., cardiomyopathy) can distort a native valve's geometry, which can cause the native valve to dysfunction. However, the vast majority of patients undergoing valve surgery, such as surgery to the mitral valve MV, suffer from a degenerative disease that causes a malfunction in a leaflet (e.g., leaflets 20, 22) of a native valve (e.g., the mitral valve MV), which results in prolapse and regurgitation.

Generally, a native valve may malfunction in two different ways: (1) valve stenosis; and (2) valve regurgitation. Valve stenosis occurs when a native valve does not open completely and thereby causes an obstruction of blood flow. Typically, valve stenosis results from buildup of calcified material on the leaflets of a valve, which causes the leaflets to thicken and impairs the ability of the valve to fully open to permit forward blood flow.

The second type of valve malfunction, valve regurgitation, occurs when the leaflets of the valve do not close completely thereby causing blood to leak back into the prior chamber (e.g., causing blood to leak from the left ventricle to the left atrium). There are three mechanisms by which a native valve becomes regurgitant—or incompetent—which include Carpentier's type I, type II, and type III malfunctions. A Carpentier type I malfunction involves the dilation of the annulus such that normally functioning leaflets are distracted from each other and fail to form a tight seal (i.e., the leaflets do not coapt properly). Included in a type I mechanism malfunction are perforations of the leaflets, as are present in endocarditis. A Carpentier's type II malfunction involves prolapse of one or more leaflets of a native valve above a plane of coaption. A Carpentier's type III malfunction involves restriction of the motion of one or more leaflets of a native valve such that the leaflets are abnormally constrained below the plane of the annulus. Leaflet restriction can be caused by rheumatic disease (Ma) or dilation of a ventricle (Mb).

Figure 4:
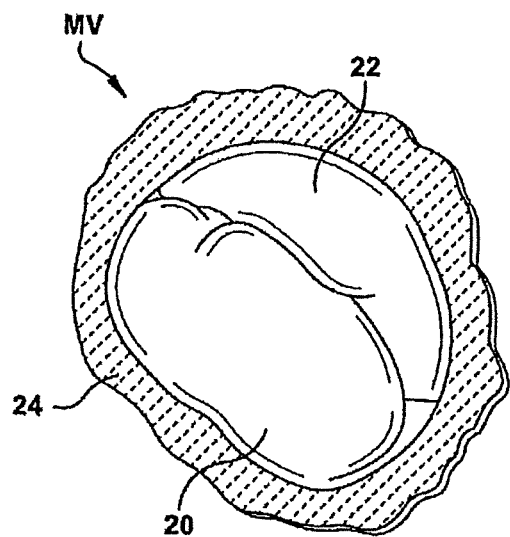
FIG. 4 illustrates a healthy mitral valve with the leaflets closed as viewed from an atrial side of the mitral valve.
Figure 5:
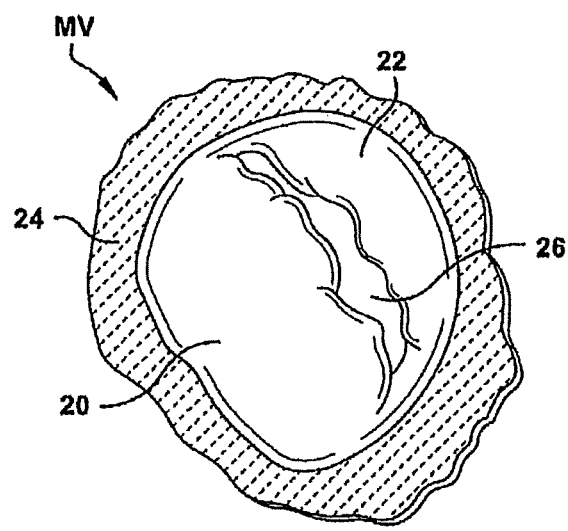
FIG. 5 illustrates a dysfunctional mitral valve with a visible gap between the leaflets as viewed from an atrial side of the mitral valve.

Referring to FIG. 4, when a healthy mitral valve MV is in a closed position, the anterior leaflet 20 and the posterior leaflet 22 coapt, which prevents blood from leaking from the left ventricle LV to the left atrium LA. Referring to FIG. 5, regurgitation occurs when the anterior leaflet 20 and/or the posterior leaflet 22 of the mitral valve MV is displaced into the left atrium LA during systole. This failure to coapt causes a gap 26 between the anterior leaflet 20 and the posterior leaflet 22, which allows blood to flow back into the left atrium LA from the left ventricle LV during systole. As set forth above, there are several different ways that a leaflet (e.g. leaflets 20, 22 of mitral valve MV) may malfunction, which can thereby lead to regurgitation.

Figure 6:
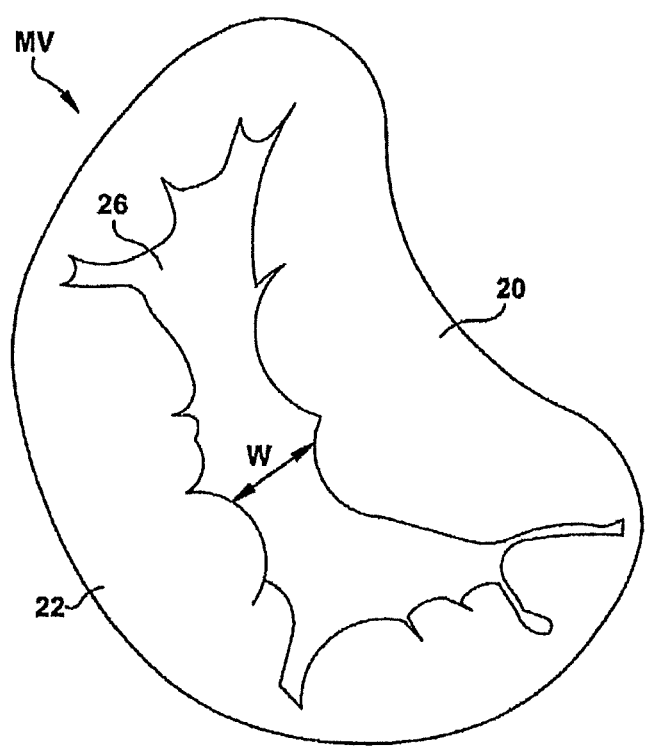
FIG. 6 illustrates a mitral valve having a wide gap between the posterior leaflet and the anterior leaflet.

Referring to FIG. 6, in certain situations, the mitral valve MV of a patient can have a wide gap 26 between the anterior leaflet 20 and the posterior leaflet 22 when the mitral valve is in a closed position (i.e., during the systolic phase). For example, the gap 26 can have a width W between about 2.5 mm and about 17.5 mm, such as between about 5 mm and about 15 mm, such as between about 7.5 mm and about 12.5 mm, such as about 10 mm. In some situations, the gap 26 can have a width W greater than 15 mm. In any of the above-mentioned situations, a valve repair device is desired that is capable of engaging the anterior leaflet 20 and the posterior leaflet 22 to close the gap 26 and prevent regurgitation of blood through the mitral valve MV.

Although stenosis or regurgitation can affect any valve, stenosis is predominantly found to affect either the aortic valve AV or the pulmonary valve PV, and regurgitation is predominantly found to affect either the mitral valve MV or the tricuspid valve TV. Both valve stenosis and valve regurgitation increase the workload of the heart H and may lead to very serious conditions if left un-treated; such as endocarditis, congestive heart failure, permanent heart damage, cardiac arrest, and ultimately death. Because the left side of the heart (i.e., the left atrium LA, the left ventricle LV, the mitral valve MV, and the aortic valve AV) is primarily responsible for circulating the flow of blood throughout the body, malfunction of the mitral valve MV or the aortic valve AV is particularly problematic and often life threatening. Accordingly, because of the substantially higher pressures on the left side of the heart, dysfunction of the mitral valve MV or the aortic valve AV is much more problematic.

Malfunctioning native heart valves may either be repaired or replaced. Repair typically involves the preservation and correction of the patient's native valve. Replacement typically involves replacing the patient's native valve with a biological or mechanical substitute. Typically, the aortic valve AV and pulmonary valve PV are more prone to stenosis. Because stenotic damage sustained by the leaflets is irreversible, the most conventional treatments for a stenotic aortic valve or stenotic pulmonary valve are removal and replacement of the valve with a surgically implanted heart valve, or displacement of the valve with a transcatheter heart valve. The mitral valve MV and the tricuspid valve TV are more prone to deformation of leaflets, which, as described above, prevents the mitral valve or tricuspid valve from closing properly and allows for regurgitation or back flow of blood from the ventricle into the atrium (e.g., a deformed mitral valve MV may allow for regurgitation or back flow from the left ventricle LV to the left atrium LA). The regurgitation or back flow of blood from the ventricle to the atrium results in valvular insufficiency. Deformations in the structure or shape of the mitral valve MV or the tricuspid valve TV are often repairable. In addition, regurgitation can occur due to the chordae tendineae 10 becoming dysfunctional (e.g., the chordae tendineae may stretch or rupture), which allows the anterior leaflet 20 and the posterior leaflet 22 to be reverted such that blood is regurgitated into the left atrium LA. The problems occurring due to dysfunctional chordae tendineae 10 can be repaired by repairing the chordae tendineae or the structure of the mitral valve (e.g., by securing the leaflets 20, 22 at the affected portion of the mitral valve).

Implantable prosthetic devices for repairing the mitral valve can repair the structure of the mitral valve to approximate the leaflets together and reduce regurgitation. If leaflets are not able to open a sufficient amount once an implant is in place, however, an increase in the pressure gradient across a valve can occur. For example, a pressure gradient of 5 mmHg or more across the mitral valve is correlated with the development of stenosis in the valve. Thus, there can be a correlation between the pressure gradient across the mitral valve and the rigidity of the repair device used to repair the valve. An implant that maintains an effective orifice area when the leaflets are open can maintain a lower pressure gradient than conventional implants. In the exemplary embodiments described herein, the implants can be configured to both reduce regurgitation when the native valve is closed and only minimally impact pressure gradients across the native valve when the native valve is open. The exemplary valve repair devices can also be useful for valves with a small valve area, such as less than 4.0 cm2. The exemplary embodiments described herein can enhance leaflet mobility and effective orifice area (EOA) after implantation as compared to valve replacement devices that do not open or flex open as the heart beats.

Various embodiments described herein approximate the leaflets while not excessively reducing the EOA and thereby only minimally affecting the pressure gradient across the native valve. In one exemplary embodiment, this is done by locking clasp and/or paddle arms in an open or partially position and/or by allowing for movement of the paddles with the native valve leaflet. These embodiments can permit tissue ingrowth such that a double orifice is formed. This provides a healing response while mitigating the restriction of the native valve.

As will be described in more detail below, pressure gradients across the mitral valve or across the tricuspid valve can be kept at acceptable levels with the prosthetic valve repair devices described herein. In some exemplary embodiments, devices described in U.S. provisional application No. 62/744,031, filed Oct. 10, 2018, which is incorporated by reference herein in its entirety, can be flexible to allow the paddles of the device to flex when the native valve opens. This flexibility can reduce the amount of immobilized tissue of the leaflets when a device is clasped onto the leaflets and can reduce the change in pressure gradient.

Certain exemplary embodiments for increasing the mobility of the leaflets can have an implantable prosthetic device with increased flexibility and/or that can move and/or flex with the leaflets as they open and close during the cardiac cycle. This can be achieved by configuring the paddles to open and close with the native valve during the cardiac cycle, by reducing the profile of the coaption device, by reducing the profile of the paddles, and/or by making the paddles flexible enough to flex open with the native valve during the cardiac cycle.

In other exemplary embodiments, flexibility of the leaflets can be improved by having both a flexible portion and an immobilized portion of the device, once implanted. In certain exemplary embodiments, the paddles can remain fixed, or propped, open. This can immobilize the tips of the leaflets while maintaining mobility of the leaflet. As will be explained in more detail below, these embodiments can provide an improved acute response in reducing regurgitation and/or in providing tissue ingrowth.

Figure 7:
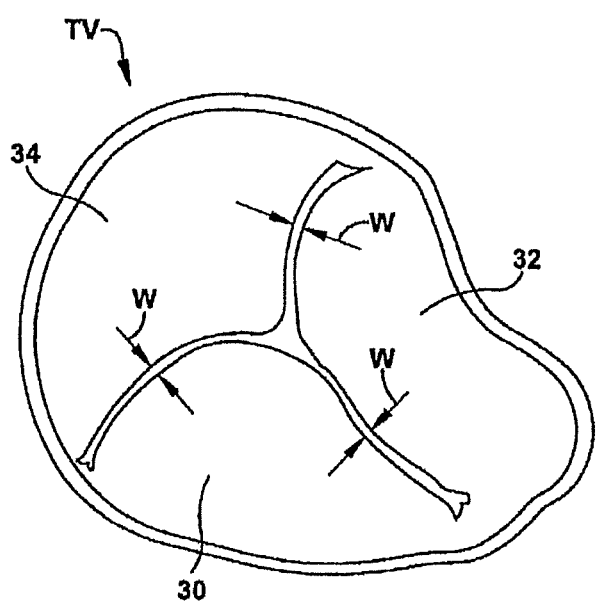
FIG. 7 illustrates a tricuspid valve viewed from an atrial side of the tricuspid valve.

The devices and procedures disclosed herein make reference to repairing the structure of a mitral valve. However, it should be understood that the devices and concepts provided herein can be used to repair any native valve, as well as any component of a native valve. Referring now to FIG. 7, any of the devices and concepts provided herein can be used to repair the tricuspid valve TV. For example, any of the devices and concepts provided herein can be used between any two of the anterior leaflet 30, septal leaflet 32, and posterior leaflet 34 to prevent regurgitation of blood from the right ventricle into the right atrium. In addition, any of the devices and concepts provided herein can be used on all three of the leaflets 30, 32, 34 together to prevent regurgitation of blood from the right ventricle to the right atrium. That is, the valve repair devices provided herein can be centrally located between the three leaflets 30, 32, 34.

An exemplary implantable prosthetic device has a coaption element and at least one anchor. The anchor region can be where the individual components of the device are mechanically connected together, and there can be a cap or base at the anchor, as well as joints that permit the paddles and clasps to pivot. The coaption element is configured to be positioned within the native heart valve orifice to help fill the space and form a more effective seal, thereby reducing or preventing regurgitation described above. The coaption element can have a structure that is impervious to blood and that allows the native leaflets to close around the coaption element during ventricular systole to block blood from flowing from the left or right ventricle back into the left or right atrium, respectively. The prosthetic device can be configured to seal against two or three native valve leaflets; that is, the device may be used in the native mitral (bicuspid) and tricuspid valves. The coaption element is sometimes referred to herein as a spacer because the coaption element can fill a space between improperly functioning native mitral or tricuspid leaflets that do not close completely.

The coaption element can have various shapes. In some embodiments, the coaption element can have an elongated cylindrical shape having a round cross-sectional shape. In other embodiments, the coaption element can have an oval cross-sectional shape, a crescent cross-sectional shape, or various other non-cylindrical shapes. The coaption element can have an atrial portion positioned in or adjacent to the left atrium, a ventricular or lower portion positioned in or adjacent to the left ventricle, and a side surface that extends between the native mitral leaflets. In embodiments configured for use in the tricuspid valve, the atrial or upper portion is positioned in or adjacent to the right atrium, and the ventricular or lower portion is positioned in or adjacent to the right ventricle, and the side surface that extends between the native tricuspid leaflets.

The anchor can be configured to secure the device to one or both of the native mitral leaflets such that the coaption element is positioned between the two native leaflets. In embodiments configured for use in the tricuspid valve, the anchor is configured to secure the device to one, two, or three of the tricuspid leaflets such that the coaption element is positioned between the three native leaflets. As described herein, the paddles (see paddles 520, 522 in FIGS. 36-38 for example) are anchoring paddles and are a part of the anchor. In some embodiments, the anchor can attach to the coaption element at a location adjacent the ventricular portion of the coaption element. In some embodiments, the anchor can attach to a shaft or actuation wire, to which the coaption element is also attached. In some embodiments, the anchor and the coaption element can be positioned independently with respect to each other by separately moving each of the anchor and the coaption element along the longitudinal axis of the shaft or actuation wire. In some embodiments, the anchor and the coaption element can be positioned simultaneously by moving the anchor and the coaption element together along the longitudinal axis of the shaft or actuation wire. The anchor can be configured to be positioned behind a native leaflet when implanted such that the leaflet is grasped by the anchor.

The prosthetic device can be configured to be implanted via a delivery sheath. The coaption element and the anchor can be compressible to a radially compressed state and can be self-expandable to a radially expanded state when compressive pressure is released. The device can be configured for the anchor to be expanded radially away from the still-compressed coaption element initially in order to create a gap between the coaption element and the anchor. A native leaflet can then be positioned in the gap. The coaption element can be expanded radially, closing the gap between the coaption element and the anchor and capturing the leaflet between the coaption element and the anchor. In some embodiments, the anchor and coaption element are optionally configured to self-expand.

The disclosed prosthetic devices can be configured such that the anchor is connected to a leaflet, taking advantage of the tension from native chordae tendineae to resist high systolic pressure urging the device toward the left atrium. During diastole, the devices can rely on the compressive and retention forces exerted on the leaflet that is grasped by the anchor.

Referring now to FIGS. 8-14, a schematically illustrated implantable prosthetic device 100 is shown in various stages of deployment. The device 100 can include any other features for an implantable prosthetic device discussed in the present application, and the device 100 can be positioned to engage valve tissue 20, 22 as part of any suitable valve repair system (e.g., any valve repair system disclosed in the present application).

The device 100 is deployed from a delivery sheath or means for delivery 102 and includes a coaption portion 104 and an anchor portion 106. The coaption portion 104 of the device 100 includes a coaption element or means for coapting 110 that is adapted to be implanted between the leaflets of the native mitral valve and is slidably attached to an actuation wire or shaft 112. The anchor portion 106 is actuatable between open and closed conditions and can take a wide variety of forms, such as, for example, paddles, gripping elements, or the like. Actuation of the actuation wire or means for actuating 112 opens and closes the anchor portion 106 of the device 100 to grasp the mitral valve leaflets during implantation. The actuation wire or shaft 112 may take a wide variety of different forms. For example, the actuation wire or shaft may be threaded such that rotation of the actuation wire or shaft moves the anchor portion 106 relative to the coaption portion 104. Or, the actuation wire or shaft may be unthreaded, such that pushing or pulling the actuation wire or shaft 112 moves the anchor portion 106 relative to the coaption portion 104.

The anchor portion 106 of the device 100 includes outer paddles 120 and inner paddles 122 that are connected between a cap 114 and the coaption element or means for coapting 110 by portions 124, 126, 128. The portions 124, 126, 128 may be jointed and/or flexible to move between all of the positions described below. The jointed portions may be joints and the flexible portions may be flexible connections. The interconnection of the outer paddles 120, the inner paddles 122, the coaption element or means for coapting 110, and the cap 114 by the portions 124, 126, and 128 can constrain the device to the positions and movements illustrated herein.

The actuation wire or means for actuating 112 extends through the delivery sheath and the coaption element or means for coapting 110 to the cap 114 at the distal connection of the anchor portion 106. Extending and retracting the actuation wire or means for actuating 112 increases and decreases the spacing between the coaption element or means for coapting 110 and the cap 114, respectively. A collar removably attaches the coaption element or means for coapting 110 to the delivery sheath or means for delivery 102 so that the actuation wire or means for actuating 112 slides through the collar and coaption element or means for coapting 110 during actuation to open and close the paddles 120, 122 of the anchor portion 106.

Figure 11:
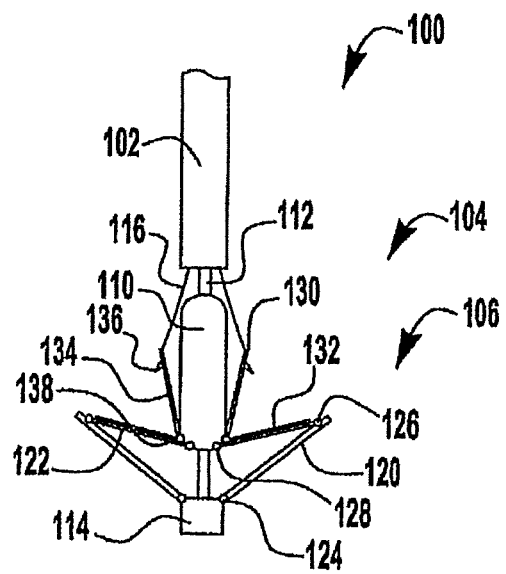

Referring now to FIG. 11, the anchor portion 106 includes attachment portions or gripping members. The illustrated gripping members are barbed clasps 130 that include a base or fixed arm 132, a moveable arm 134, barbs or means for securing 136, and a joint portion 138. The fixed arms 132 are attached to the inner paddles 122, with the joint portion 138 disposed proximate the coaption element or means for coapting 110. The barbed clasps have flat surfaces and do not fit in a recess of the paddle. Rather, the flat portions of the barbed clasps are disposed against the surface of the inner paddle 122. The joint portion 138 provides a spring force between the fixed and moveable arms 132, 134 of the barbed clasp 130. The joint portion 138 can be any suitable joint, such as a flexible joint, a spring joint, a pivot joint, or the like. In certain embodiments, the joint portion 138 is a flexible piece of material integrally formed with the fixed and moveable arms 132, 134. The fixed arms 132 are attached (i.e., fixed) to the inner paddles 122 and remain stationary relative to the inner paddles 122 when the moveable arms 134 are opened to open the barbed clasps 130 and expose the barbs or means for securing 136. The barbed clasps 130 are opened by applying tension to actuation lines 116 attached to the moveable arms 134, thereby causing the moveable arms 134 to pivot on the joint portions 138.

During implantation, the paddles 120, 122 are opened and closed to grasp the native mitral valve leaflets between the paddles 120, 122 and the coaption element or means for coapting 110. The barbed clasps 130 further secure the native leaflets by engaging the leaflets with barbs or means for securing 136 and pinching the leaflets between the moveable and fixed arms 134, 132. The barbs or means for securing 136 of the barbed clasps 130 increase friction with the leaflets or may partially or completely puncture the leaflets. The actuation lines 116 can be actuated separately so that each barbed clasp 130 can be opened and closed separately. Separate operation allows one leaflet to be grasped at a time, or for the repositioning of a clasp 130 on a leaflet that was insufficiently grasped, without altering a successful grasp on the other leaflet. The barbed clasps 130 can be opened and closed relative to the position of the inner paddle 122 (as long as the inner paddle is in an open position), thereby allowing leaflets to be grasped in a variety of positions as the particular situation requires.

The barbed clasps 130 can be opened separately by pulling on an attached actuation line 116 that extends through the delivery sheath or means for delivery 102 to the barbed clasp 130. The actuation line 116 can take a wide variety of forms, such as, for example, a line, a suture, a wire, a rod, a catheter, or the like. The barbed clasps 130 can be spring loaded so that in the closed position the barbed clasps 130 continue to provide a pinching force on the grasped native leaflet. This pinching force remains constant regardless of the position of the inner paddles 122. Barbs or means for securing 136 of the barbed clasps 130 can pierce the native leaflets to further secure the native leaflets.

Figure 8:
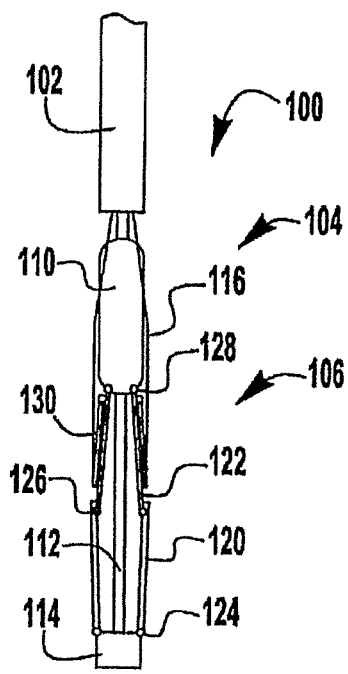
FIGS. 8-14 show an exemplary embodiment of an implantable prosthetic device, in various stages of deployment.

Referring now to FIG. 8, the device 100 is shown in an elongated or fully open condition for deployment from the delivery sheath. The device 100 is loaded in the delivery sheath in the fully open position, because the fully open position takes up the least space and allows the smallest catheter to be used (or the largest device 100 to be used for a given catheter size). In the elongated condition the cap 114 is spaced apart from the coaption element or means for coapting 110 such that the paddles 120, 122 of the anchor portion 106 are fully extended. In some embodiments, an angle formed between the interior of the outer and inner paddles 120, 122 is approximately 180 degrees. The barbed clasps 130 are kept in a closed condition during deployment through the delivery sheath or means for delivery 102 so that the barbs or means for securing 136 (FIG. 11) do not catch or damage the sheath or tissue in the patient's heart.

Figure 9:
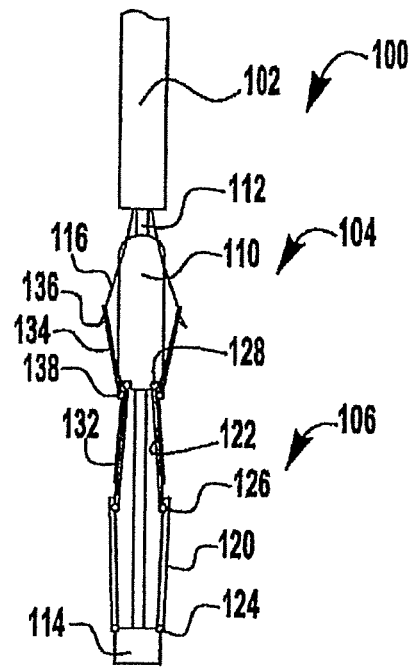

Referring now to FIG. 9, the device 100 is shown in an elongated detangling condition, similar to FIG. 8, but with the barbed clasps 130 in a fully open position, ranging from about 140 degrees to about 200 degrees, to about 170 degrees to about 190 degrees, or about 180 degrees between fixed and moveable portions of the barbed clasps 130. Fully opening the paddles 120, 122 and the clasps 130 has been found to improve ease of detanglement from anatomy of the patient during implantation of the device 100.

Figure 10:
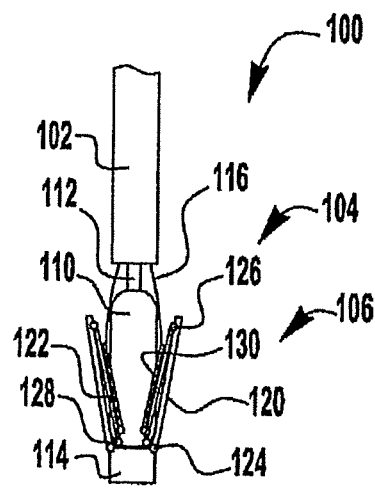

Referring now to FIG. 10, the device 100 is shown in a shortened or fully closed condition. The compact size of the device 100 in the shortened condition allows for easier maneuvering and placement within the heart. To move the device 100 from the elongated condition to the shortened condition, the actuation wire or means for actuating 112 is retracted to pull the cap 114 towards the coaption element or means for coapting 110. The joints or flexible connections 126 between the outer paddle 120 and inner paddle 122 are constrained in movement such that compression forces acting on the outer paddle 120 from the cap 114 being retracted towards the coaption element or means for coapting 110 cause the paddles or gripping elements 120, 122 to move radially outward. During movement from the open to closed position, the outer paddles 120 maintain an acute angle with the actuation wire or means for actuating 112. The outer paddles 120 can optionally be biased toward a closed position. The inner paddles 122 during the same motion move through a considerably larger angle as they are oriented away from the coaption element or means for coapting 110 in the open condition and collapse along the sides of the coaption element or means for coapting 110 in the closed condition. In certain embodiments, the inner paddles 122 are thinner and/or narrower than the outer paddles 120, and the joint or flexible portions 126, 128 connected to the inner paddles 122 can be thinner and/or more flexible. For example, this increased flexibility can allow more movement than the joint or flexible portion 124 connecting the outer paddle 120 to the cap 114. In certain other embodiments, the outer paddles 120 are narrower than the inner paddles 122. The joint or flexible portions 126, 128 connected to the inner paddles 122 can be more flexible, for example, to allow more movement than the joint or flexible portion 124 connecting the outer paddle 124 to the cap 114. In yet another embodiment, the inner paddles 122 can be the same or substantially the same width as the outer paddles.

Figure 12:
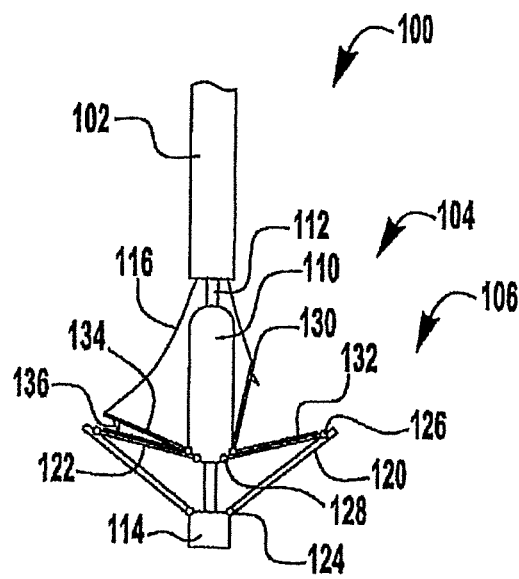
Figure 13:
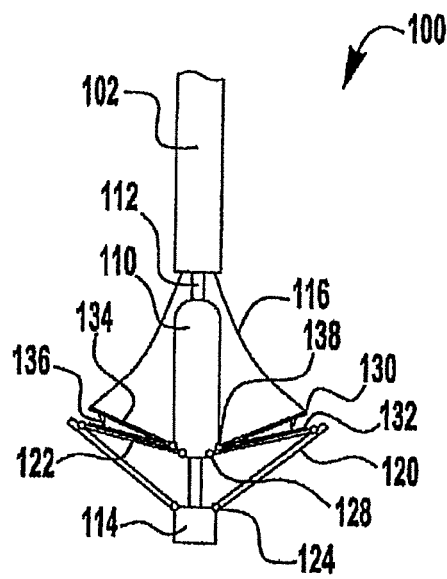

Referring now to FIGS. 11-13, the device 100 is shown in a partially open, grasp-ready condition. To transition from the fully closed to the partially open condition, the actuation wire or means for actuating 112 is extended to push the cap 114 away from the coaption element or means for coapting 110, thereby pulling on the outer paddles 120, which in turn pulls on the inner paddles 122, causing the anchor portion 106 to partially unfold. The actuation lines 116 are also retracted to open the clasps 130 so that the leaflets can be grasped. In the example illustrated by FIG. 11, the pair of inner and outer paddles 122, 120 are moved in unison, rather than independently, by a single actuation wire or means for actuating 112. Also, the positions of the clasps 130 are dependent on the positions of the paddles 122, 120. For example, referring to FIG. 10 closing the paddles 122, 120 also closes the clasps.

Figure 11A:
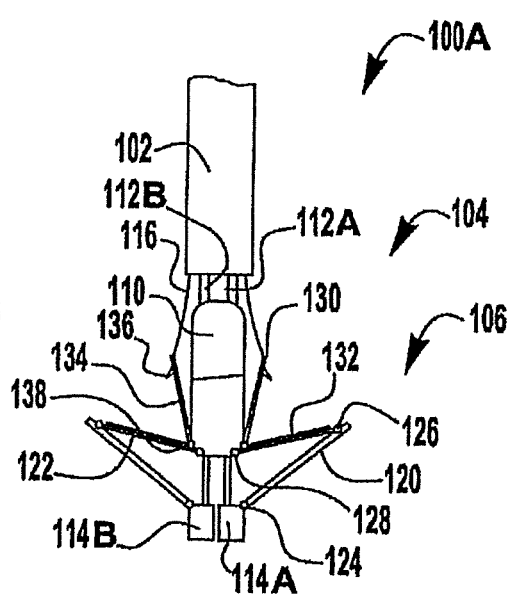
FIG. 11A shows an exemplary embodiment of an implantable prosthetic device that is similar to the device illustrated by FIG. 11, but where the paddles are independently controllable.

FIG. 11A illustrates an exemplary embodiment where the paddles 120, 122 are independently controllable. The device 100A illustrated by FIG. 11A is similar to the device illustrated by FIG. 11, except the device 100A includes two independent actuation wires 112A, 112B that are coupled to two independent caps 114A, 114B. To transition a first inner paddle and a first outer paddle from the fully closed to the partially open condition, the actuation wire or means for actuating 112A is extended to push the cap 114A away from the coaption element or means for coapting 110, thereby pulling on the outer paddle 120, which in turn pulls on the inner paddle 122, causing the first anchor portion 106 to partially unfold. To transition a second inner paddle and a second outer paddle from the fully closed to the partially open condition, the actuation wire or means for actuating 112B is extended to push the cap 114 away from the coaption element or means for coapting 110, thereby pulling on the outer paddle 120, which in turn pulls on the inner paddle 122, causing the second anchor portion 106 to partially unfold. The independent paddle control illustrated by FIG. 11A can be implemented on any of the devices disclosed by the present application.

Referring now to FIG. 12, one of the actuation lines 116 is extended to allow one of the clasps 130 to close. Referring now to FIG. 13, the other actuation line 116 is extended to allow the other clasp 130 to close. Either or both of the actuation lines 116 may be repeatedly actuated to repeatedly open and close the barbed clasps 130.

Figure 14:
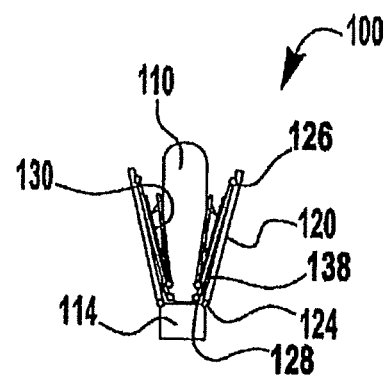

Referring now to FIG. 14, the device 100 is shown in a fully closed and deployed condition. The deployed condition may be the position illustrated by FIG. 14 or some position between the position illustrated by FIG. 14 and the position illustrated by FIG. 13. The delivery sheath or means for delivery 102 and actuation wire or means for actuating 112 are retracted and the paddles 120, 122 and clasps 130 remain fully closed around the leaflets. Once deployed, the device 100 may be biased toward the deployed position, such that the device 100 remains in the deployed position or such that the device closes to the deployed position each time the native valve closes, but the biasing allows the device to open past the deployed position each time the native valve opens. This can be achieved through the use of spring materials, such as steel, other metals, plastics, composites, etc. or shape-memory alloys such as Nitinol. For example, the jointed or flexible portions 124, 126, 128, 138, and/or the inner and outer paddles 122, and/or an additional biasing component (see biasing member 524 in FIG. 47A) may be formed of metals such as steel or shape-memory alloy, such as Nitinol—produced in a wire, sheet, tubing, or laser sintered powder—and bias the outer paddles 120 toward being closed around the coaption element or means for coapting 110 and the barbed clasps 130 pinched around native leaflets. Similarly, the fixed and moveable arms 132, 134 of the barbed clasps 130 are biased to pinch the leaflets. In certain embodiments, the joint portions 124, 126, 128, 138, and/or the inner and outer paddles 122, and/or an additional biasing component (see biasing member 524 in FIG. 47A) may be formed of any other suitably elastic material, such as a metal or polymer material, to maintain the device in the closed condition after implantation or to close the device each time the native valve closes, but also allow the device to open or partially open each time the native vale opens.

Figure 15:
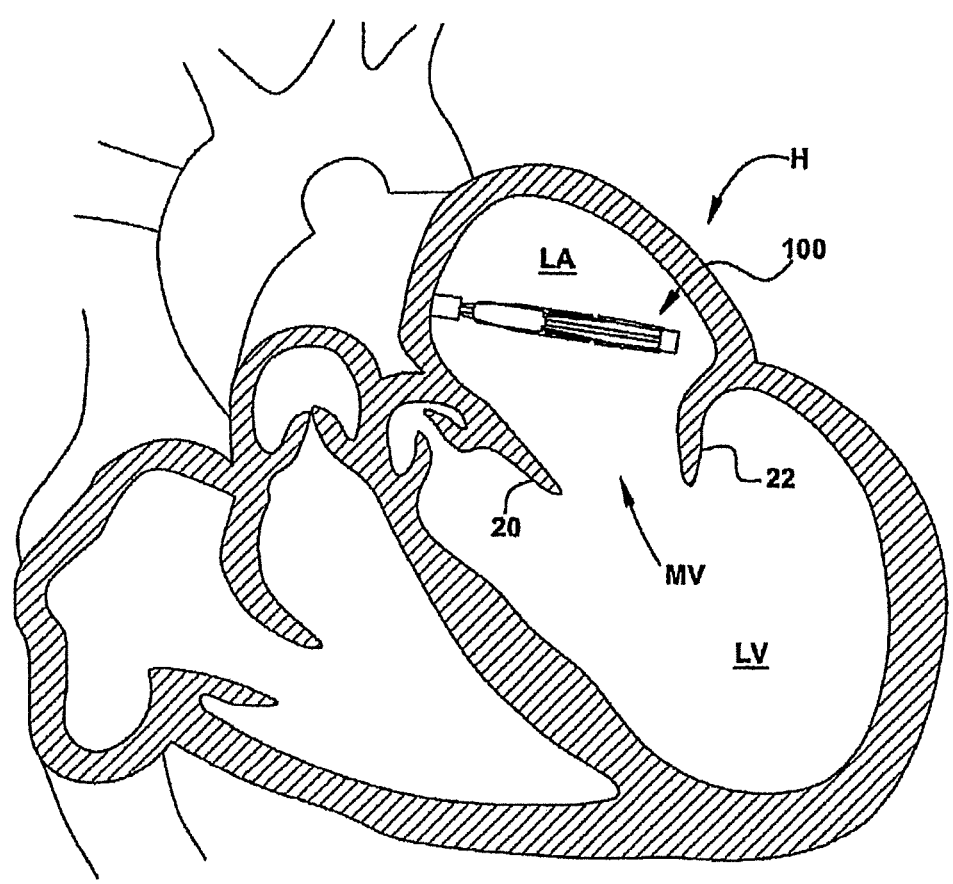
FIGS. 15-20 show the implantable prosthetic device of FIGS. 8-14 being delivered and implanted within the native mitral valve.
Figure 16:
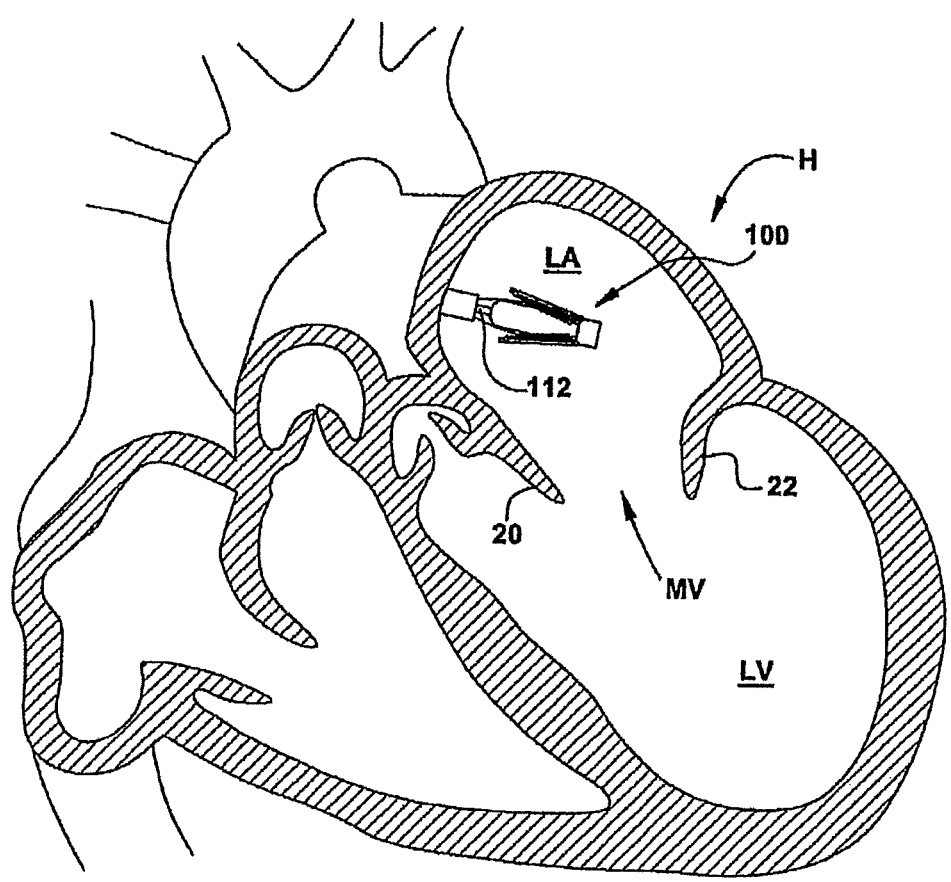
Figure 17:
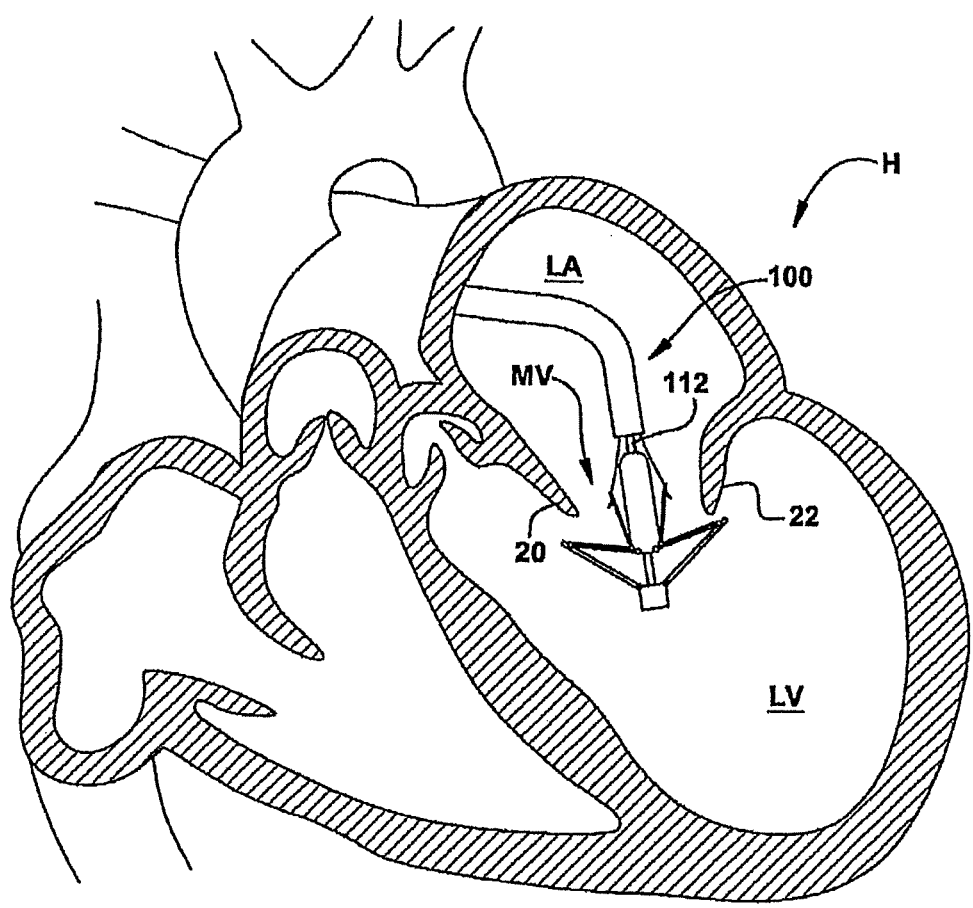
Figure 18:
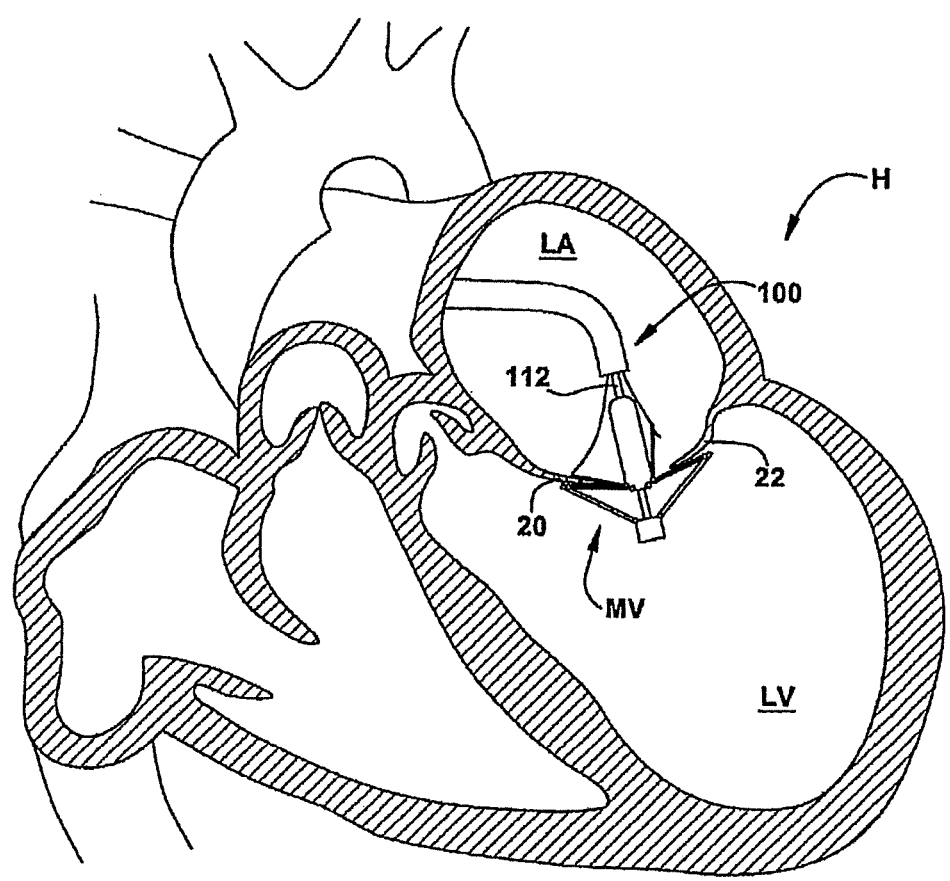
Figure 19:
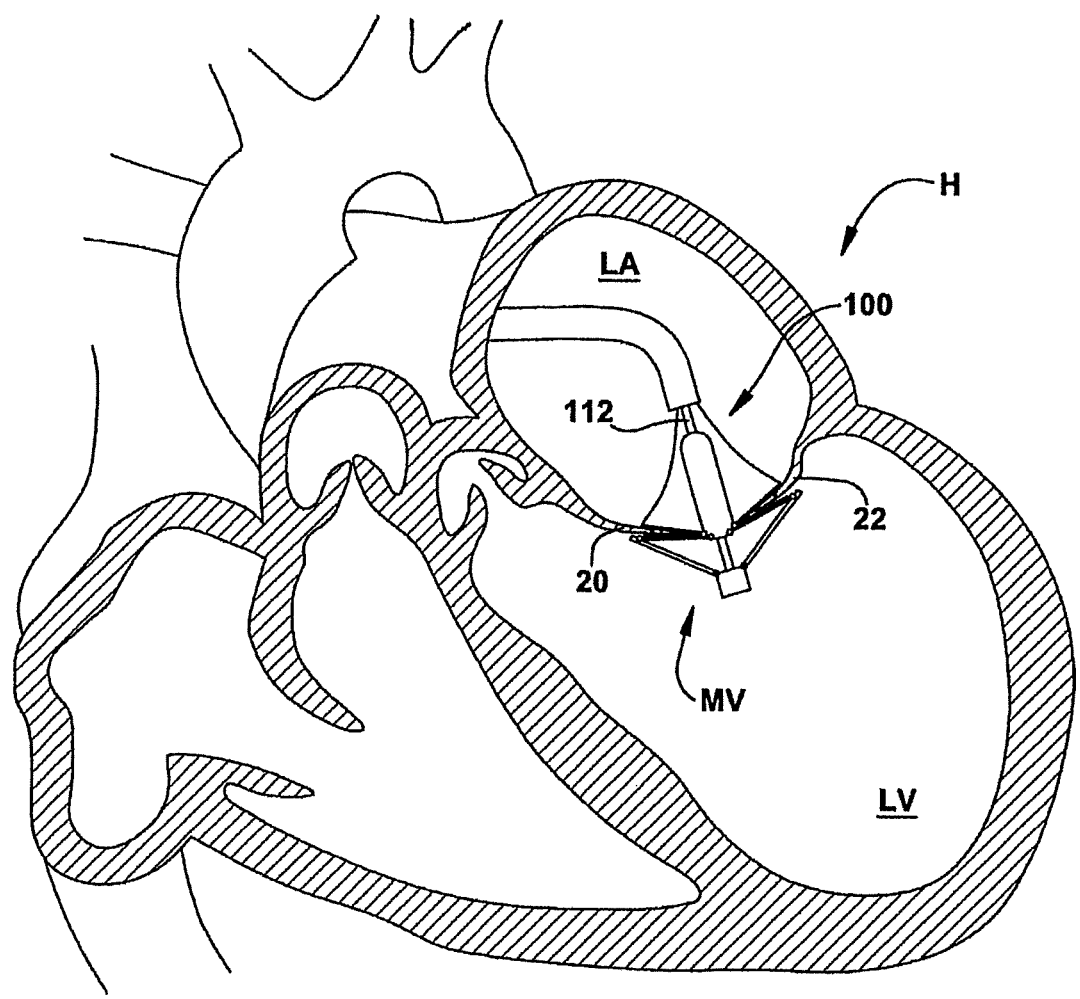
Figure 20:
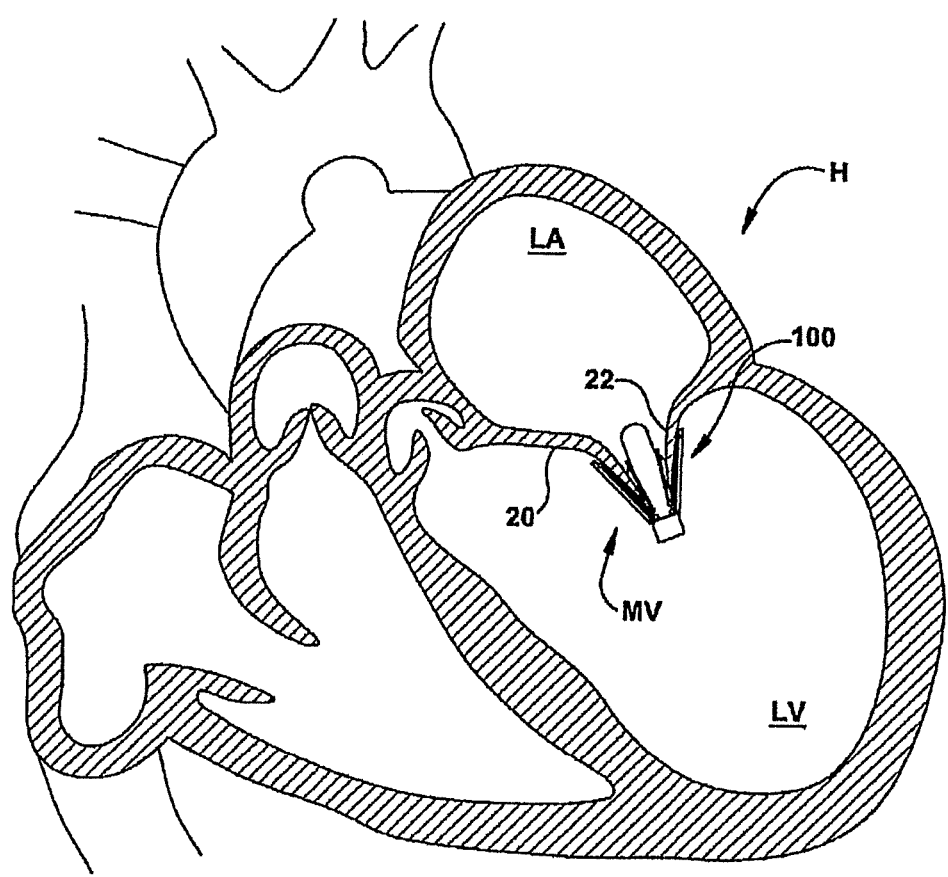

Referring now to FIGS. 15-20, the implantable device 100 of FIGS. 8-14 is shown being delivered and implanted within the native mitral valve MV of the heart H. Referring now to FIG. 15, the delivery sheath is inserted into the left atrium LA through the septum and the device 100 is deployed from the delivery sheath in the fully open condition. The actuation wire or means for actuating 112 is then retracted to move the device 100 into the fully closed condition shown in FIG. 16. As can be seen in FIG. 17, the device 100 is moved into position within the mitral valve MV into the ventricle LV and partially opened so that the leaflets 20, 22 can be grasped. Referring now to FIG. 18, an actuation line 116 is extended to close one of the clasps 130, capturing a leaflet 20. FIG. 19 shows the other actuation line 116 being then extended to close the other clasp 130, capturing the remaining leaflet 22. Lastly, as can be seen in FIG. 20, the delivery sheath or means for delivery 102 and actuation wire or means for actuating 112 and actuation lines 116 are then retracted to leave the device 100 in the deployed position in the native mitral valve MV. IN the example illustrated by FIG. 20, the device is fully closed in the deployed position. In other exemplary embodiments, the device 100 can be deployed in any position between the position illustrated by FIG. 19 and FIG. 20. That is, the device does not need to be fully closed in some exemplary embodiments.

The features including structure, material, and connectivity to each other to form the device, of the clasps, paddles, coaption elements and delivery devices and methods can vary among the exemplary embodiments, and combinations of the different embodiments can be combined to form additional embodiments within the scope of the disclosure. The devices can incorporate features such as those in U.S. provisional application No. 62/744,031, filed on Oct. 10, 2018, and U.S. application Ser. No. 15/865,890, filed Jan. 9, 2018, both of which are incorporated by reference herein in their entireties.

The devices 100, 400, 400A 500, and 600 described herein can be positioned to engage valve tissue 20, 22 as part of any suitable valve repair system (e.g., any valve repair system disclosed in the present application). In one exemplary embodiment, any of these devices 100, 400, 500, and 600 can be configured to open and close with the opening and closing of the native valve. In one exemplary embodiment, any of these devices 100, 400, 500, and 600 can be configured to be implanted in a partially open condition and can optionally be configured to further open and return to the partially open, implanted position with the opening and closing of the native valve.

Figure 21:
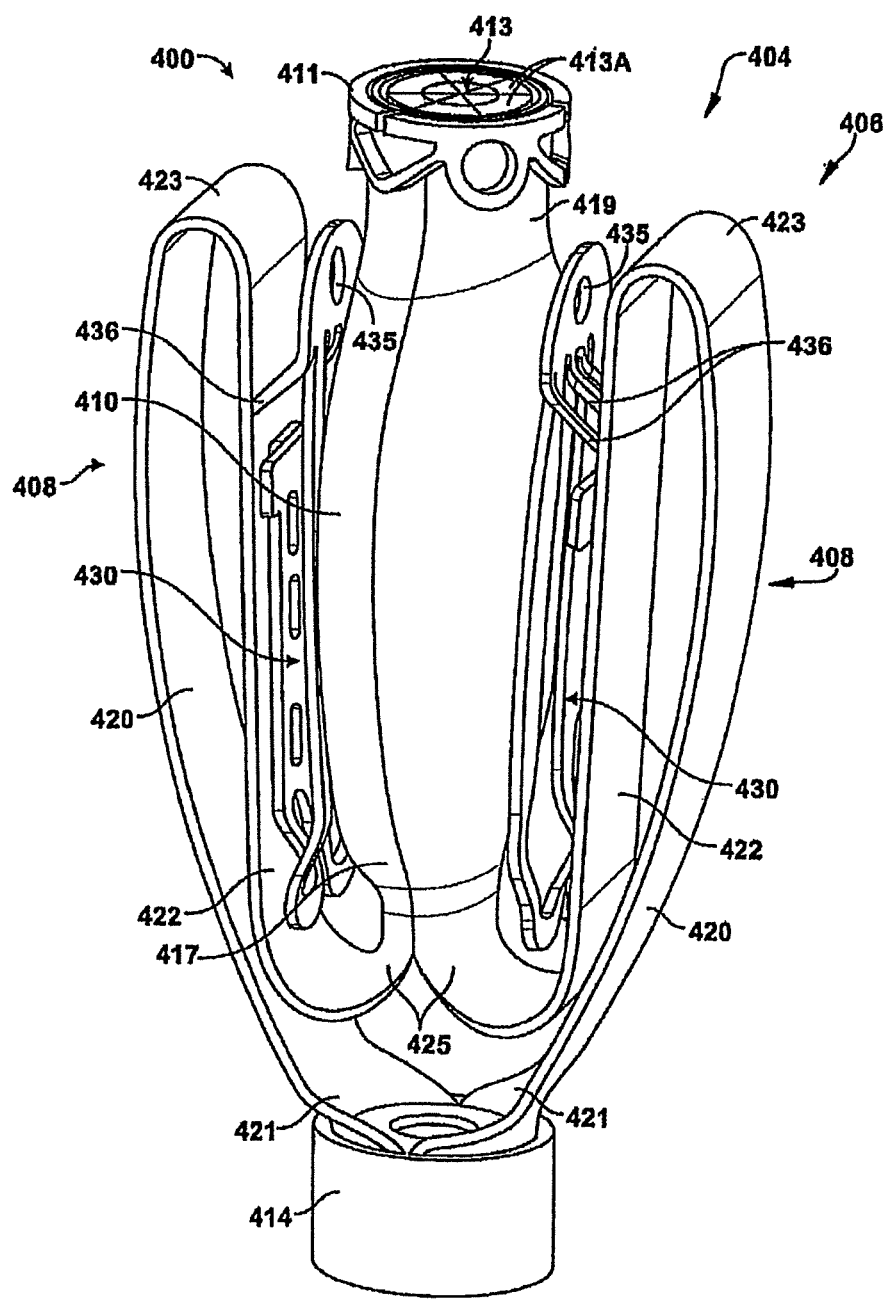
FIGS. 21-23 show an exemplary embodiment of an implantable prosthetic device.
Figure 22:
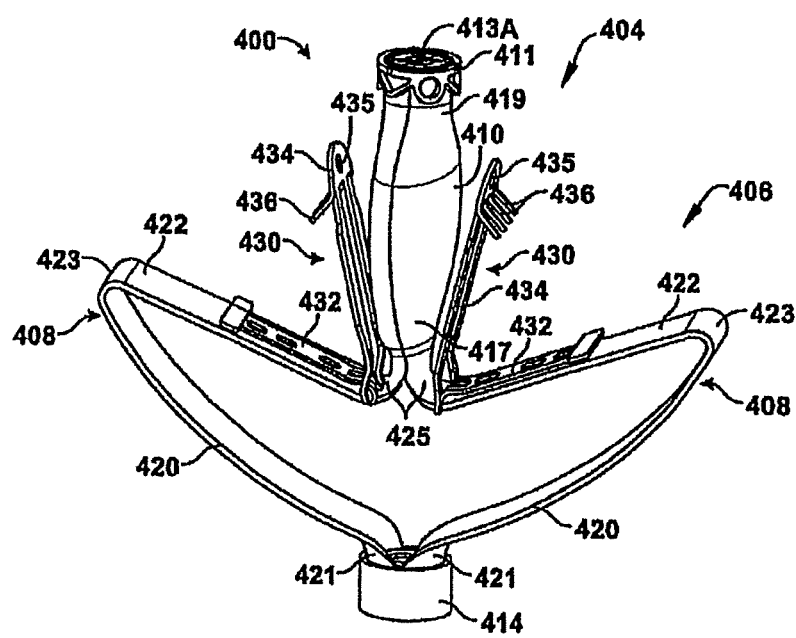
Figure 23:
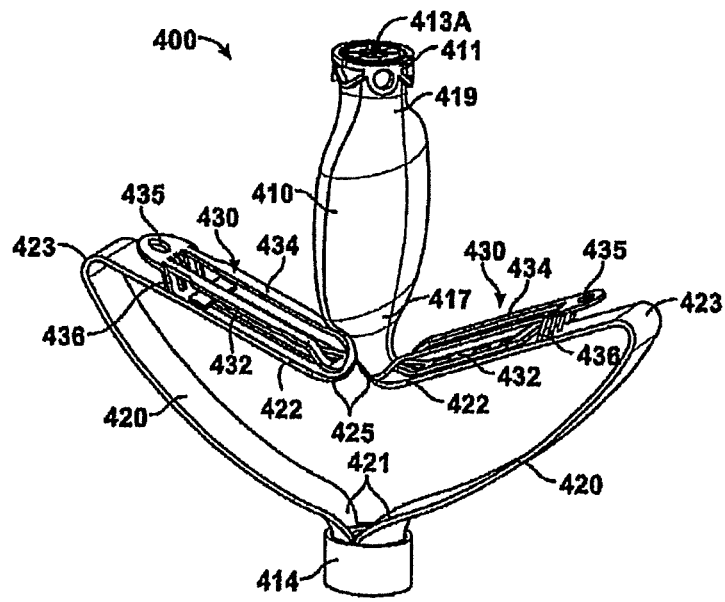

Referring now to FIGS. 21-23, an exemplary embodiment of an implantable prosthetic device 400 is shown. The device 400 can include any other features for an implantable prosthetic device discussed in the present application, and the device 400 can be positioned to engage valve tissue 20, 22 as part of any suitable valve repair system (e.g., any valve repair system disclosed in the present application).

Referring now to FIG. 21, the device 400 can include a coaption portion 404 and an anchor portion 406, the anchor portion 406 including a plurality of anchors 408. The coaption portion 404 includes a coaption or spacer member 410. The anchor portion 406 includes a plurality of paddles 420 (e.g., two in the illustrated embodiment), and a plurality of clasps 430 (e.g., two in the illustrated embodiment). A first or proximal collar 411, and a second collar or cap 414 are used to move the coaption portion 404 and the anchor portion 406 relative to one another.

As shown in FIG. 23, first connection portions 425 of the anchors 408 can be coupled to and extend from a first portion 417 of the coaption or spacer member 410, and second connection portions 421 of the anchors 408 can be coupled to the first collar 414. The proximal collar 411 can be coupled to a second portion 419 of the coaption member 410.

The coaption member 410 and the anchors 408 can be coupled together in various ways. For example, as shown in the illustrated embodiment, the coaption member 410 and the anchors 408 can be coupled together by integrally forming the coaption member 410 and the anchors 408 as a single, unitary component. This can be accomplished, for example, by forming the coaption member 410 and the anchors 408 from a braided or woven material, such as braided or woven nitinol wire. In other embodiments, the coaption member 410 and the anchors 408 can be coupled together by welding, fasteners, adhesive, joint connections, sutures, friction fittings, swaging, and/or other means for coupling.

Referring now to FIG. 22, the anchors 408 can comprise first portions or outer paddles 420 and second portions or inner paddles 422 separated by joint portions 423. In this manner, the anchors 408 are configured similar to legs in that the inner paddles 422 are like upper portions of the legs, the outer paddles 420 are like lower portions of the legs, and the joint portions 423 are like knee portions of the legs. In the illustrated example, the inner paddle portion 422, the outer paddle portion 420, and the joint portion 423 are formed from a continuous strip of fabric, such as a metal fabric.

The anchors 408 can be configured to move between various configurations by axially moving the cap 414 relative to the proximal collar 411 and thus the anchors 408 relative to the coaption member 410 along a longitudinal axis extending between the first or distal and second or proximal portions 417, 419 of the coaption member 410. For example, the anchors 408 can be positioned in a straight configuration by moving the cap 414 away from the coaption member 410. In the straight configuration, the paddle portions are aligned or straight in the direction of the longitudinal axis of the device and the joint portions 423 of the anchors 408 are adjacent the longitudinal axis of the coaption member 410 (e.g., similar to the configuration shown in FIG. 24). From the straight configuration, the anchors 408 can be moved to a fully folded configuration (e.g., similar to the configuration shown in FIG. 25) by moving the cap 414 toward the coaption member 410. Initially as the cap 414 moves toward the coaption member 410, the anchors 408 bend at the joint portions 423, 425, 421 and the joint portions 423 move radially outward relative to the longitudinal axis of the coaption member 410 and axially toward the first portion 414 of the coaption member 410, as shown in FIGS. 22-23. As the cap 414 continues to move toward the coaption member 410, the joint portions 423 move radially inwardly relative to the longitudinal axis of the coaption member 410 and axially toward the proximal portion 419 of the coaption member 410, as shown in FIG. 21.

Figure 26:
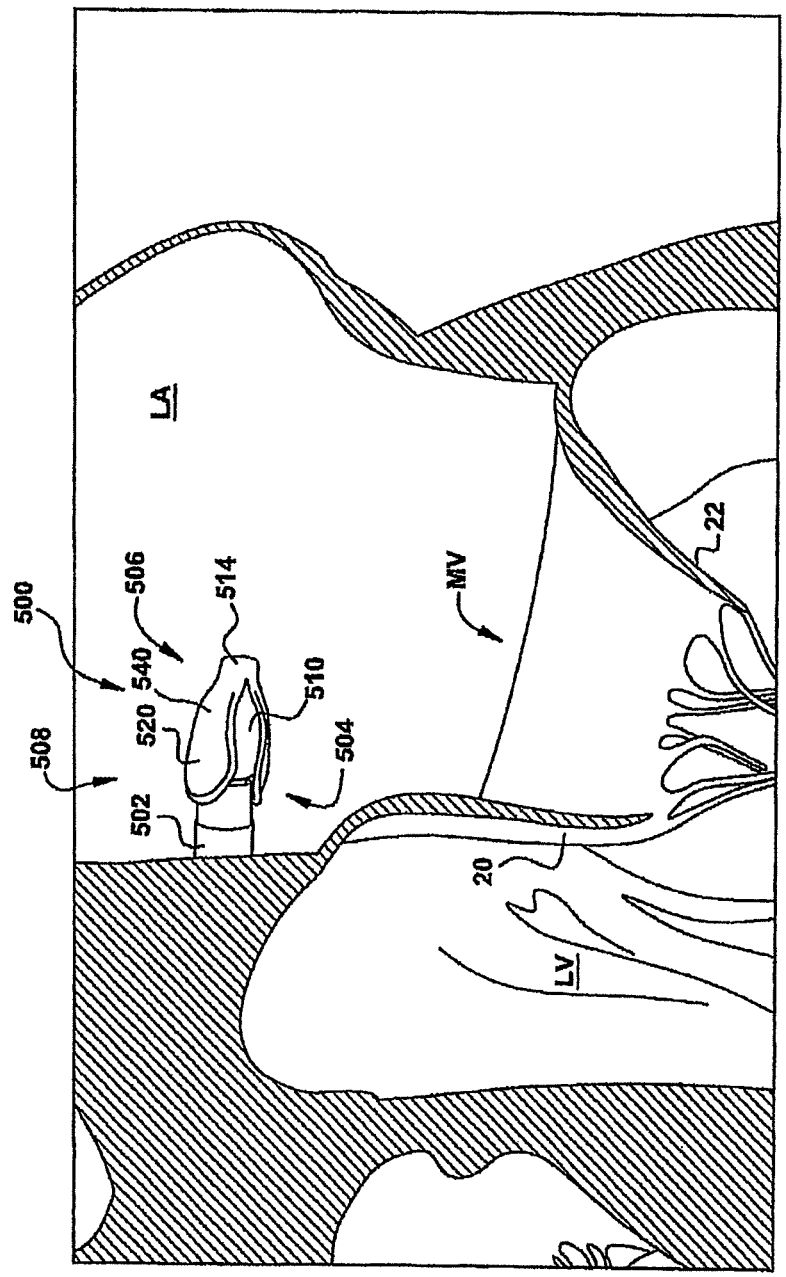

In some embodiments, an angle between the inner paddles 422 of the anchors 408 and the coaption member 410 can be approximately 180 degrees when the anchors 408 are in the straight configuration (see, e.g., similar to the position illustrated by FIG. 24), and the angle between the inner paddles 422 of the anchors 408 and the coaption member 410 can be approximately 0 degrees when the anchors 408 are in the fully folded configuration (See, e.g. similar to the position illustrated by FIG. 26). The anchors 408 can be positioned in various partially folded configurations such that the angle between the inner paddles 422 of the anchors 408 and the coaption member 410 can be approximately 10-170 degrees or approximately 45-135 degrees.

In one exemplary embodiment, anchors of a deployed or implanted device can be positioned such that the angle between the inner paddles 422 of the anchors 408 and the coaption member 410 can be approximately 0-45 degrees, such as approximately 0-30 degrees, such as approximately 0-15 degrees. In some exemplary embodiments, the anchors of the deployed or implanted device are partially open such that the angle between the inner paddles 422 of the anchors 408 and the coaption member 410 can be at least 5 degrees, at least 10 degrees, at least 15 degrees, at least 20 degrees, such as at least 25 degrees.

Configuring the prosthetic device 400 such that the anchors 408 can extend to a straight or approximately straight configuration (e.g. approximately 120-180 degrees relative to the coaption member 410) can provide several advantages. For example, this can reduce the radial crimp profile of the prosthetic device 400. It can also make it easier to grasp the native leaflets by providing a larger opening in which to grasp the native leaflets. Additionally, the relatively narrow, straight configuration can prevent or reduce the likelihood that the prosthetic device 400 will become entangled in native anatomy (e.g., chordae tendineae) when positioning and/or retrieving the prosthetic device 400 into the delivery apparatus.

Configuring the prosthetic device 400 such that the deployed anchors 408 can be in an open configuration (e.g. approximately 5-45 degrees relative to the coaption member 410 or at least 5 degrees, at least 10 degrees, at least 15 degrees, at least 20 degrees, such as at least 25 degrees) can provide several advantages. For example, the anchors can place less stress on the native valve leaflets, especially in cases where there is a wide gap between the valve leaflets. This benefit can be enhanced by allowing the anchors to open and close with the native valve, either by movement or flexing of the anchors. In some exemplary embodiments, the device is deployed with the anchors 408 fully closed (e.g. about 0 degrees relative to the coaption member 410) and the anchors are allowed to open and close with the native valve, either by movement or flexing of the anchors. In some exemplary embodiments, the device is deployed with the anchors 408 partially open (e.g. at least 5 degrees, at least 10 degrees, at least 15 degrees, at least 20 degrees, such as at least 25 degrees relative to the coaption member 410) and the anchors are allowed to further open and return to the deployed (partially open) configuration when the native valve closes, either by movement or flexing of the anchors.

Referring again to FIG. 22 the clasps 430 can comprise attachment or fixed portions 432 and arm or moveable portions 434. The attachment or fixed portions 432 can be coupled to the inner paddles 422 of the anchors 408 in various ways such as with sutures, adhesive, fasteners, welding, stitching, swaging, friction fit and/or other means for coupling.

The moveable portions 434 can pivot relative to the fixed portions 432 between an open configuration (e.g., FIG. 22) and a closed configuration (FIGS. 21 and 23). In some embodiments, the clasps 430 can be biased to the closed configuration. In the open configuration, the fixed portions 432 and the moveable portions 434 pivot away from each other such that native leaflets can be positioned between the fixed portions 432 and the moveable portions 434. In the closed configuration, the fixed portions 432 and the moveable portions 434 pivot toward each other, thereby clamping the native leaflets between the fixed portions 432 and the moveable portions 434.

Figure 21A:
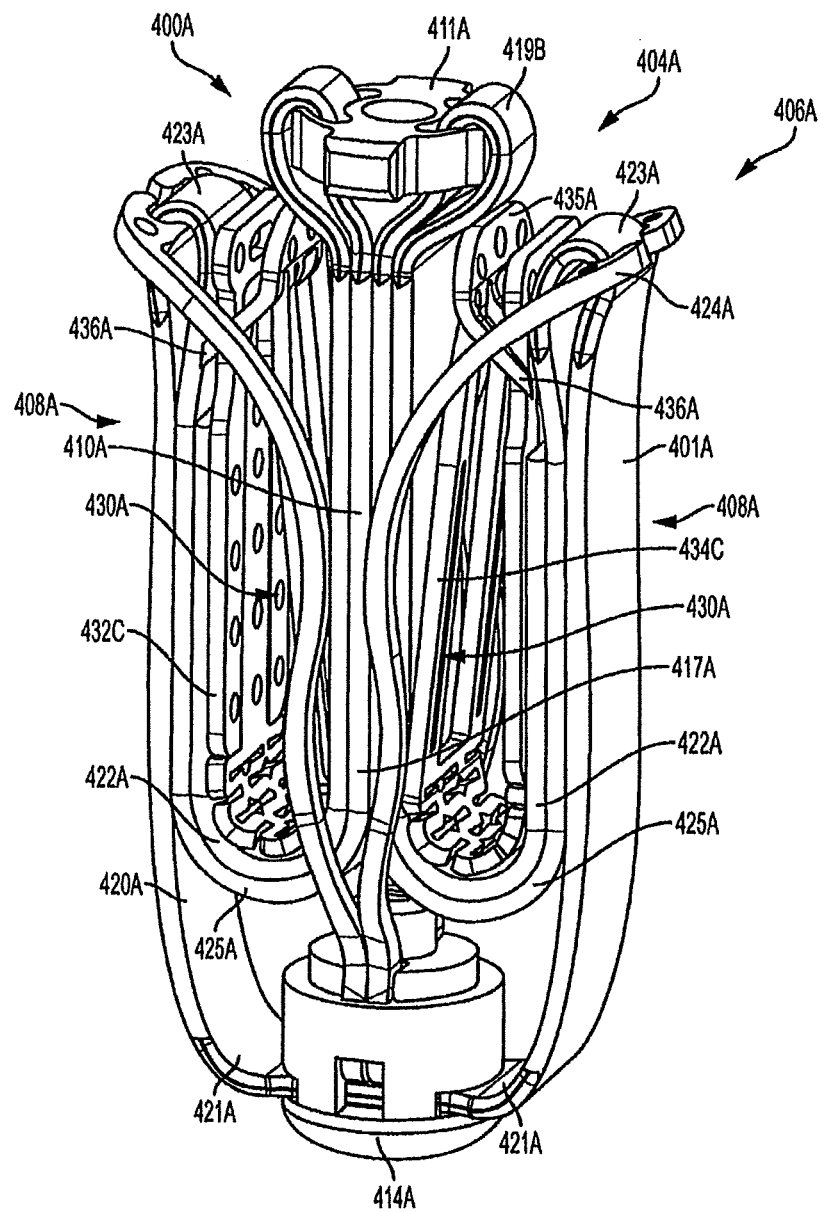
FIG. 21A shows an exemplary embodiment of an implantable prosthetic device.

Referring now to FIG. 21A, an exemplary embodiment of an implantable prosthetic device 400A is shown. The device 400A can include any other features for an implantable prosthetic device discussed in the present application, and the device 400A can be positioned to engage valve tissue 20, 22 as part of any suitable valve repair system (e.g., any valve repair system disclosed in the present application).

The prosthetic device 400A can include a coaption portion 404A and an anchor portion 406A, the anchor portion 406A including a plurality of anchors 408A. The coaption portion 404A includes a coaption member or spacer 410A. The anchor portion 406A includes a plurality of paddles 420A (e.g., two in the illustrated embodiment), and a plurality of clasps 430A (e.g., two in the illustrated embodiment). A first or proximal collar 411A, and a second collar or cap 414A are used to move the coaption portion 404A and the anchor portion 406A relative to one another.

The coaption member 410A extends from a proximal portion 419A assembled to the collar 411A to a distal portion 417A that connects to the anchors 408A. The coaption member 410A and the anchors 408A can be coupled together in various ways. For example, as shown in the illustrated embodiment, the coaption member 410A and the anchors 408A can be coupled together by integrally forming the coaption member 410A and the anchors 408A as a single, unitary component. This can be accomplished, for example, by forming the coaption member 410A and the anchors 408A from a continuous strip 401A of a braided or woven material, such as braided or woven nitinol wire.

The anchors 408A are attached to the coaption member 410A by hinge portions 425A and to the cap 414A by hinge portions 421A. The anchors 408A can comprise first portions or outer paddles 420A and second portions or inner paddles 422A separated by joint portions 423A. The joint portions 423A are attached to paddle frames 424A that are hingeably attached to the cap 414A. In this manner, the anchors 408A are configured similar to legs in that the inner paddles 422A are like upper portions of the legs, the outer paddles 420A are like lower portions of the legs, and the joint portions 423A are like knee portions of the legs. In the illustrated example, the inner paddle portion 422A, the outer paddle portion 420A, and the joint portion 423A are formed from the continuous strip of fabric 401A, such as a metal fabric.

The anchors 408A can be configured to move between various configurations by axially moving the cap 414A relative to the proximal collar 411A and thus the anchors 408A relative to the coaption member 410A along a longitudinal axis extending between the cap 414A and the proximal collar 411A. For example, the anchors 408 can be positioned in a straight configuration (see for example, FIGS. 8, 9) by moving the cap 414A away from the coaption member 410A. In the straight configuration, the paddle portions 420A, 422A are aligned or straight in the direction of the longitudinal axis of the device and the joint portions 423A of the anchors 408A are adjacent the longitudinal axis of the coaption member 410A. From the straight configuration, the anchors 408 can be moved to a fully folded configuration (e.g., FIG. 10) by moving the cap 414A toward the coaption member 410A. Initially, as the cap 414A moves toward the coaption member 410A, the anchors 408A bend at joint portions 421A, 423A, 425A, and the joint portions 423A move radially outwardly relative to the longitudinal axis of the device 400A and axially toward the distal portion 417A of the coaption member 410A. As the cap 414A continues to move toward the coaption member 410A, the joint portions 423A move radially inwardly relative to the longitudinal axis of the device 400A and axially toward the proximal portion 419A of the coaption member 410A.

In some embodiments, an angle between the inner paddles 422A of the anchors 408A and the coaption member 410A can be approximately 180 degrees when the anchors 408A are in the straight configuration, and the angle between the inner paddles 422A of the anchors 408A and the coaption member 410A can be approximately 0 degrees when the anchors 408A are in the fully folded configuration (see FIG. 21A). The anchors 408A can be positioned in various partially folded configurations such that the angle between the inner paddles 422A of the anchors 408A and the coaption member 410A can be approximately 10-170 degrees or approximately 45-135 degrees.

Configuring the prosthetic device 400A such that the anchors 408A can extend to a straight or approximately straight configuration (e.g. approximately 120-180 degrees relative to the coaption member 410A) can provide several advantages. For example, this can reduce the radial crimp profile of the prosthetic device 400A. It can also make it easier to grasp the native leaflets by providing a larger opening in which to grasp the native leaflets. Additionally, the relatively narrow, straight configuration can prevent or reduce the likelihood that the prosthetic device 400A will become entangled in native anatomy (e.g., chordae tendineae) when positioning and/or retrieving the prosthetic device 400A into the delivery apparatus.

In one exemplary embodiment, anchors of a deployed or implanted device can be positioned such that the angle between the inner paddles 422A of the anchors 408A and the coaption member 410A can be approximately 0-45 degrees, such as approximately 0-30 degrees, such as approximately 0-15 degrees. In some exemplary embodiments, the anchors of the deployed or implanted device are partially open such that the angle between the inner paddles 422A of the anchors 408A and the coaption member 410A can be at least 5 degrees, at least 10 degrees, at least 15 degrees, at least 20 degrees, such as at least 25 degrees.

Configuring the prosthetic device 400A such that the deployed anchors 408A can be in an open configuration (e.g. approximately 5-45 degrees relative to the coaption member 410A or at least 5 degrees, at least 10 degrees, at least 15 degrees, at least 20 degrees, such as at least 25 degrees) can provide several advantages. For example, the anchors can place less stress on the native valve leaflets, especially in cases where there is a wide gap between the valve leaflets. This benefit can be enhanced by allowing the anchors to open and close with the native valve, either by movement or flexing of the anchors. In some exemplary embodiments, the device is deployed with the anchors 408 fully closed (e.g. about 0 degrees relative to the coaption member 410A) and the anchors are allowed to open and close with the native valve, either by movement or flexing of the anchors. In some exemplary embodiments, the device is deployed with the anchors 408 partially open (e.g. at least 5 degrees, at least 10 degrees, at least 15 degrees, at least 20 degrees, such as at least 25 degrees relative to the coaption member 410) and the anchors are allowed to further open and return to the deployed (partially open) configuration when the native valve closes, either by movement or flexing of the anchors.

The clasps 430A can comprise attachment or fixed portions 432C and arm or moveable portions 434C. The attachment or fixed portions 432C can be coupled to the inner paddles 422A of the anchors 408A in various ways such as with sutures, adhesive, fasteners, welding, stitching, swaging, friction fit and/or other means for coupling. The clasps 430A are similar to the clasps 430.

Figure 53A:
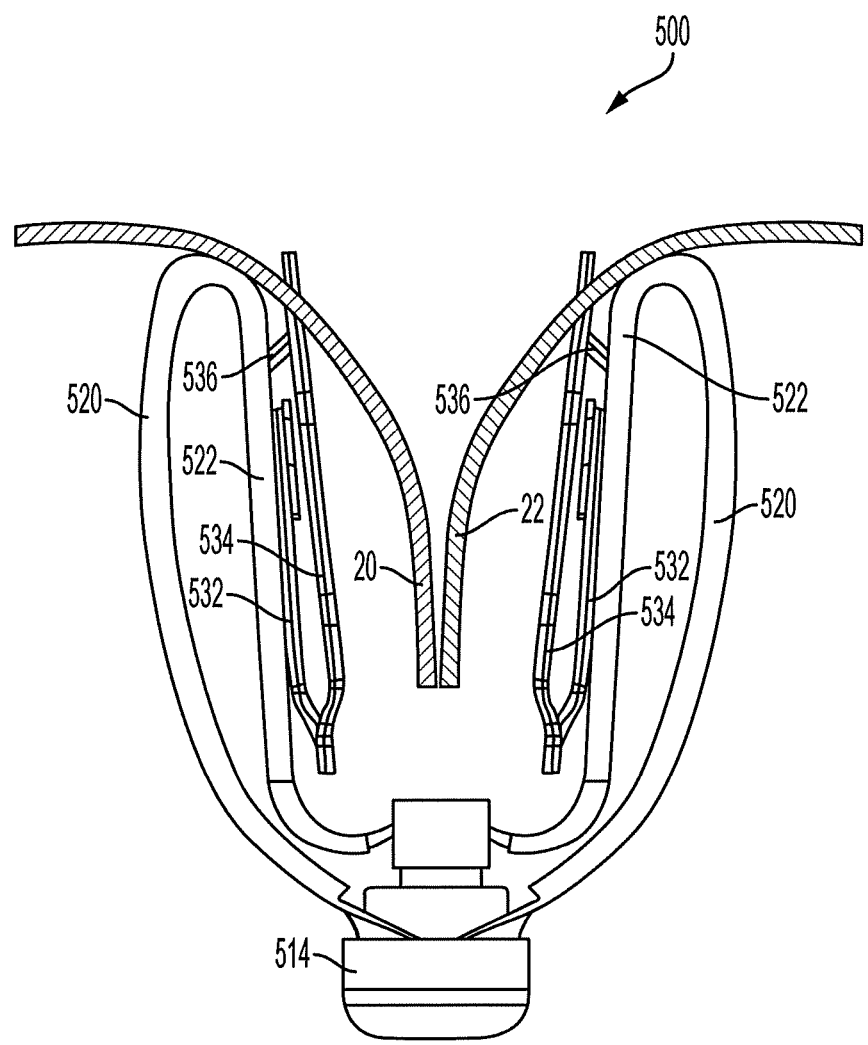
FIG. 53A shows a schematic view of a path of mitral valve leaflets along each side of an exemplary embodiment of a mitral valve repair device having clasps in a closed position.

The moveable portions 434C can pivot relative to the fixed portions 432C between an open configuration (e.g., FIG. 54A) and a closed configuration (FIG. 53A). In some embodiments, the clasps 430A can be biased to the closed configuration. In the open configuration, the fixed portions 432C and the moveable portions 434C pivot or flex away from each other such that native leaflets can be positioned between the fixed portions 432C and the moveable portions 434C. In the closed configuration, the fixed portions 432C and the moveable portions 434C pivot or flex toward each other, thereby clamping the native leaflets between the fixed portions 432C and the moveable portions 434C.

The strip 401A is attached to the collar 411A, cap 414A, paddle frames 424A, clasps 430A to form both the coaption portion 404A and the anchor portion 406A of the device 400A. In the illustrated embodiment, the coaption member 410A, hinge portions 421A, 423A, 425A, outer paddles 420A, and inner paddles 422A are formed from the continuous strip 401A. The continuous strip 401A may be a single layer of material or may include two or more layers. In certain embodiments, portions of the device 400A have a single layer of the strip of material 401A and other portions are formed from multiple overlapping or overlying layers of the strip of material 401A. For example, FIG. 21A shows the coaption member 410A and inner paddles 422A formed from multiple overlapping layers of the strip of material 401A. The single continuous strip of material 401A can start and end in various locations of the device 400A. The ends of the strip of material 401A can be in the same location or different locations of the device 400A. For example, in the illustrated embodiment of FIG. 21A, the strip of material begins and ends in the location of the inner paddles 422A.

Referring now to FIGS. 24-35, the implantable device 500 is shown being delivered and implanted within the native mitral valve MV of the heart H. As described above, the device 500 has an optional covering 540 over the coaption element 510, clasps 530, inner paddles 522 and/or the outer paddles 520. The device 500 is deployed from a delivery sheath 502 and includes a coaption portion 504 and an anchor portion 506 including a plurality of anchors 508 (e.g., two in the illustrated embodiment). The coaption portion 504 of the device includes a coaption element 510 for implantation between the leaflets 20, 22 of the native mitral valve MV that is slidably attached to an actuation wire or shaft 512.

The anchors 508 of the device 500 include outer paddles 520 and inner paddles 522 that are flexibly connected to the cap 514 and the coaption element 510. The actuation wire 512 extends through a capture mechanism 503 (see FIG. 30), delivery sheath 502, and the coaption element 510 to the cap 514 connected to the anchor portion 506. Extending and retracting the actuation wire 512 increases and decreases the spacing between the coaption element 510 and the cap 514, respectively. In the example illustrated by FIGS. 24-35, the pair of inner and outer paddles 522, 520 are moved in unison, rather than independently, by a single actuation wire 512. Also, the positions of the clasps 530 are dependent on the positions of the paddles 522, 520. For example, referring to FIG. 34 closing the paddles 522, 520 also closes the clasps. In one exemplary embodiment, the device 500 can be made to have the paddles 520, 522 be independently controllable in the same manner as the FIG. 11A embodiment.

Fingers of the capture mechanism 503 removably attach the collar 511 to the delivery sheath 502. The collar 511 and the coaption element 510 slide along the actuation wire 512 during actuation to open and close the anchors 508 of the anchor portion 506. In some embodiments, the capture mechanism 503 is held closed around the collar 511 by the actuation wire 512, such that removal of the actuation wire 512 allows the fingers of the capture mechanism 503 to open, releasing the collar 511, and thus the coaption element 510.

The coaption element 510 and paddles 520, 522 can be formed from a flexible material that may be a metal fabric, such as a mesh, woven, braided, or formed in any other suitable way or a laser cut or otherwise cut flexible material. The flexible material may be cloth, shape-memory alloy wire—such as Nitinol—to provide shape-setting capability, or any other flexible material suitable for implantation in the human body.

The barbed clasps 530 include a base or fixed arm 532, a moveable arm 534, barbs 536 (see FIG. 30), and a joint portion 538. The fixed arms 532 are attached to the inner paddles 522, with the joint portions 538 disposed proximate the coaption element 510. Sutures (not shown) attach the fixed arms 532 to the inner paddles 522. The fixed arms 532 can be attached to the inner paddles 522 with any suitable means, such as screws or other fasteners, crimped sleeves, mechanical latches or snaps, welding, adhesive, or the like.

The fixed arms 532 remain substantially stationary when the moveable arms 534 are opened to open the barbed clasps 530 and expose the barbs 536. The barbed clasps 530 are opened by applying tension to actuation lines 537 attached to the moveable arms 534, thereby causing the moveable arms 534 to pivot or flex on the joint portions 538.

During implantation, the anchors 508 are opened and closed to grasp the native mitral valve leaflets between the paddles 520, 522 and the coaption element 510. The outer paddles 520 have a wide curved shape that fits around the curved shape of the coaption element 510 to more securely grip the leaflets 20, 22. The curved shape and rounded edges of the outer paddle 520 also prohibits tearing of the leaflet tissue. The barbed clasps 530 further secure the native leaflets by engaging the leaflets with barbs 536 and pinching the leaflets between the moveable and fixed arms 534, 532. The barbs 536 of the barbed clasps 530 increase friction with the leaflets or may partially or completely puncture the leaflets. The actuation lines can be actuated separately so that each barbed clasp 530 can be opened and closed separately. Separate operation allows one leaflet to be grasped at a time, or for the repositioning of a clasp 530 on a leaflet that was insufficiently grasped, without altering a successful grasp on the other leaflet. The barbed clasps 530 can be fully opened and closed when the inner paddle 522 is not closed, thereby allowing leaflets to be grasped in a variety of positions as the particular situation requires.

Figure 24:
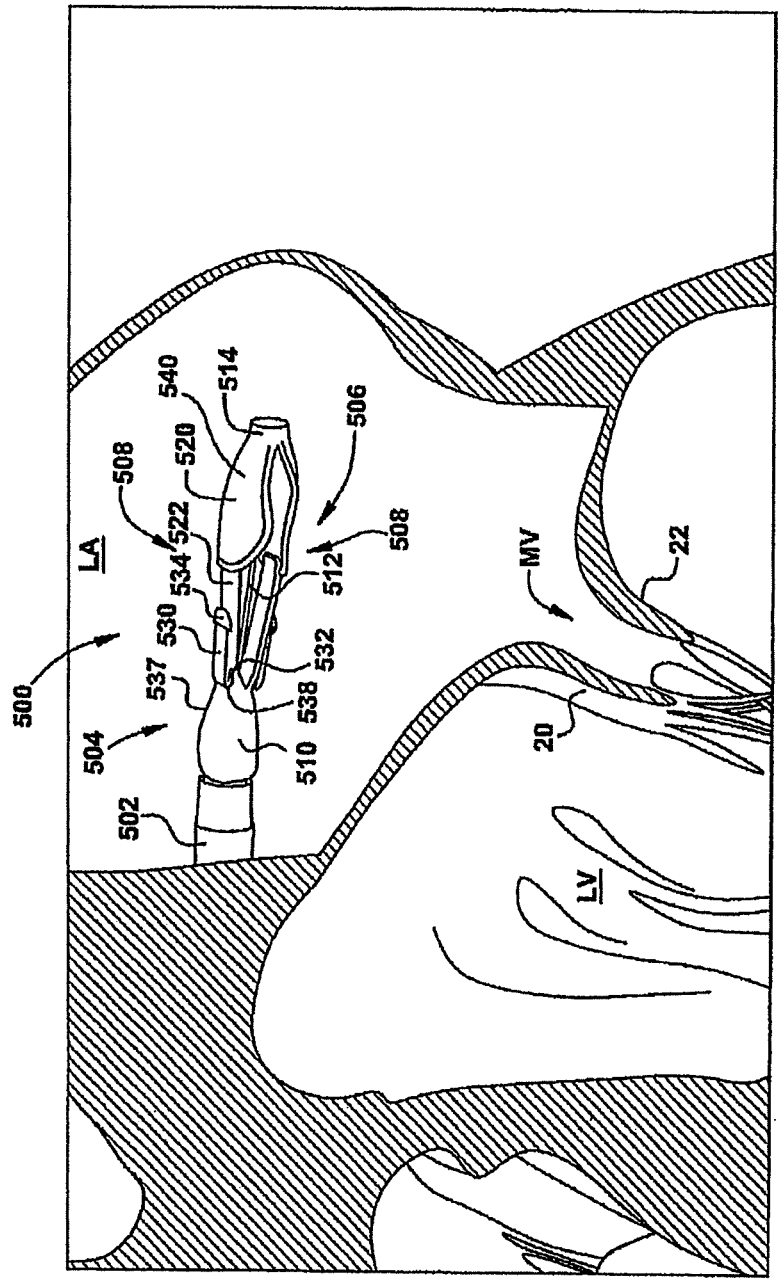
FIGS. 24-35 show an exemplary embodiment of an implantable prosthetic device being delivered and implanted within the native mitral valve.
Figure 25:
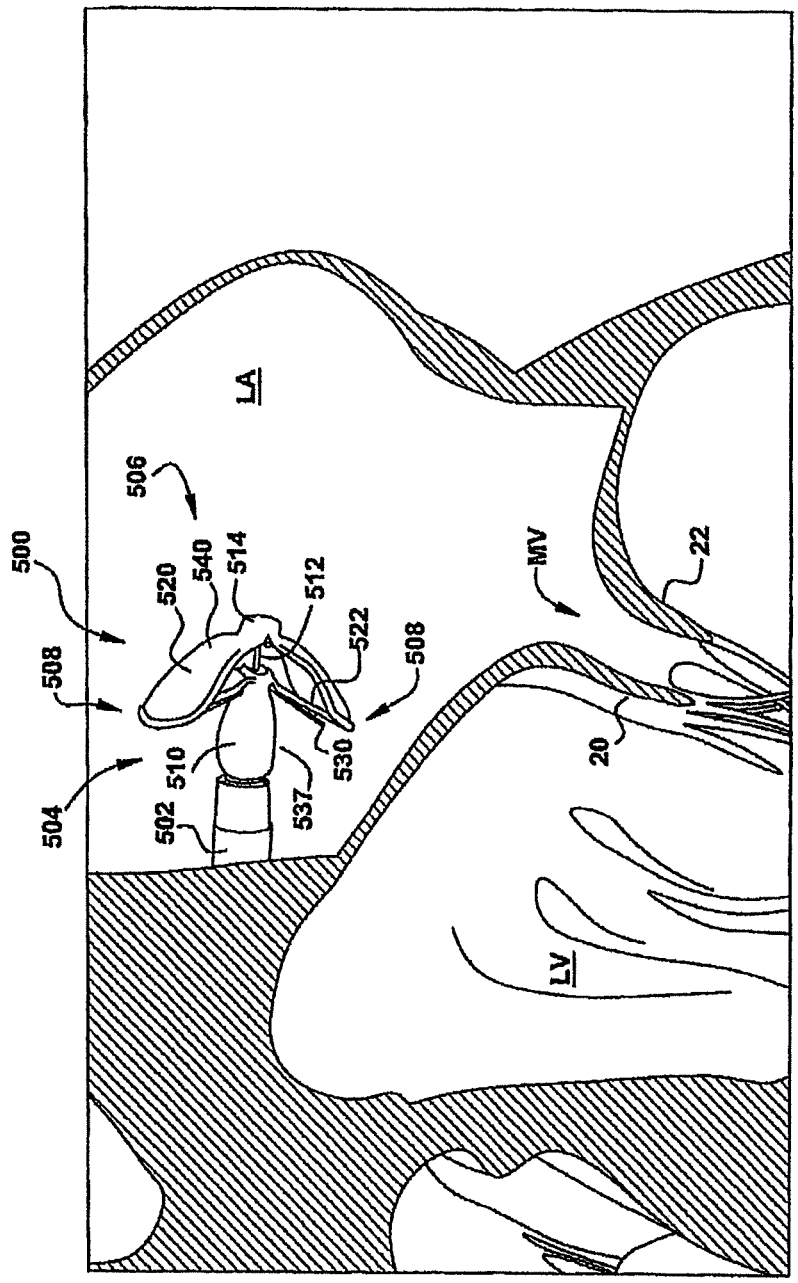
Figure 27:
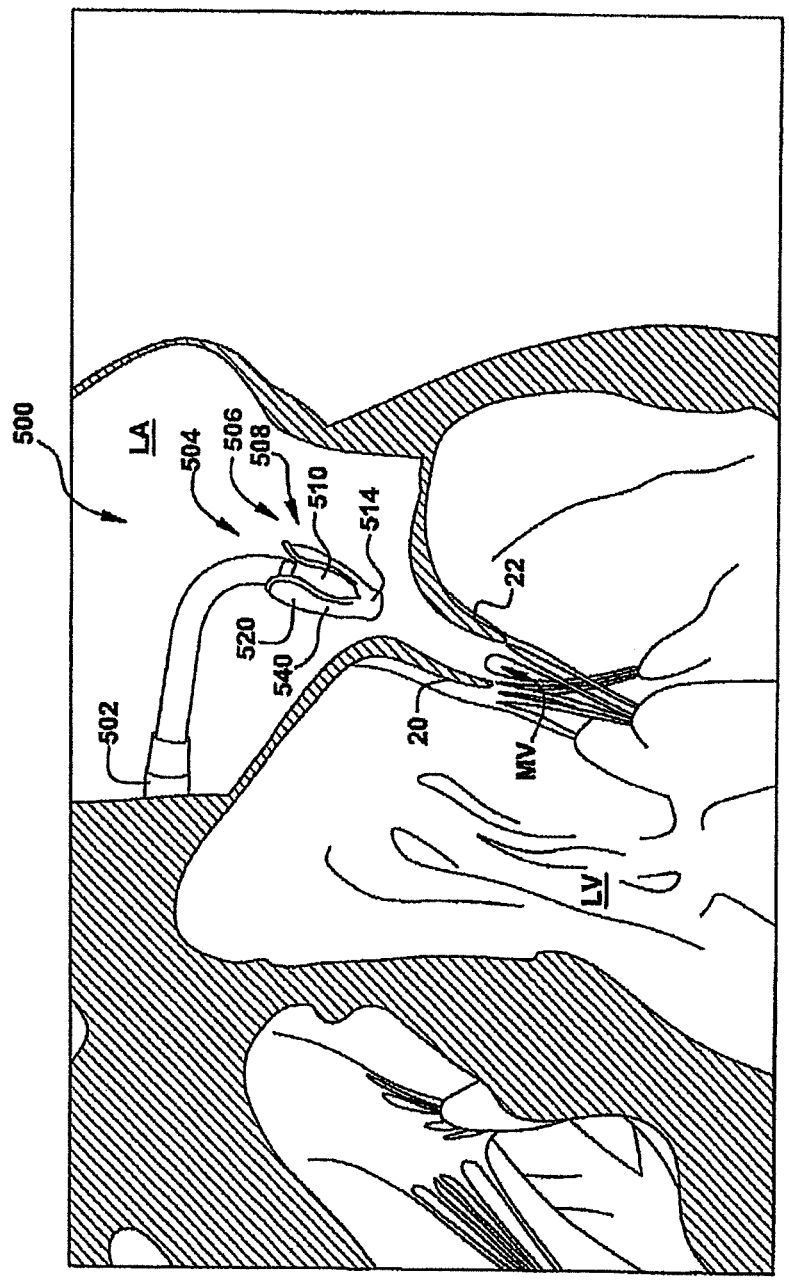
Figure 28:
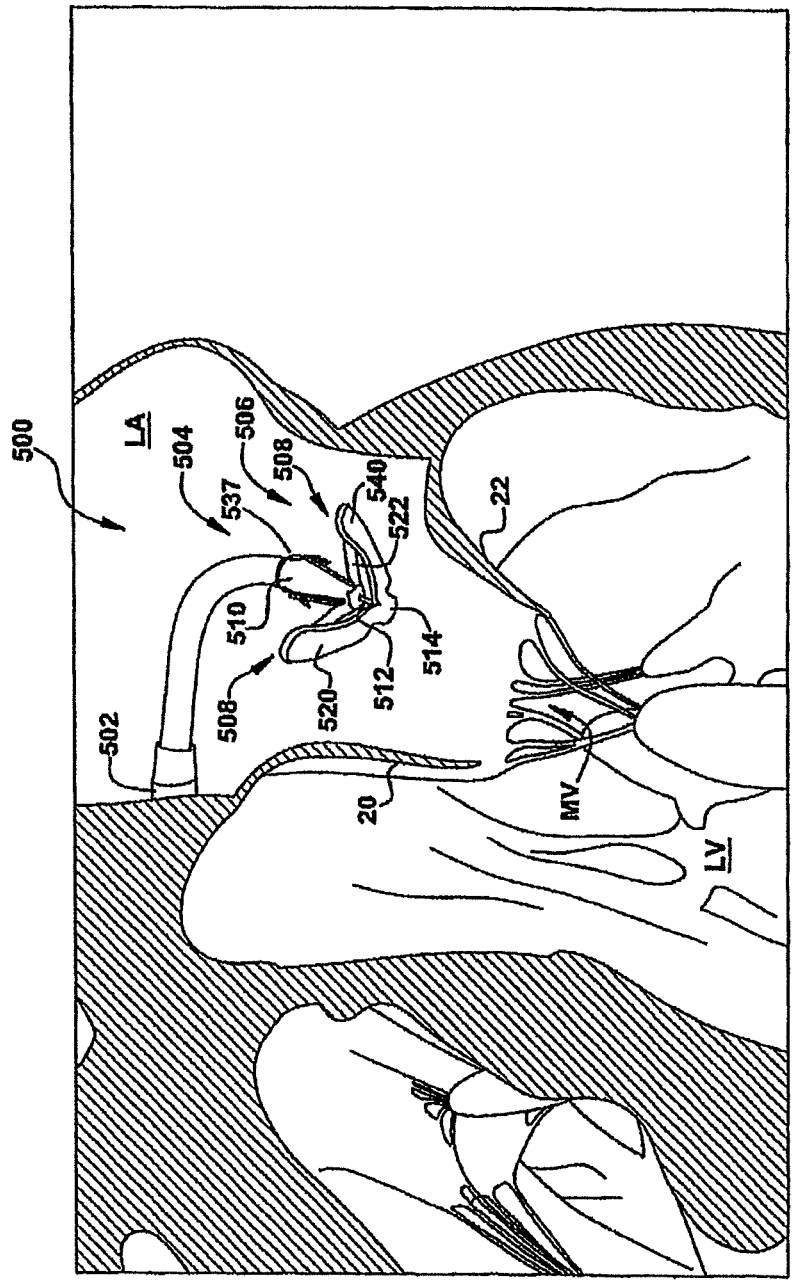
Figure 29:
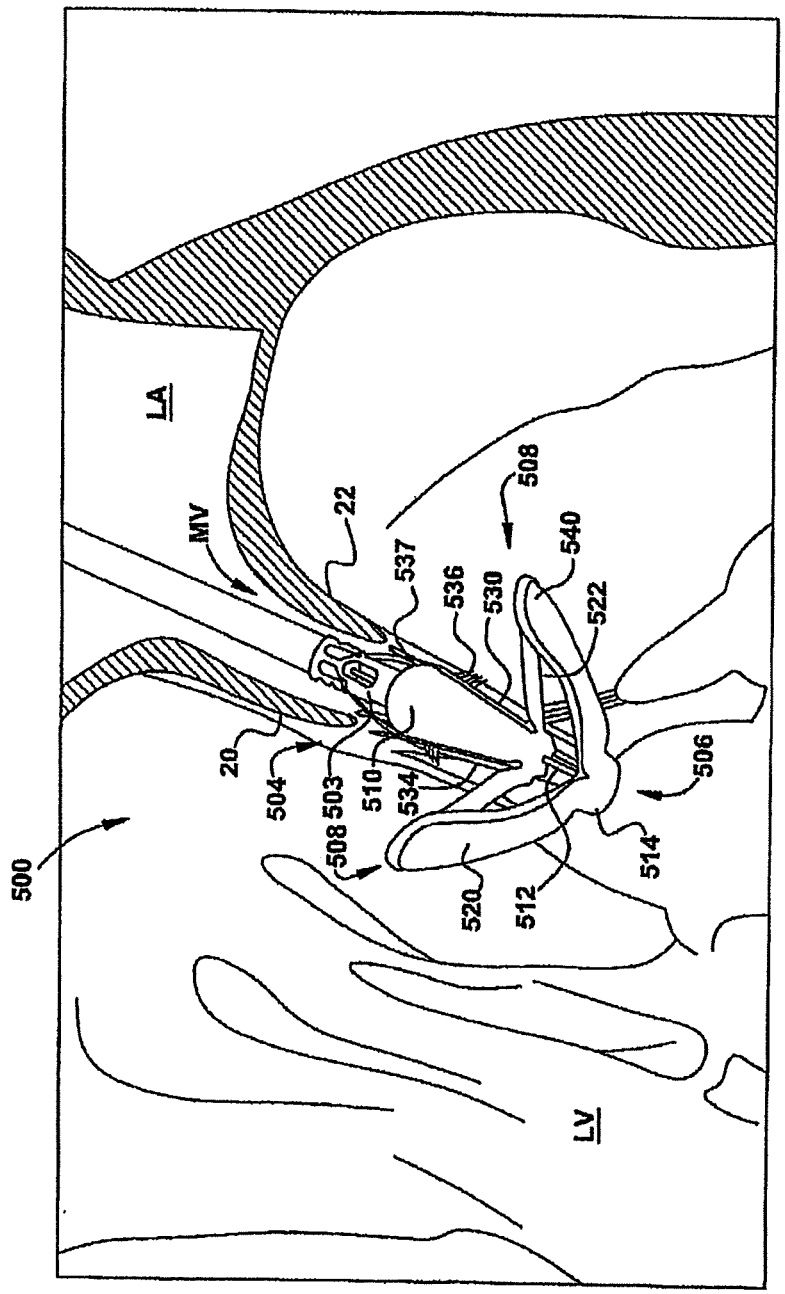
Figure 30:
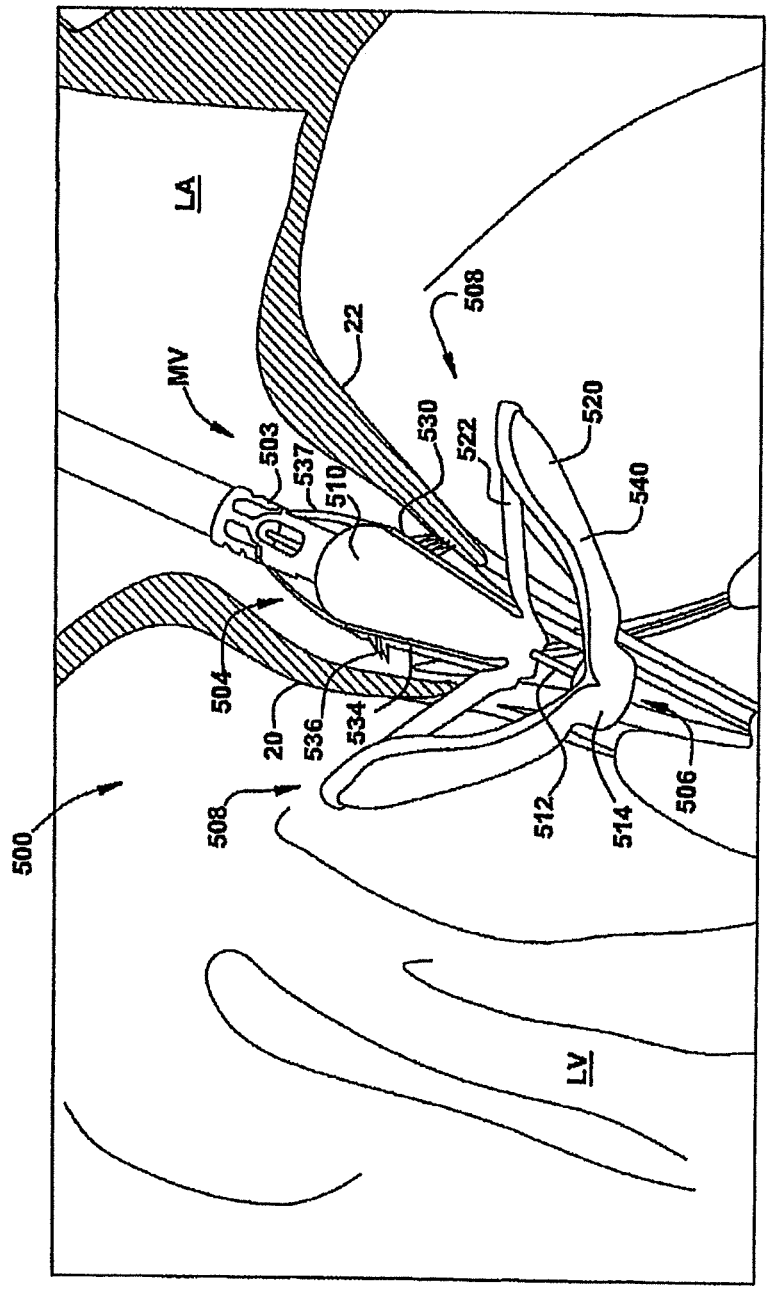
Figure 31:
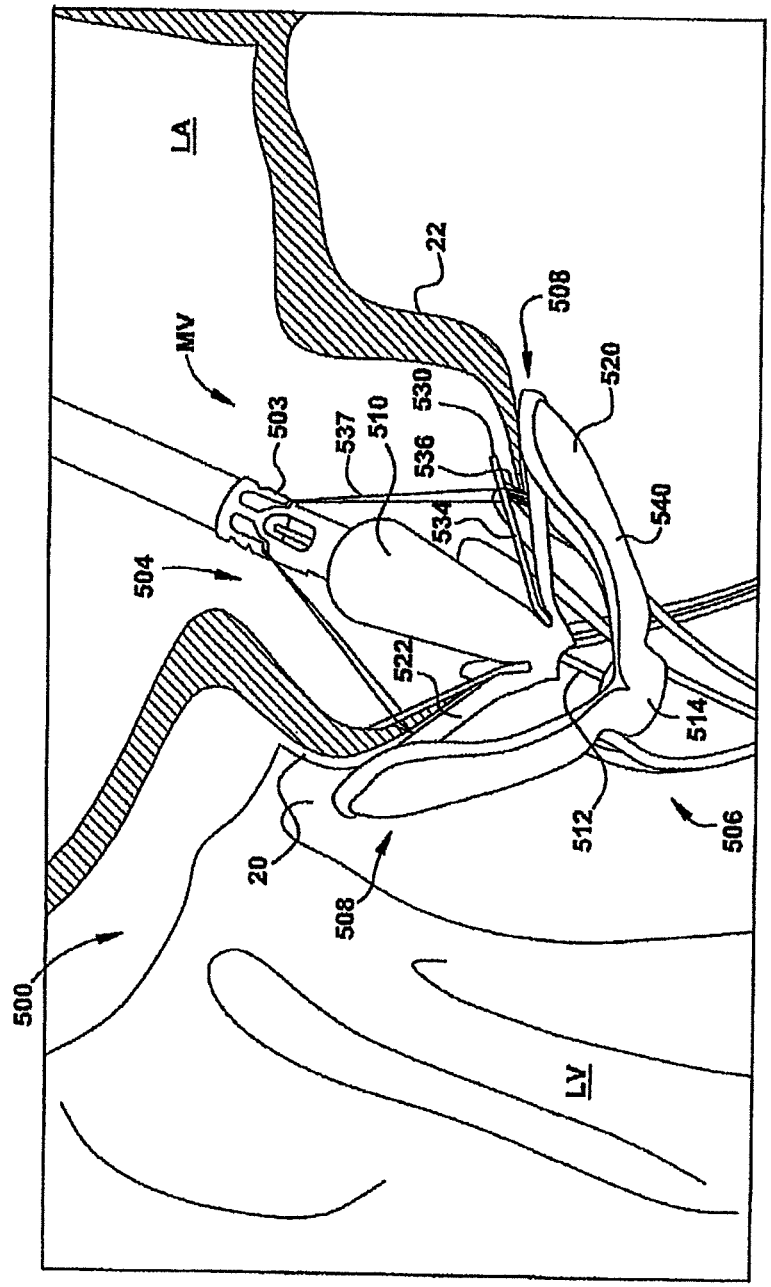
Figure 32:
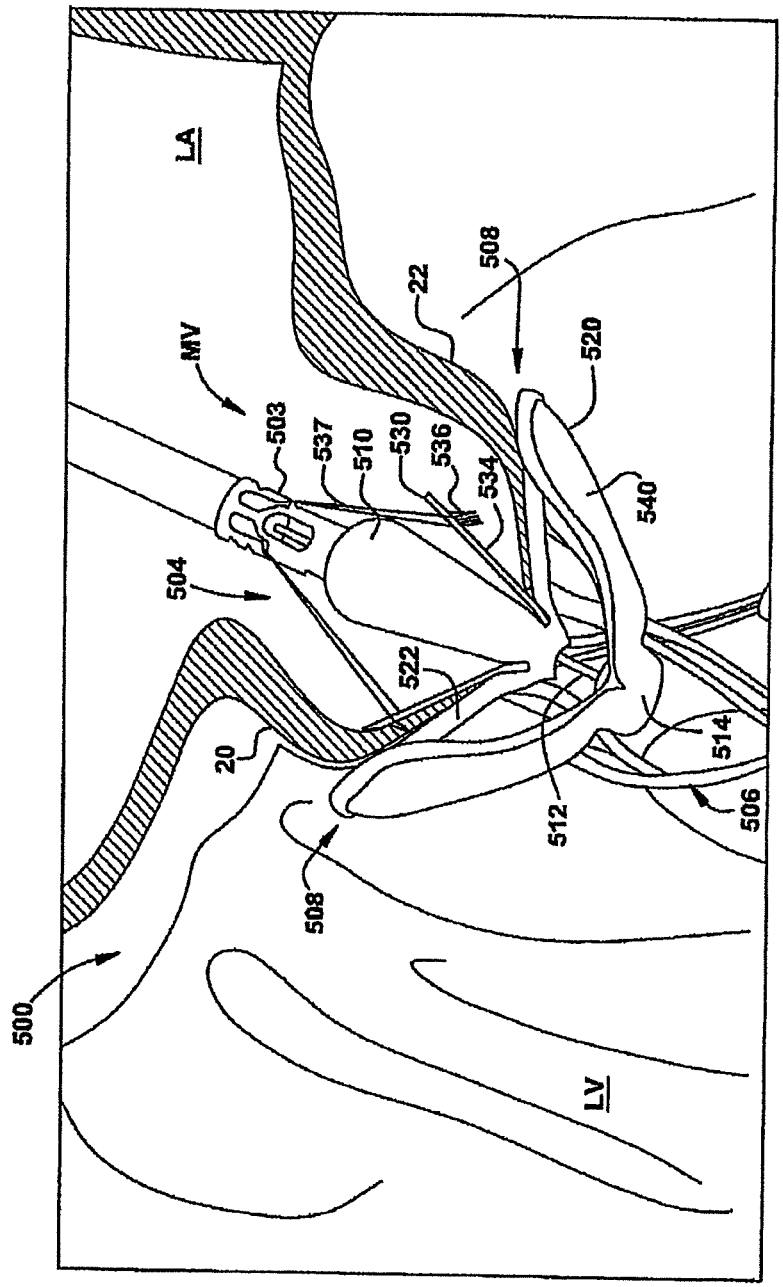
Figure 33:
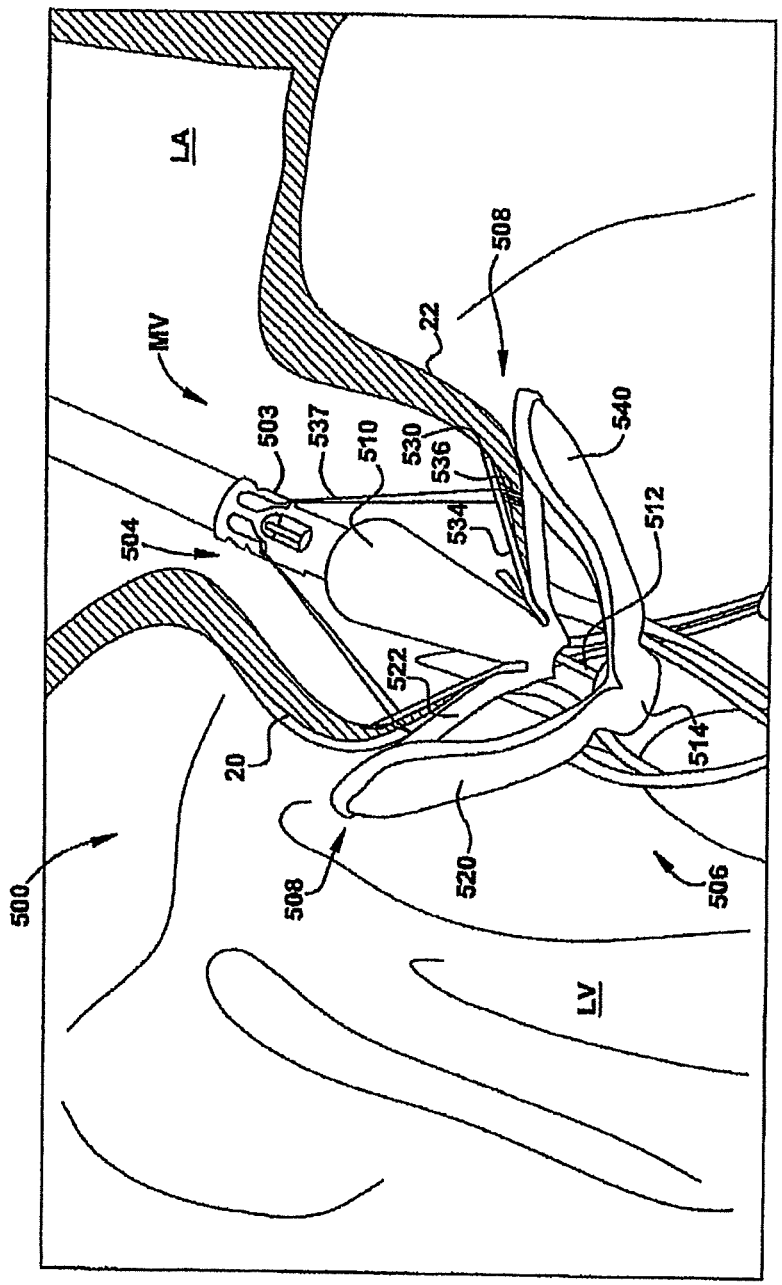
Figure 34:
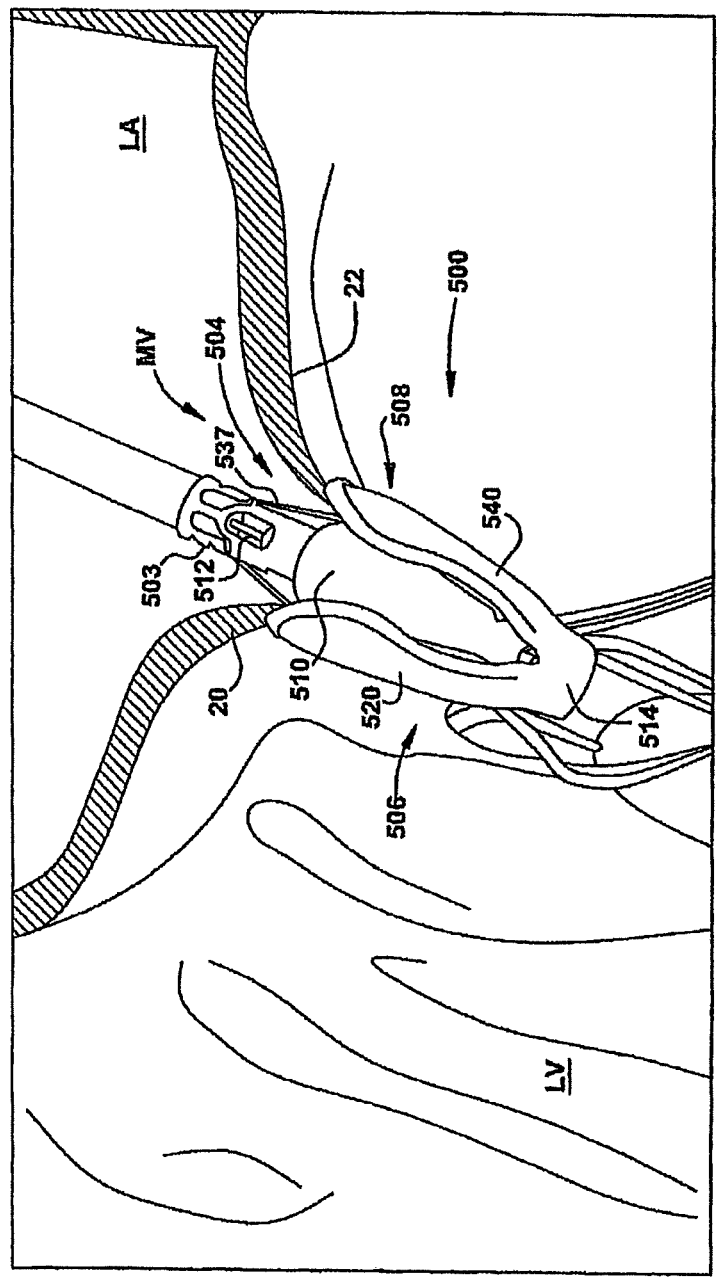
Figure 35:
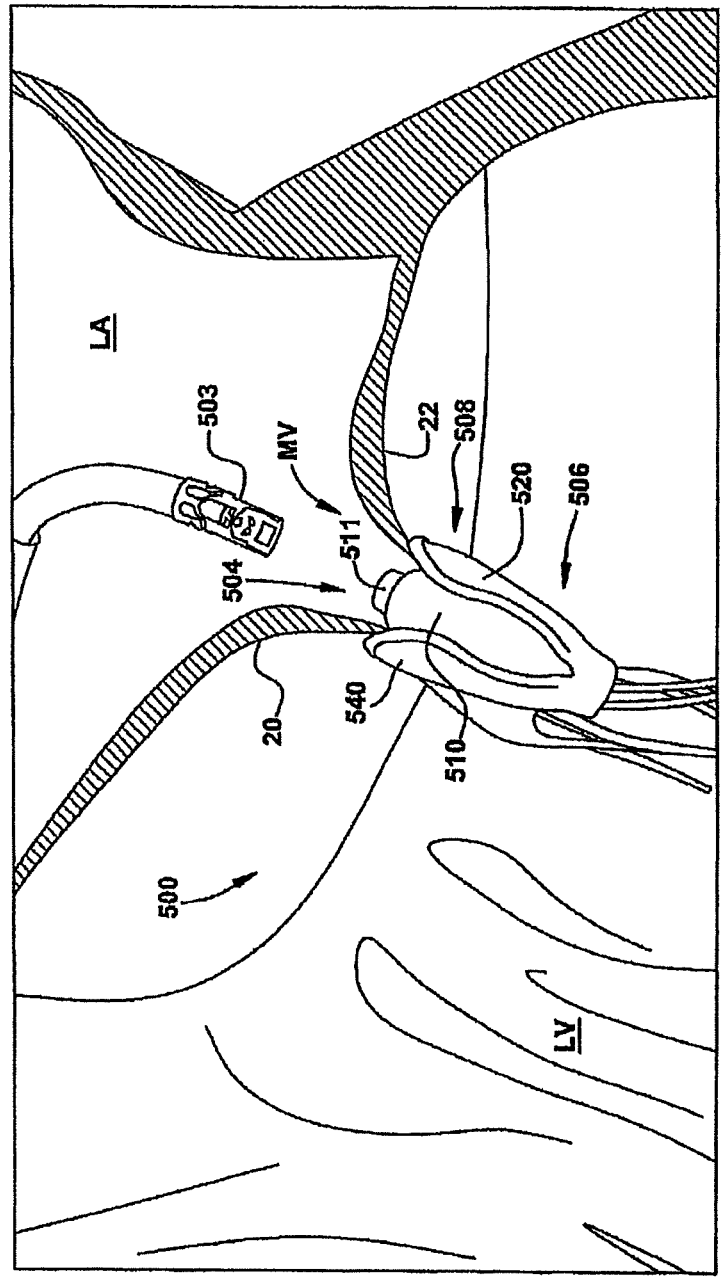

The device 500 can be loaded in the delivery sheath in the fully open position, because the fully open position takes up the least space and allows the smallest catheter to be used (or the largest device 500 to be used for a given catheter size). Referring now to FIG. 24, the delivery sheath is inserted into the left atrium LA through the septum and the device 500 is deployed from the delivery sheath 502 in the fully open condition. The actuation wire 512 is then retracted to move the device 500 into the fully closed condition shown in FIGS. 25-26 and then maneuvered towards the mitral valve MV as shown in FIG. 27. Referring now to FIG. 28, when the device 500 is aligned with the mitral valve MV, the actuation wire 512 is extended to open the paddles 520, 522 into the partially opened position and the actuation lines 537 are retracted to open the barbed clasps 530 to prepare for leaflet grasp. Next, as shown in FIGS. 29-30, the partially open device 500 is inserted through the mitral valve MV until leaflets 20, 22 are properly positioned in between the inner paddles 522 and the coaption element 510 and inside the open barbed clasps 530. FIG. 31 shows the device 500 with both clasps 530 closed, though the barbs 536 of one clasp 530 missed one of the leaflets 22. As can be seen in FIGS. 31-33, the out of position clasp 530 is opened and closed again to properly grasp the missed leaflet 22. When both leaflets 20, 22 are grasped properly, the actuation wire 512 is retracted to move the device 500 into the fully closed position shown in FIG. 34. With the device 500 fully implanted in the native mitral valve MV, the actuation wire 512 is withdrawn to release the capture mechanism 503 from the proximal collar 511. However, in other exemplary embodiments, the device is moved to a partially open position and released in the partially open position. Once deployed, the device 500 may be maintained in the fully closed position or a partially open deployed position Referring now to FIGS. 36-38, an implantable device 500 is shown in various positions and configurations. The implantable device 500 can include any other features for an implantable prosthetic device discussed in the present application, and the device 500 can be positioned to engage valve tissue 20, 22 as part of any suitable valve repair system (e.g., any valve repair system disclosed in the present application).

The implantable device 500 has a proximal or attachment portion 505, a coaption element 510, inner anchor portions or inner paddles 522, outer anchor portions or outer paddles 520, anchor extension members or biasing members 524, and a distal portion 507. The inner paddles 522 are jointably attached between the coaption element 510 and the outer paddles 520. The outer paddles 520 are flexibly attached between the inner paddles 522 and the distal portion 507. The biasing members 524 are attached to the cap 514 at the distal portion 507 and extend to the joint portion 523 between the inner and outer paddles 522, 520. In some embodiments, the biasing members 524 are formed of a material that is more rigid and stiff than the material forming the paddles 522, 520 so that the biasing members 524 provide support for the paddles 522, 520. In one exemplary embodiment, the biasing members 524 are resilient enough or have resilient portions that allow the paddles 520, 522 to open and close with the opening and closing of the native valve. In one exemplary embodiment, the inner paddles 522 are stiff, relatively stiff, rigid, have rigid portions and/or are stiffened by a stiffening member or the fixed portion of the clasps 530. The stiffening of the inner paddle facilitates movement to the various different positions shown and described herein. The inner paddle 522, the outer paddle 520, the coaption can all be interconnected as described herein, such that the device 500 is constrained to the movements and positions shown and described herein.

Figure 36:
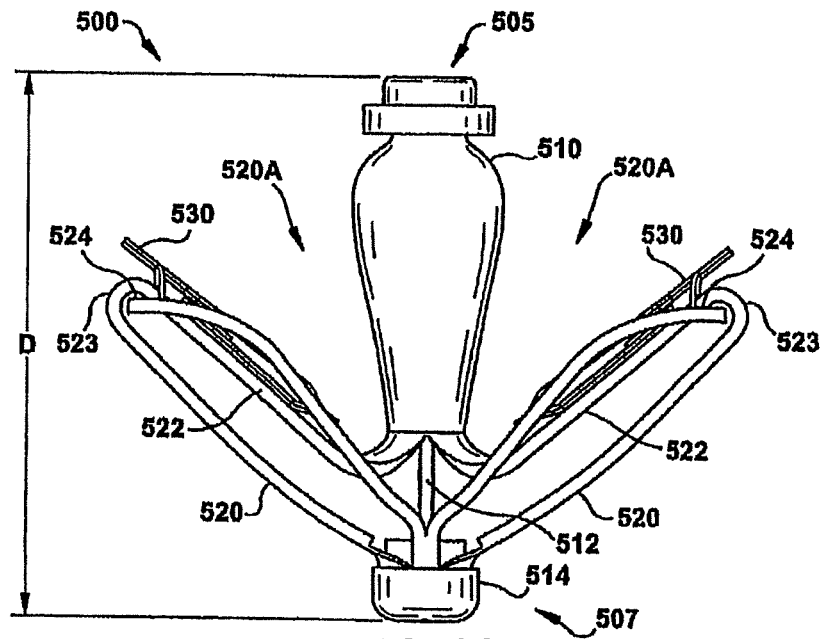
FIG. 36 shows a side view of an exemplary implantable prosthetic device in a partially-open position with barbed clasps in a closed position.
Figure 37:
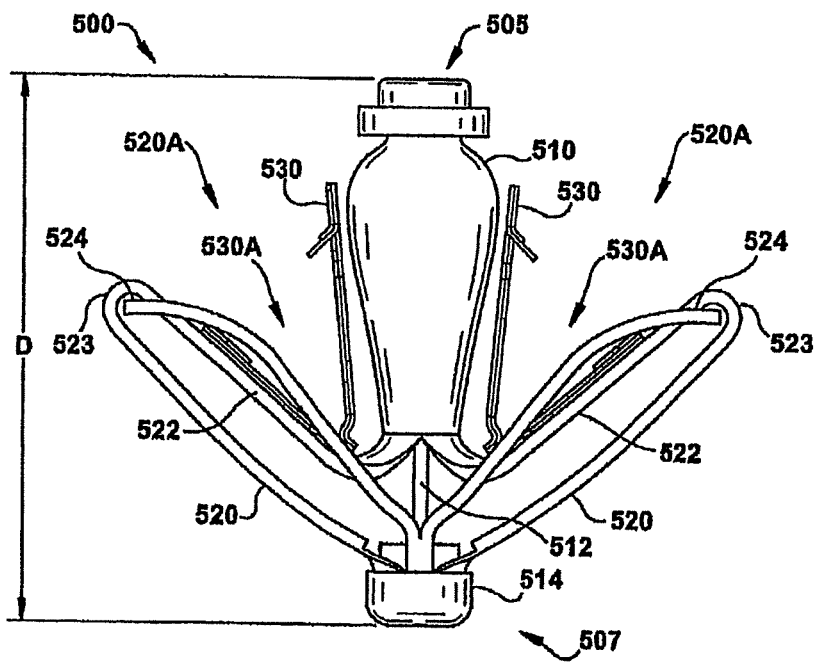
FIG. 37 shows a side view of an exemplary implantable prosthetic device in a partially open position with barbed clasps in an open position.

Referring now to FIGS. 36-37, the device 500 is shown in a partially open position. The device 500 is moved into the partially open position by an actuation wire or shaft 512 that passes through the attachment portion 505 and coaption element 510 and can removably engage the distal portion 507. The actuation wire 512 is extended through the attachment portion 505 such that a distance D between the attachment portion 505 and distal portion 507 increases as the actuation wire 512 is extended. In the example illustrated by FIGS. 36-37, the pair of inner and outer paddles 522, 520 are moved in unison, rather than independently, by a single actuation wire 512. Also, the positions of the clasps 530 are dependent on the positions of the paddles 522, 520. In one exemplary embodiment, the device 500 can be made to have the paddles 520, 522 be independently controllable in the same manner as the FIG. 11A embodiment.

Extending the actuation wire 512 pulls down on the bottom portions of the outer paddles 520 and biasing members 524. The outer paddles 520 and biasing members pull down on the inner paddles 522, where the inner paddles 522 are connected to the outer paddles 520 and the biasing members 524. Because the attachment portion 505 and coaption element 510 are held in place, the inner paddles 522 are caused to pivot or flex in an opening direction. Opening the paddles 522, 520 and biasing members 524 forms a gap 520A between the coaption element 510 and the inner paddle 522 that can receive and grasp the native leaflets 20.

As is described above, some embodiments of the device 500 include clasps or gripping members 530. When the device 500 is partially opened the clasps 530 are exposed. In some embodiments, the closed clasps 530 (FIG. 36) can be opened (FIG. 37), thereby creating a second opening or gap 530A for receiving and capturing the native leaflets 20, 22. The extent of the gap 530A in the clasps 530 is limited to the extent that the inner paddle 522 has spread away from the coaption element 510.

Figure 38:
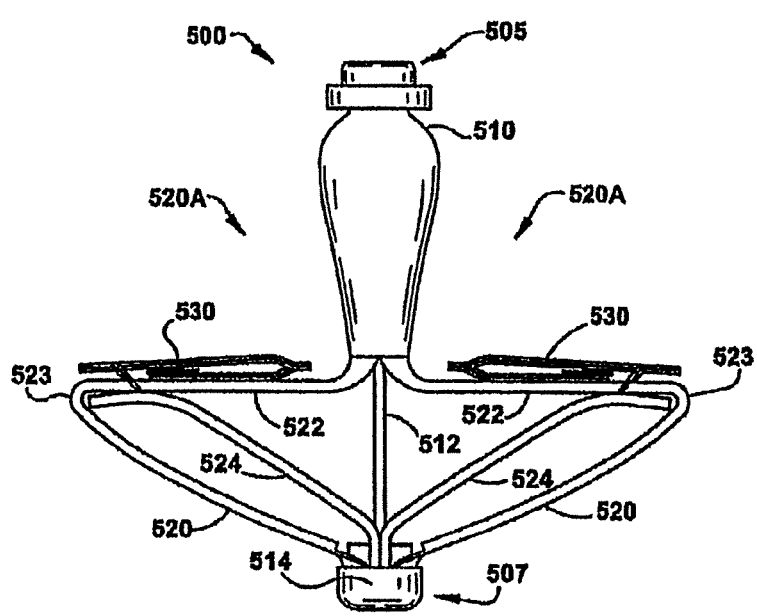
FIG. 38 shows a side view of an exemplary implantable prosthetic device in a half-open position with barbed clasps in a closed position.

Referring now to FIG. 38, the device 500 is shown in a laterally extended or open position. The device 500 is moved into the laterally extended or open position by continuing to extend the actuation wire 512 described above, thereby increasing the distance D between the attachment portion 505 and distal portion 507. Continuing to extend the actuation wire 512 pulls down on the outer paddles 520 and biasing members 524, thereby causing the inner paddles 522 to spread apart further from the coaption element 510. In the laterally extended or open position, the inner paddles 522 extend horizontally more than in other positions of the device 500 and form an approximately 90-degree angle with the coaption element 510. Similarly, the biasing members 524 are at their maximum spread position when the device 500 is in the laterally extended or open position. The increased gap 520A formed in the laterally extended or open position allows clasps 530 to open further (not shown) before engaging the coaption element 510, thereby increasing the size of the gap 530A.

In some embodiments, the inner paddles 522A are stiff, relatively stiff, rigid, have rigid portions and/or are stiffened by a stiffening member or the fixed portion of the clasps 530C. The stiffening of the inner paddle allows the device to move to the various different positions shown and described herein.

In one exemplary embodiment, one or more devices having the design of the devices 100, 200, 400A, 500 described herein or another design can be configured to:

Be implanted in a closed condition and open and close with the native valve, as the native valve opens and closes;

Be implanted in a partially open condition and further open and move toward the partially open implanted condition with the native valve, as the native valve opens and closes; and/or Be implanted in a partially open condition and remain in the partially open implanted condition (i.e. remains stationary), as the native valve opens and closes.

These device configurations reduce the pressure gradient across the native valve by allowing the area of the native valve that is captured by the device to move as the native valve opens and closes or reduces the pressure gradient across the native valve by maintaining the area of the native valve that is captured by the device in an open or partially open position.

Figure 39:
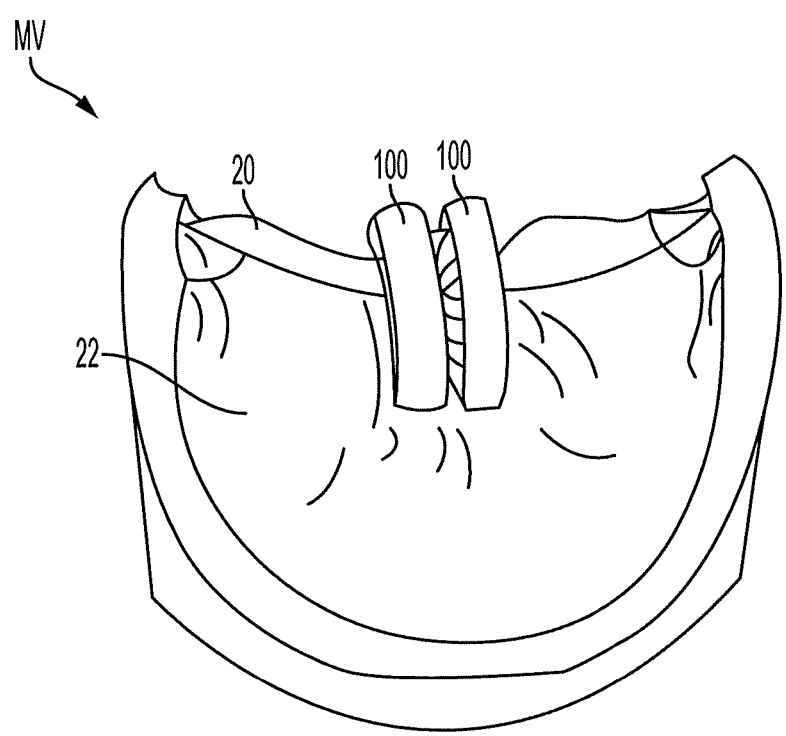
FIG. 39 shows an exemplary implantable prosthetic device implanted on leaflets in a closed position.

Any number of devices can be implanted to achieve these benefits. In the example illustrated by FIG. 39, two implantable prosthetic devices in accordance with an exemplary embodiment are positioned on the leaflets 20, 22 of a mitral valve MV (viewed from the ventricular side of the mitral valve). While illustrated on a mitral valve, the devices can be implanted on any native heart valve. However, in other exemplary embodiments, only a single device is implanted. The illustrated implanted devices 100 are positioned side by side. As illustrated in FIG. 39, one or more implants 100 can be used to approximate, or coapt, the leaflets together in a centrally located region of the leaflets. FIG. 39 illustrates the leaflets in a partially closed position.

Figure 40A:
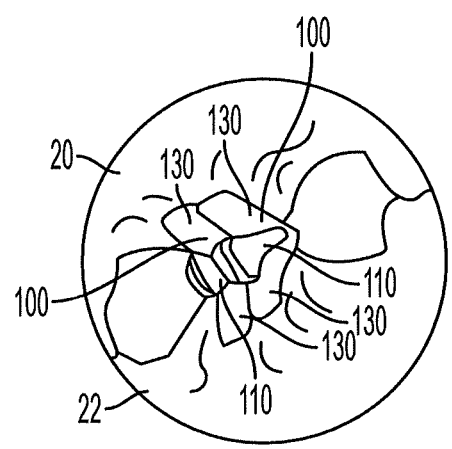
FIG. 40A shows an exemplary embodiment of an implantable prosthetic device attached to leaflets of a mitral valve in an open position.
Figure 40B:
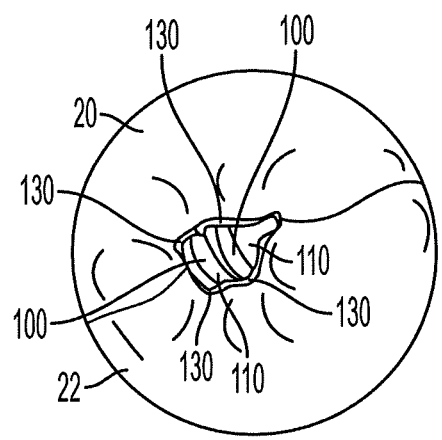
FIG. 40B shows an exemplary embodiment of the implantable prosthetic device of FIG. 40A in a closed position.

Referring now to FIGS. 40A and 40B, the two implantable prosthetic devices 100 (each identified by a coaption element 110 and inner clasps 130) are shown implanted on the leaflets 20, 22 of a native mitral valve MV, from a point of view taken from the atrium looking down toward the ventricle. The leaflets are secured between the inner clasps 130 and outer clasps and/or paddles (not shown in the point of view of FIGS. 40A and 40B). The closed clasps and paddles on each device can be pivot between open and closed positions by the opening and closing of the mitral valve. In FIG. 40A, the leaflets are approximated to each other by the device, and the leaflets and clasps are in an open configuration, as occurs during diastole. The opening of the leaflets, which occurs naturally, forces the clasps to open as well. The gap in FIG. 40A has a "barbell" or "figure-eight" appearance because of the approximation of the center of the leaflets to each other by the device. On either side of the devices 100, the leaflets open, permitting blood to flow through from the left atrium to the left ventricle. The movement of the clasps is one exemplary embodiment of increasing the mobility of the leaflets to reduce the pressure gradient between the left atrium and left ventricle, which can occur when implantable prosthetic devices are implanted in a native cardiac valve and are maintained in a closed position while the native valve leaflets open and close. The leaflet mobility permitted after the implantation of such as device as that in FIG. 40A allows gaps of sufficient area between the leaflets, and an effective orifice area, great enough to keep the pressure gradient between the atrium and ventricle less than or equal to 5 mmHg after implantation of the device(s). The leaflet mobility permitted after the implantation of such as device as that in FIG. 40A allows reduces the stress placed on the native valve leaflet tissue by the claps and/or paddles.

Referring now to FIG. 40B, the devices 100 implanted on the mitral valve leaflets 20, 22 are shown during systole, when the leaflets are closed. The closed clasps 134 (outer clasps and paddles not shown in this view) are moved in toward a central coaption element 110 and the leaflets are approximated together across the entire width of each leaflet. The implantable prosthetic devices assist in hold the central portions leaflets together during systole to correct regurgitation that would otherwise occur in a diseased or defective valve.

Figure 41A:
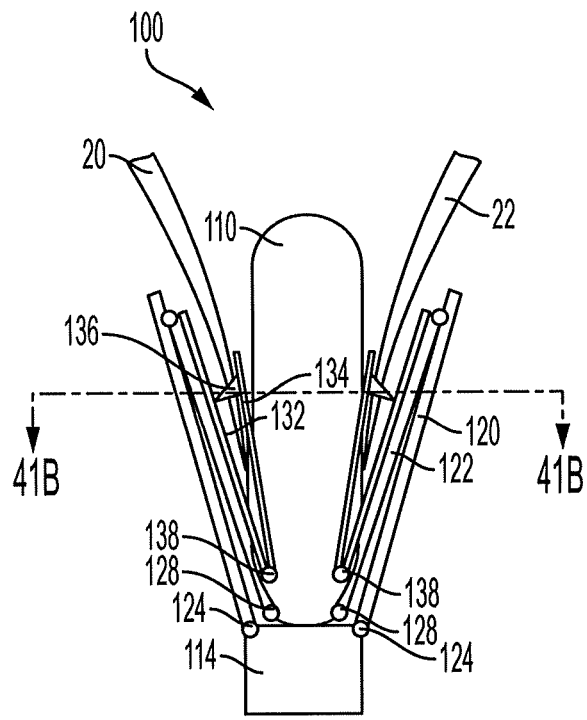
FIG. 41A shows a side view of an exemplary embodiment of an implantable prosthetic device having clasps, a paddle frame, and a coaption element in a closed position.

Referring now to FIGS. 41A-42B, an exemplary embodiment of an implantable prosthetic device 100 secured to leaflet tissue, having clasps each with an inner clasp 134 and an outer clasp 132, inner paddles 122, outer paddles 120, and a coaption element 110, is shown. FIG. 41A illustrates a side cross-section schematic of an exemplary embodiment, where the cross-section is taken through the center of the device. FIG. 41A illustrates the implantable prosthetic device in a closed position, with the clasps and the paddles positioned to hold the leaflets secure against the coaption element. Each leaflet 20, 22 is secured between an inner clasp 134 and an outer clasp 132. The clasps can have barbs 136 that penetrate the leaflet tissue to further secure the leaflet in between the clasps. The inner and outer clasps 134, 132 can be pivotally secured to the coaption element at a joint portion 138. The coaption element can be of any of the embodiments described herein regarding size, shape, and material. The inner paddles 122 can each be connected to the coaption element by a joint portion 128, and the outer paddles 120 can each be connected to the cap 114 by a joint portion 124. The joint portions 138, 128, and 124 can each be positioned on the coaption element 110 or on the cap 114.

Figure 41B:
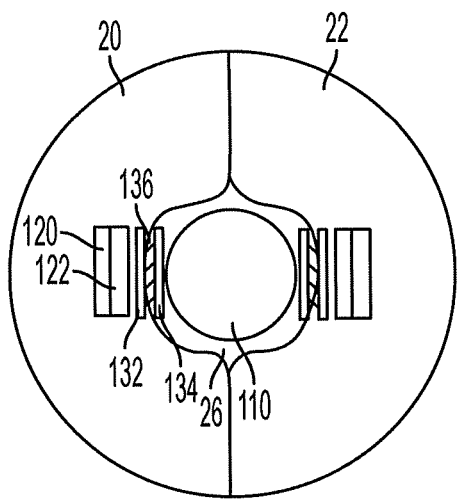
FIG. 41B shows a cross-section of the exemplary embodiment of FIG. 41A taken along line 41B-41B.

FIG. 41B illustrates a cross-section of the device in FIG. 41A, taken along line 41B-41B, looking in a downward direction, from the direction of the atrium towards the ventricle. In FIG. 41B, the leaflets 20, 22 are secured between the inner and outer clasps 134, 132, further secured in place by barbs 136. The clasps 134, 132 and paddles 120, 122 are in a closed position. The leaflets are in a closed position, with the leaflet edges coapted together and in the center region of the leaflets, where the leaflets are positioned between the clasps, the leaflets are coapted around the coaption device.

Figure 42A:
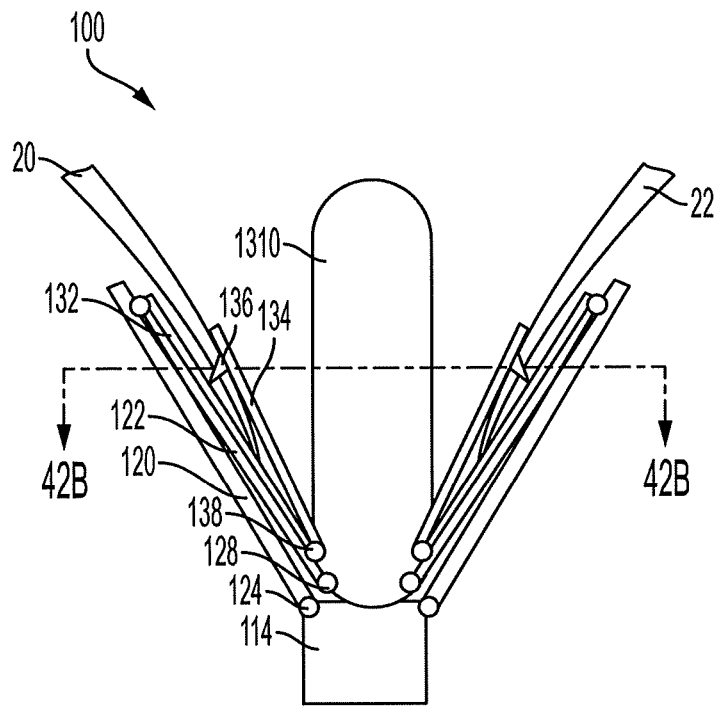
FIG. 42A shows a side view of an exemplary embodiment of an implantable prosthetic device having clasps, a paddle frame, and a coaption element in an open position.
Figure 42B:
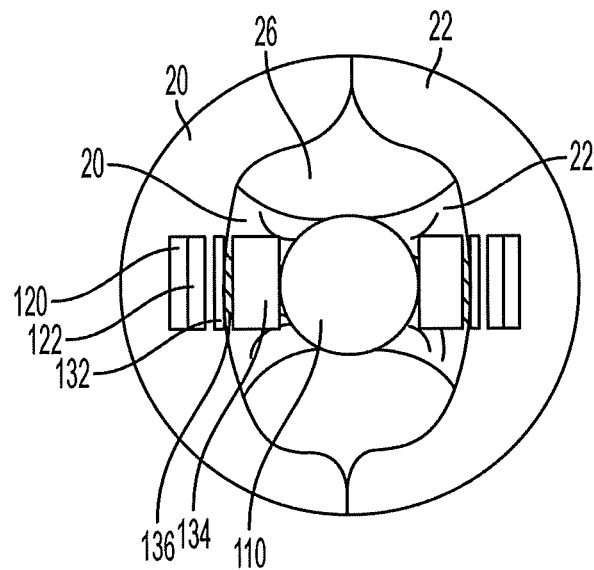
FIG. 42B shows a cross-section of the exemplary embodiment of FIG. 42A taken along line 42B-42B.

FIGS. 42A and 42B are representative of two embodiments. That is, FIGS. 42A and 42B illustrate both:

An embodiment where the device moves from the closed position illustrated by FIGS. 41A and 41B to the partially open position illustrated by FIGS. 42A and 42B when the native valve opens and closes; and An embodiment where the device is implanted in the partially open position illustrated by FIGS. 42A and 42B.

In the first example, FIGS. 42A and 42B illustrate the device moved to a partially open position from the position shown in FIGS. 41A and 41B by the native valve leaflets. In the open position, the inner clasps 134, outer clasps 132, inner paddles 122, and outer paddles 120 are all pivoted away from the coaption element at the joint portions 124, 128, 138 by the opening of the native valve leaflets. This position of the clasps and paddles can permit less of the leaflets to be coapted against the coaption device during diastole, thereby increasing the effective orifice area and reducing the gradient in blood pressure between the ventricle and atrium.

FIG. 42B illustrates the cross-section of the device in the open position in FIG. 42A, taken along line 42B-42B, looking in a downward direction, from the atrium towards the ventricle. In FIG. 42B, the leaflets 20, 22 remain secured between the inner and outer clasps, further secured by barbs 136. The leaflets are in an open position, and a central region of each of the leaflets remains coapted to the coaption device. The gap 26 between the leaflets is visible.

The device 100 can be configured to be moved from the closed position (e.g. FIGS. 41A and 41B) to the partially open position (e.g. FIGS. 42A and 42B) in a wide variety of different ways. For example, in one exemplary embodiment the paddles 120, 122 can be biased to the closed position by one or more spring elements, but the biasing force is low enough to be overcome by the opening and closing of the native valve and partially open the paddles 120, 122. In another exemplary embodiment, the paddles 120, 122 are not biased to any position and can freely move between the closed position and the partially open position. In yet another exemplary embodiment, the paddles 120, 122 are closed, but the paddles are flexible enough to flex from a closed position to a position that is similar to the partially open position illustrated by FIGS. 42A and 42B. Any device configuration that reduces the constraints on the native valve leaflets by the device as the native valve moves from the closed state to the open state can be implemented.

In the second example, FIG. 42A illustrates an embodiment where the device 100 is implanted in partially open position. In one exemplary embodiment, the device is configured to remain fixed, once implanted, such that the inner clasps 134, outer clasps 132, inner paddles 122, and outer paddles 120 maintain the same position throughout the cardiac cycle. The leaflets will still open and close during the cardiac cycle while the clasps and paddles of the device remain fixed in this partially open position. This is another exemplary embodiment of permitting more flexibility of the native valve leaflets upon implantation of a prosthetic implant device to maintain a low pressure gradient between the atrium and ventricle.

In yet another exemplary embodiment, the device 100 is still implanted in a partially open position illustrated by FIGS. 42A and 42B, but the implanted device is configured to open further than partially open position as the native valve leaflets open during the cardiac cycle. This is yet another exemplary embodiment of permitting more flexibility of the native valve leaflets upon implantation of a prosthetic implant device to maintain a low-pressure gradient between the atrium and ventricle.

Figure 43A:
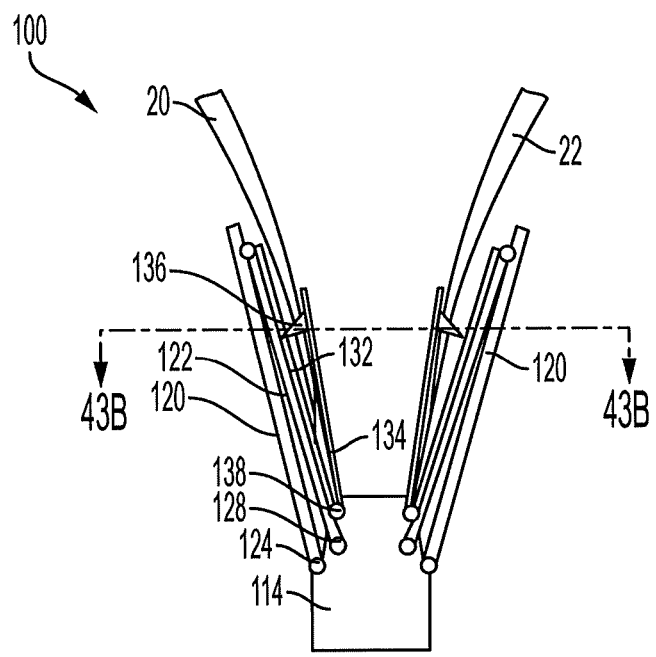
FIG. 43A shows a side view of an exemplary embodiment of an implantable prosthetic device having clasps and a paddle frame in a closed position.

Referring now to FIGS. 43A-44B, an exemplary embodiment of an implantable prosthetic device 100 secured to leaflet tissue, having inner clasps, 134, outer clasps 132, inner paddles 122, and outer paddles 120 is shown. FIG. 43A illustrates a side cross-section schematic of an exemplary embodiment, where the cross-section is taken through the center of the device. In this embodiment, there is no coaption spacer element. There can be a cap 114 on which the inner clasps 134 and outer clasps 132 are connected with a joint portion 138, on which the inner paddles are connected to with a joint portion 128, and on which the outer paddles are connected with a joint portion 124. FIG. 43A illustrates the implantable prosthetic device in a closed position, with the leaflets also in a closed position. Each leaflet 20, 22 is secured between an inner clasp 134 and an outer clasp 132. The clasps can have barbs 136 that penetrate the leaflet tissue to further secure the leaflet in between the clasps. The inner and outer clasps 134, 132 can be pivotally or flexibly secured to the coaption element at a joint portion 138. The inner paddles 122 can each be connected to the coaption element by a flexible portion or joint portion 128, and the outer paddles 120 can each be connected to the cap 114 by a joint portion 124.

Figure 43B:
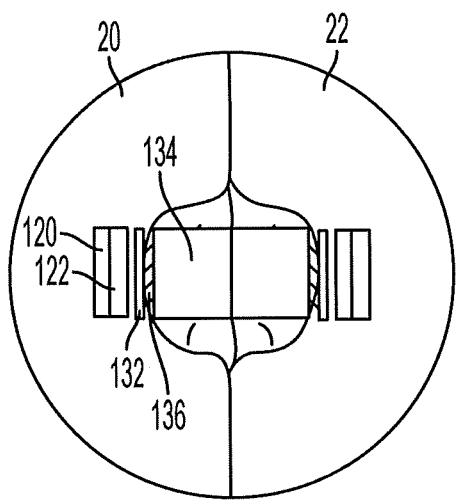
FIG. 43B shows a cross-section of the exemplary embodiment of FIG. 43A taken along line 43B-43B.

FIG. 43B illustrates a cross-section of the device in FIG. 43A, taken along line 43B-43B, looking in a downward direction, from the direction of the atrium towards the ventricle. In FIG. 44B, the leaflets 20, 22 are secured between the inner and outer clasps 134, 132. The clasps 134, 132 and paddles 120, 122 are in a closed position. The leaflets are in a closed position, with the leaflets coapted together.

Figure 44A:
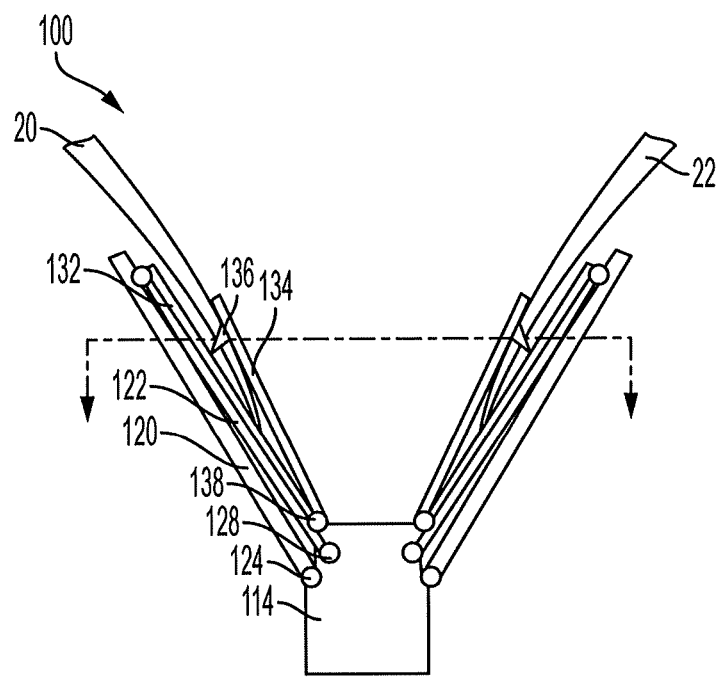
FIG. 44A shows a side view of an exemplary embodiment of an implantable prosthetic device having clasps and a paddle frame in an open position.
Figure 44B:
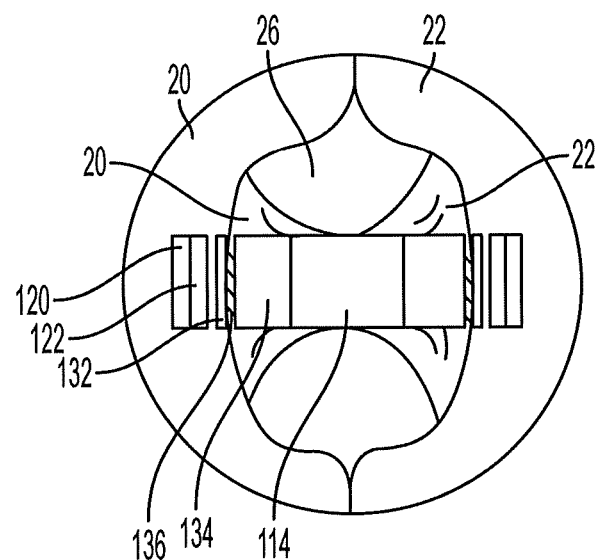
FIG. 44B shows a cross-section of the exemplary embodiment of FIG. 44A.

FIGS. 44A and 44B are representative of two embodiments. That is, FIGS. 44A and 44B illustrate both:

An embodiment where the device moves from the closed position illustrated by FIGS. 43A and 43B to the partially open position illustrated by FIGS. 44A and 44B when the native valve opens and closes; and An embodiment where the device is implanted in the partially open position illustrated by FIGS. 44A and 44B.

In the first example, FIGS. 44A and 44B illustrate the device moved to a partially open position from the position shown in FIGS. 43A and 4B by the native valve leaflets. In the open position, the inner clasps 134, outer clasps 132, inner paddles 122, and outer paddles 120 are all pivoted at the joint portions 124, 128, 138 by the opening of the native valve leaflets. This position of the clasps and paddles can permit the leaflets to move more (as compared to the position of the closed device shown in FIGS. 43A and 43B), thereby increasing the effective orifice area and reducing the gradient in blood pressure between the ventricle and atrium.

FIG. 44B illustrates the cross-section of the device in the open position in FIG. 44A, taken along line 44B-44B, looking in a downward direction, from the atrium towards the ventricle. In FIG. 44B, the leaflets 20, 22 remain secured between the inner and outer clasps. The leaflets are in an open position, and a central region of each of the leaflets remains connected to the clasps. The gap 26 between the leaflets is visible.

The device 100 can be configured to be moved from the closed position (e.g. FIGS. 43A and 43B) to the partially open position (e.g. FIGS. 44A and 44B) in a wide variety of different ways. For example, in one exemplary embodiment the paddles 120, 122 can be biased to the closed position by one or more spring elements, but the biasing force is low enough to be overcome by the opening and closing of the native valve and partially open the paddles 120, 122. In another exemplary embodiment, the paddles 120, 122 are not biased to any position and can freely move between the closed position and the partially open position. In yet another exemplary embodiment, the paddles 120, 122 are closed, but the paddles are flexible enough to flex from a closed position to a position that is similar to the partially open position illustrated by FIGS. 44A and 44B. Any device configuration that reduces the constraints on the native valve leaflets by the device as the native valve moves from the closed state to the open state can be implemented.

In the second example, FIG. 44A illustrates an embodiment where the device 100 is implanted in partially open position. In one exemplary embodiment, the device is configured to remain fixed, once implanted, such that the inner clasps 134, outer clasps 132, inner paddles 122, and outer paddles 120 maintain the same position throughout the cardiac cycle. The leaflets will still open and close during the cardiac cycle while the clasps and paddles of the device remain fixed in this partially open position. This is another exemplary embodiment of permitting more flexibility of the native valve leaflets upon implantation of a prosthetic implant device to maintain a low pressure gradient between the atrium and ventricle.

In yet another exemplary embodiment, the device 100 is still implanted in a partially open position illustrated by FIGS. 44A and 44B, but the implanted device is configured to open further than the illustrated partially open position as the native valve leaflets open during the cardiac cycle. This is yet another exemplary embodiment of permitting more flexibility of the native valve leaflets upon implantation of a prosthetic implant device to maintain a low-pressure gradient between the atrium and ventricle.

Figure 45A:
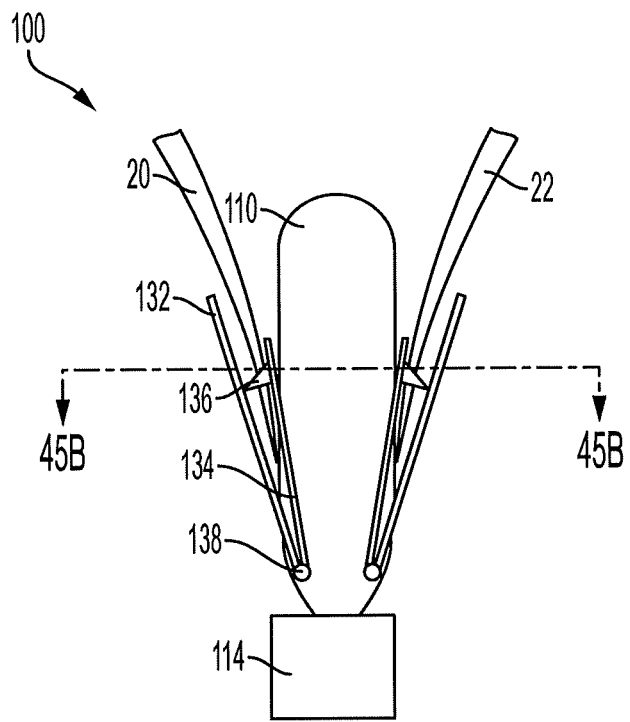
FIG. 45A shows a side view of an exemplary embodiment of an implantable prosthetic device having clasps and a coaption element in a closed position.

Referring now to FIGS. 45A-46B, an exemplary embodiment of an implantable prosthetic device 100 secured to leaflet tissue 20, 22, having clasps 134, 132 and a coaption element 110, but no paddles is shown. FIG. 45A illustrates a side cross-section schematic of an exemplary embodiment, where the cross-section is taken through the center of the device. FIG. 45A illustrates the implantable prosthetic device in a closed position, with the clasps positioned to hold the leaflets secure against the coaption element. Each leaflet 20, 22 is secured between an inner clasp 134 and an outer clasp 132. The clasps can have barbs 136 that penetrate the leaflet tissue to further secure the leaflet in between the clasps. The inner and outer clasps 134, 132 can be pivotally secured to the coaption element at a joint portion 138. The coaption element can be of any of the embodiments described herein regarding size, shape, and material. The joint portions 138, can be positioned on the coaption element 110 or on the cap 114.

Figure 45B:
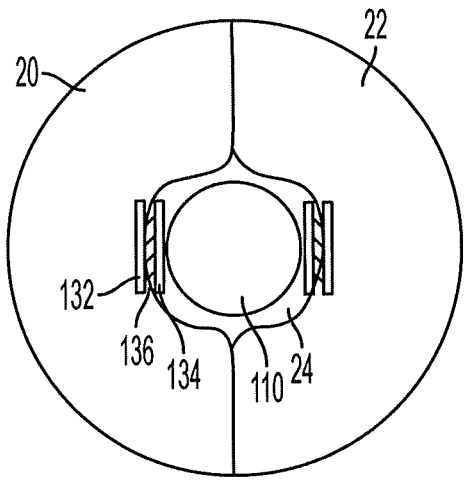
FIG. 45B shows a cross-section of the exemplary embodiment of FIG. 45A taken along line 45B-45B.

FIG. 45B illustrates a cross-section of the device in FIG. 45A, taken along line 45B-45B, looking in a downward direction, from the atrium towards the ventricle. In FIG. 45B, the leaflets 20, 22 are secured between the inner and outer clasps 134, 132, further secured by the barbs 136. The clasps 134, 132 are in a closed position. The leaflets are in a closed position, with the leaflets coapted together and in the center region of the leaflets, where positioned between the clasps, the leaflets are coapted around the coaption device.

Figure 46A:
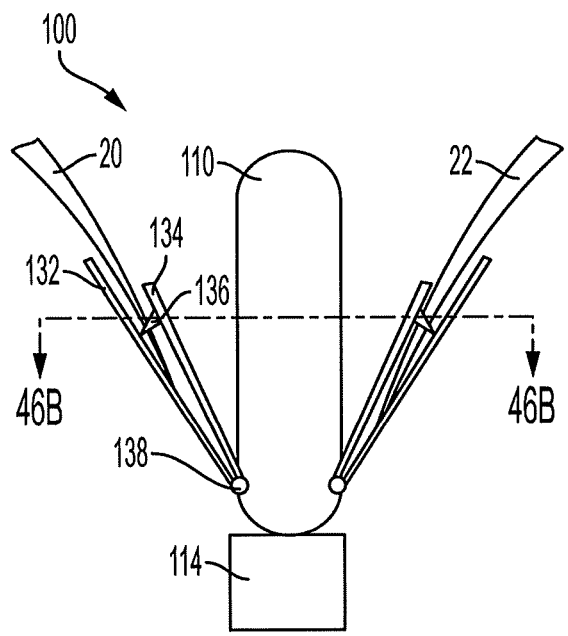
FIG. 46A shows a side view of an exemplary embodiment of an implantable prosthetic device having clasps and a coaption element in an open position.
Figure 46B:
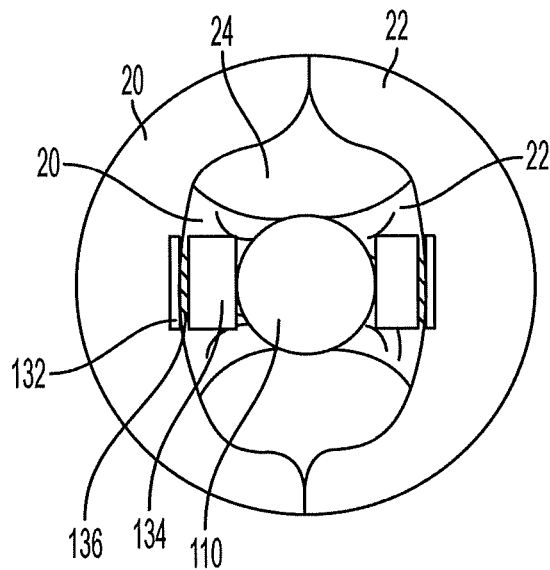
FIG. 46B shows a cross-section of the exemplary embodiment of FIG. 46A taken along line 46B-46B.

FIGS. 46A and 46B are representative of two embodiments. That is, FIGS. 46A and 46B illustrate both:

An embodiment where the device moves from the closed position illustrated by FIGS. 45A and 45B to the partially open position illustrated by FIGS. 46A and 46B when the native valve opens and closes; and An embodiment where the device is implanted in the partially open position illustrated by FIGS. 46A and 46B.

In the first example, FIGS. 46A and 46B illustrate the device moved to a partially open position from the position shown in FIGS. 45A and 45B by the native valve leaflets. In the open position, the inner clasps 134 and outer clasps 132 are pivoted at the joint portions 138 by the opening of the native valve leaflets. This position of the clasps can permit the leaflets to move more (as compared to the position of the closed device shown in FIGS. (45A and 45B), thereby increasing the effective orifice area and reducing the gradient in blood pressure between the ventricle and atrium.

FIG. 46B illustrates the cross-section of the device in the open position in FIG. 46A, taken along line 46B-46B, looking in a downward direction, from the atrium towards the ventricle. In FIG. 46B, the leaflets 20, 22 remain secured between the inner and outer clasps. The leaflets are in an open position, and a central region of each of the leaflets remains connected to the clasps and coapted around the coaption element 110. The gap 26 between the leaflets is visible.

The device 100 can be configured to be moved from the closed position (e.g. FIGS. 45A and 45B) to the partially open position (e.g. FIGS. 46A and 46B) in a wide variety of different ways. For example, in one exemplary embodiment the clasps 132, 134 can be biased to the closed position by one or more spring elements, but the biasing force is low enough to be overcome by the opening and closing of the native valve and partially open the paddles 120, 122. In another exemplary embodiment, the clasps 132, 134 are not biased to any position and can freely move between the closed position and the partially open position. In yet another exemplary embodiment, the clasps 132, 134 are closed, but the clasps are flexible enough to flex from a closed position to a position that is similar to the partially open position illustrated by FIGS. 46A and 46B. Any device configuration that reduces the constraints on the native valve leaflets by the device as the native valve moves from the closed state to the open state can be implemented.

In the second example, FIG. 46A illustrates an embodiment where the device 100 is implanted in partially open position. In one exemplary embodiment, the device is configured to remain fixed, once implanted, such that the inner clasps 134 and outer clasps 132 maintain the same position throughout the cardiac cycle. The leaflets will still open and close during the cardiac cycle while the clasps of the device remain fixed in this partially open position. This is another exemplary embodiment of permitting more flexibility of the native valve leaflets upon implantation of a prosthetic implant device to maintain a low pressure gradient between the atrium and ventricle.

In yet another exemplary embodiment, the device 100 is still implanted in a partially open position illustrated by FIGS. 46A and 46B, but the implanted device is configured to open further than the illustrated partially open position as the native valve leaflets open during the cardiac cycle. This is yet another exemplary embodiment of permitting more flexibility of the native valve leaflets upon implantation of a prosthetic implant device to maintain a low-pressure gradient between the atrium and ventricle.

Referring now to FIGS. 47A-48B, another exemplary embodiment is illustrated. In this embodiment, the device 500 can have a wide variety of different shapes and sizes. Referring to 47A and 47B, the coaption element 510 functions as a gap filler in the valve regurgitant orifice, such as the gap 26 in the mitral valve MV illustrated by FIG. 6. Because the coaption element 510 is deployed between two opposing valve leaflets 20, 22, the leaflets will not coapt against each other in the area of the coaption element 510, but coapt against the coaption element 510 instead. This reduces the distance the leaflets 20, 22 need to be approximated. A reduction in leaflet approximation distance can result in several advantages. For example, the coaption element and resulting reduced approximation can facilitate repair of severe mitral valve anatomies, such as large gaps in functional valve disease (see for example, FIG. 6). Since the coaption element reduces the distance the native valves have to be approximated, the stress in the native valves can be reduced or minimized. Shorter approximation distance of the valve leaflets 20, 22 can require less approximation forces which can result in less tension of the leaflets and less diameter reduction of the valve annulus. The smaller reduction of the valve annulus (or no reduction of the valve annulus) can contribute to less reduction in valve orifice area. As a result, the coaption element can reduce the transvalvular gradients.

Figure 47A:
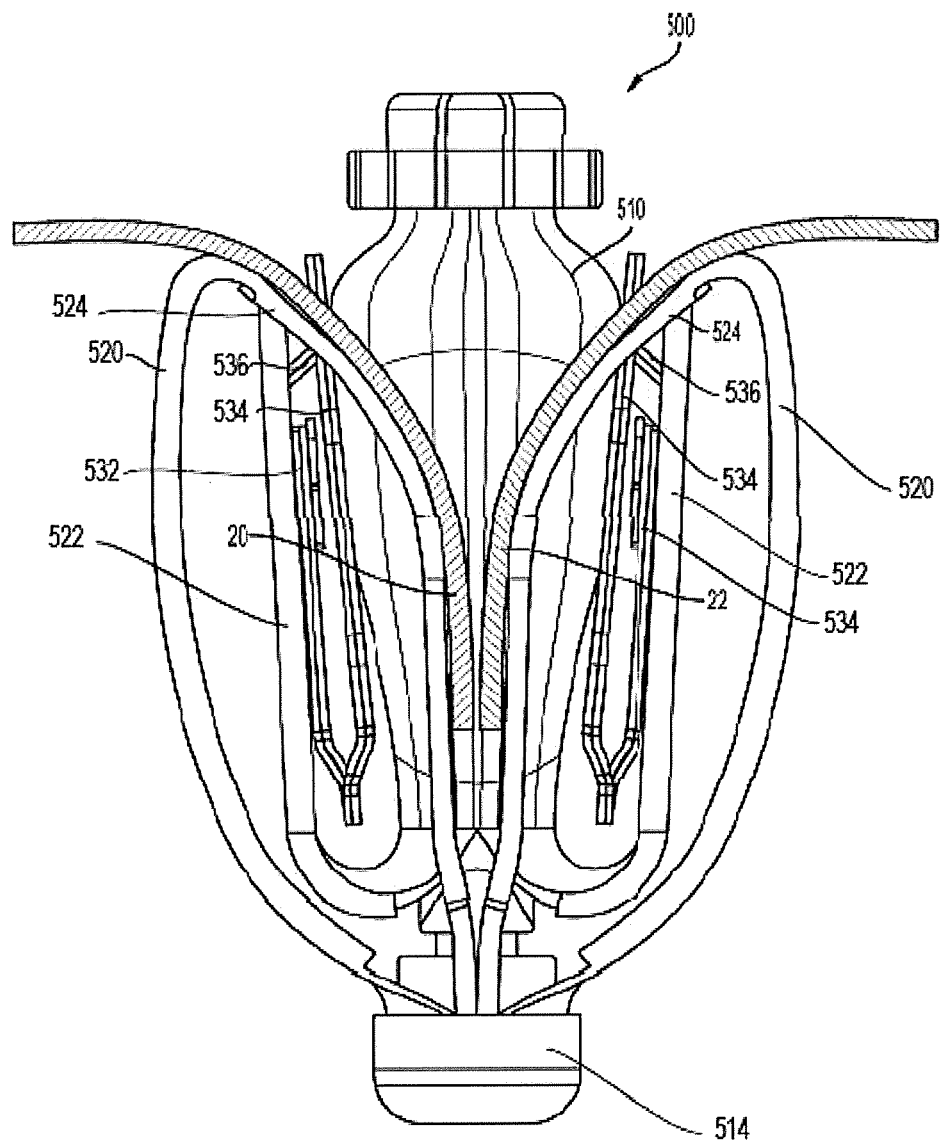
FIG. 47A shows a schematic view of a path of mitral valve leaflets along each side of an exemplary embodiment of a mitral valve repair device having clasps, a coaption element, and a paddle frame in a closed position.
Figure 47B:
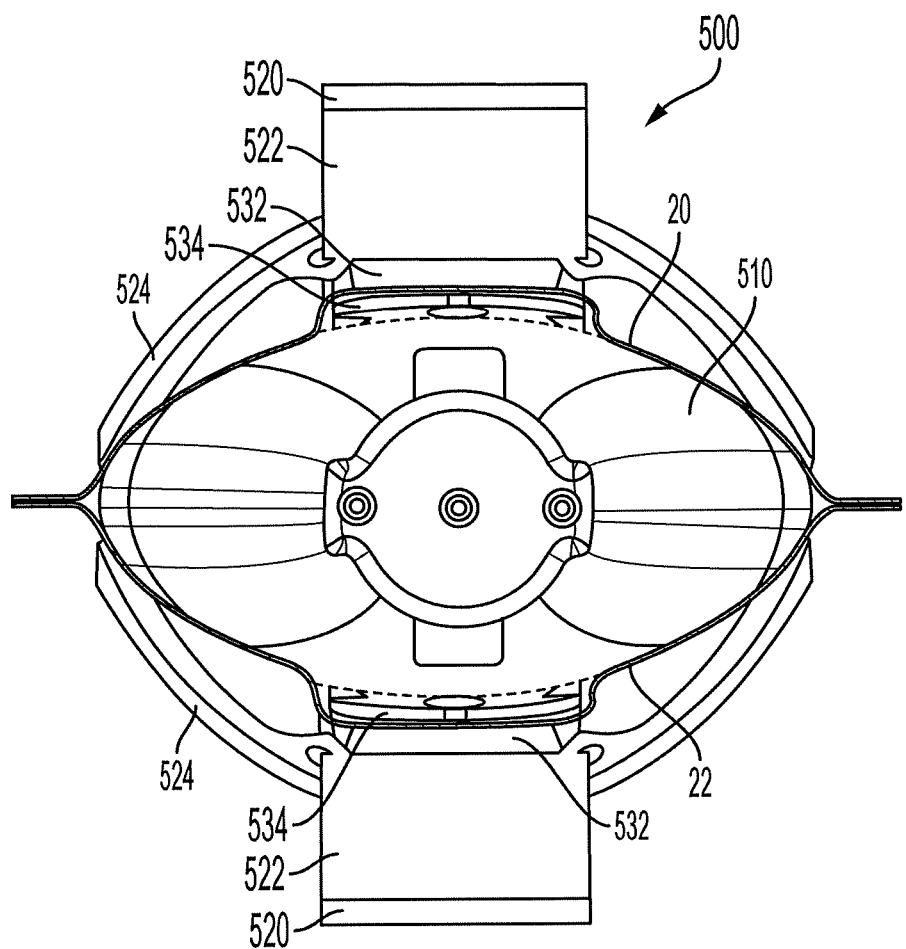
FIG. 47B shows a cross-section of the exemplary embodiment of FIG. 47A.

Referring now to FIGS. 47A and 47B, in exemplary embodiments having a paddle frame, clasps, biasing members, and a coaption element, the biasing members 524 conform to the shape of the coaption element 510. In one example, if the coaption element 510 is wider than the biasing members 524, a distance (gap) between the opposing leaflets 20, 22 can be created by the device 500. Referring to the exemplary embodiment illustrated in FIGS. 47A and 47B, the paddles 522, 520 surround the coaption element 510. Thus, when the leaflets 20, 22 are coapted against the coaption element 510, the leaflets 20, 22 fully surround or "hug" the coaption element 510 in its entirety, thus small leaks on the medial and lateral aspects of the coaption element 510 can be prevented.

Referring to FIGS. 47A and 47B, because biasing members 524 of the paddle frames 520, 522 conform to the shape of the coaption element 510, the valve leaflets 20, 22 can be coapted completely around the coaption element by the biasing member 524, including on the lateral and medial aspects 601, 603 of the coaption element 510. This coaption of the leaflets 20, 22 against the lateral and medial aspects of the coaption element 510 would seem to contradict the statement above that the presence of a coaption element 510 minimizes the distance the leaflets need to be approximated. However, the distance the leaflets 20, 22 need to be approximated is still minimized if the coaption element 510 is placed precisely at a regurgitant gap and the regurgitant gap is less than the width (medial—lateral) of the coaption element 510.

FIG. 47A illustrates the geometry of the coaption element 510 and the paddle frame elements (inner paddle 522, outer paddle 520, and biasing member 524) from a cross-section view, taken from cross-section farther toward a forward facing side view rather than from the center. In this cross-section, offset from the center of the device, the leaflets 20, 22 are shown to be wrapped around the coaption element. In the center, the leaflets 20, 22 are positioned between the inner clasp 134 and outer clasp 132 on each side of the device. As can be seen in this view, the coaption element 510 has a tapered shape being smaller in dimension in the area closer to where the inside surfaces of the leaflets 20, 22 are required to coapt and increase in dimension as the coaption element extends toward the atrium. The anatomy of the leaflets 20, 22 is such that the inner sides of the leaflets coapt at the free end portions and the leaflets 20, 22 start receding or spreading apart from each other. The leaflets 20, 22 spread apart in the atrial direction, towards the annulus where the leaflets are attached. The depicted native valve geometry is accommodated by a tapered coaption element geometry. Still referring to FIG. 47A, the tapered coaption element geometry, in conjunction with the illustrated biasing component 524 which biases the paddles 522, 520 (toward the valve annulus) can help to achieve coaptation on the lower end of the leaflets, reduce stress, and minimize transvalvular gradients.

Referring to FIG. 47B, a schematic atrial view depicts the paddle frames (which would not actually be visible from a true atrial view), conforming to the spacer geometry. The opposing leaflets 20, 22 (the ends of which would also not be visible in the true atrial view) being approximated by the paddles, to fully surround or "hug" the coaption element 510.

Referring again to FIG. 47B, the coaption element 510 can take a wide variety of different shapes. In one exemplary embodiment, when viewed from the top (and/or sectional views from the top), the coaption element has an oval shape or an elliptical shape. The oval or elliptical shape can allow the additional biasing components 524 to conform to the shape of the coaption element and/or can reduce lateral leaks.

As mentioned above, the coaption element 510 can reduce tension of the opposing leaflets by reducing the distance the leaflets need to be approximated to the coaption element 510 at the positions 601, 603. The reduction of the distance of leaflet approximation at the positions 601, 603 can result in the reduction of leaflet stresses and gradients. In addition, as is also explained above, the native valve leaflets 20, 22 can surround or "hug" the coaption element in order to prevent lateral leaks. In one exemplary embodiment, the geometrical characteristics of the coaption element can be designed to preserve and augment these two characteristics of the device 500.

In one exemplary embodiment, the valve repair device 500 and its coaption element 510 are designed to conform to the geometrical anatomy of the valve leaflets 20, 22. To achieve valve sealing, the valve repair device 500 can be designed to coapt the native leaflets to the coaption element, completely around the coaption element, including at the medial 601 and lateral 603 positions of the coaption element 510. Additionally, a reduction on forces required to bring the leaflets into contact with the coaption element 510 at the positions 601, 603 can minimize leaflet stress and gradients.

Figure 48A:
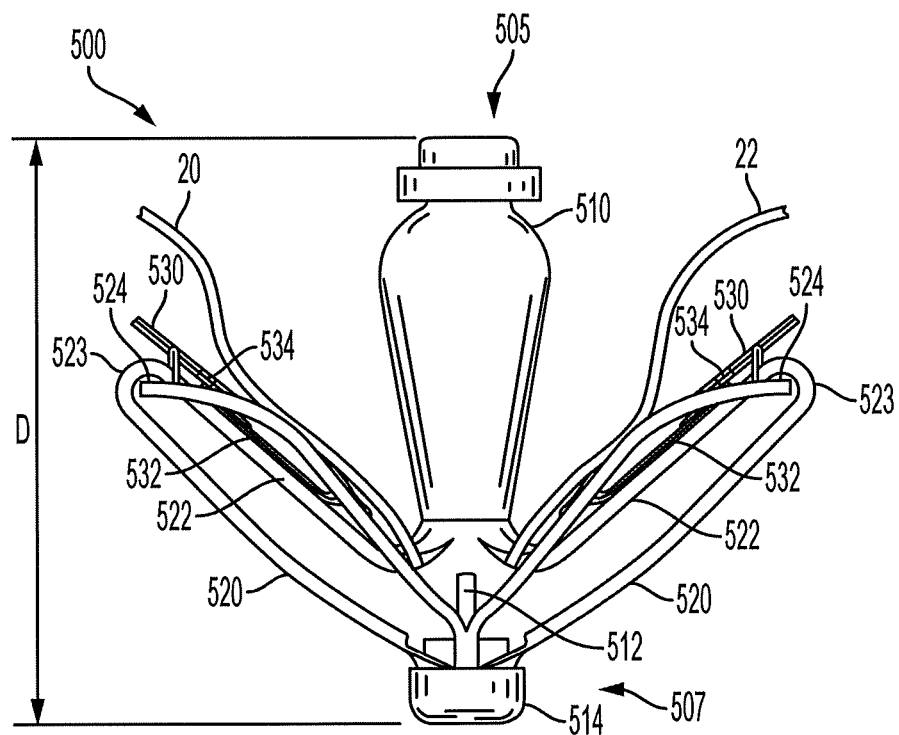
FIG. 48A shows a schematic view of a path of mitral valve leaflets along each side of an exemplary embodiment of a mitral valve repair device having clasps, a coaption element, and a paddle frame where the device is in an open position and the leaflets are open.
Figure 48B:
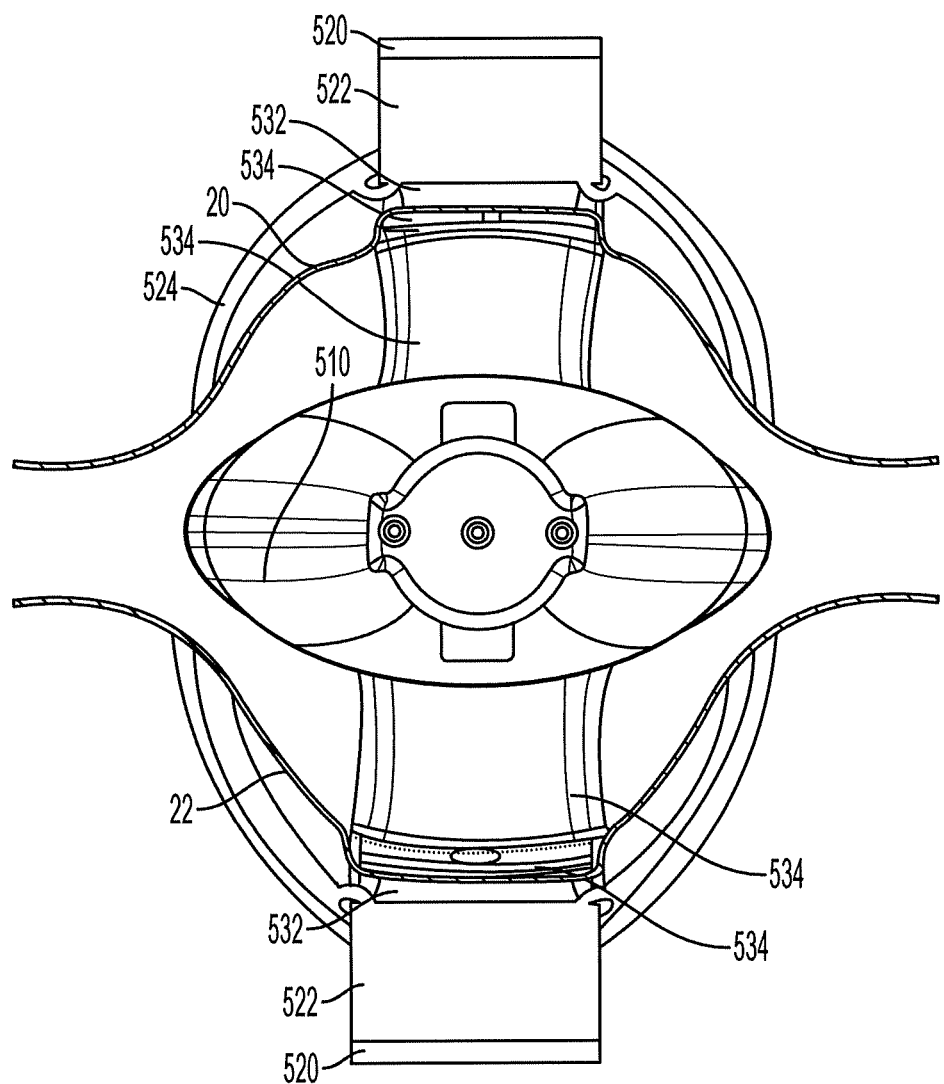
FIG. 48B shows a cross-section of the exemplary embodiment of FIG. 48A.

FIGS. 48A and 48B illustrate the device of FIGS. 47A and 47B where the pair of paddles 522, 520 are in a partially open position. The clasps 532, 534 are moved with the pair of paddles 520, 522 relative to the coaption element 510 to the illustrated partially open position. In FIG. 48A, the cross-section view is taken farther toward a forward facing side of the device rather than from the center. In this cross-section, offset from the center of the device, the leaflets 20, 22 are shown to be positioned surrounding the coaption element and coapted along their edges along the length of the leaflets not occupied by the coaption element. In the center, not seen from the point of view in FIG. 48A, the leaflets 20, 22 are positioned between the inner clasp 534 and outer clasp 532 on each side of the device. The clasps and paddles can be connected to the coaption element and/or cap as in the exemplary embodiments described herein. The clasps and paddles are pivoted away from the coaption element in the open position illustrated in FIG. 48A.

FIG. 48B illustrates a top-down view of the device shown in FIG. 48A. A schematic atrial view depicts the paddle frames (which would not actually be visible from a true atrial view), and the clasps (which would not be visible from a true atrial view), in an open position. The opposing leaflets 20, 22 (the ends of which would also not be visible in the true atrial view) are each held between an inner clasp 534 and an outer clasp 532. In this view, the leaflets are open to permit blood flow from the left atrium to the left ventricle.

The coaption element 510 can take a wide variety of different shapes. In one exemplary embodiment, when viewed from the top (and/or sectional views from the top), the coaption element has an oval shape or an elliptical shape. The oval or elliptical shape can allow the biasing members 524 to conform to the shape of the coaption element and/or can reduce lateral leaks.

The open position illustrated in FIGS. 48A and 48B depicts an embodiment where the clasps 534, 532, paddles 522, 520, and biasing member 524 on each side of the device can open and close throughout the cardiac cycle. In this embodiment, FIGS. 48A and 48B illustrate the clasps, paddles, and biasing elements in the "open" position, which occurs during ventricular diastole when the mitral valve leaflets are in an open position to permit blood flow from the left atrium to the left ventricle.

Figure 48C:
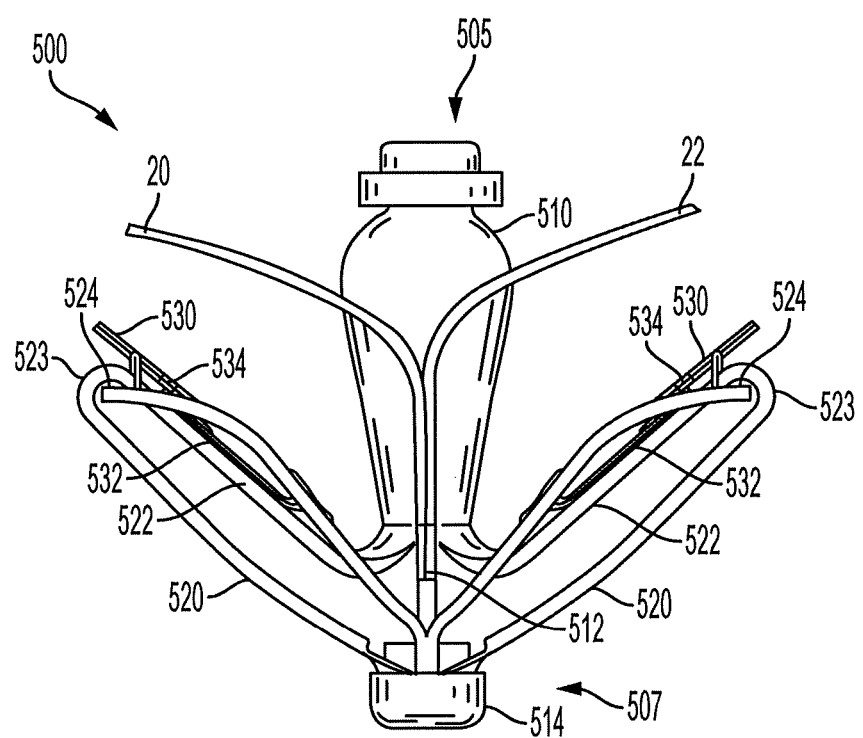
FIG. 48C shows a schematic view of a path of mitral valve leaflets along each side of an exemplary embodiment of a mitral valve repair device having clasps, a coaption element, and a paddle frame where the device is in an open position and the leaflets are closed.
Figure 48D:
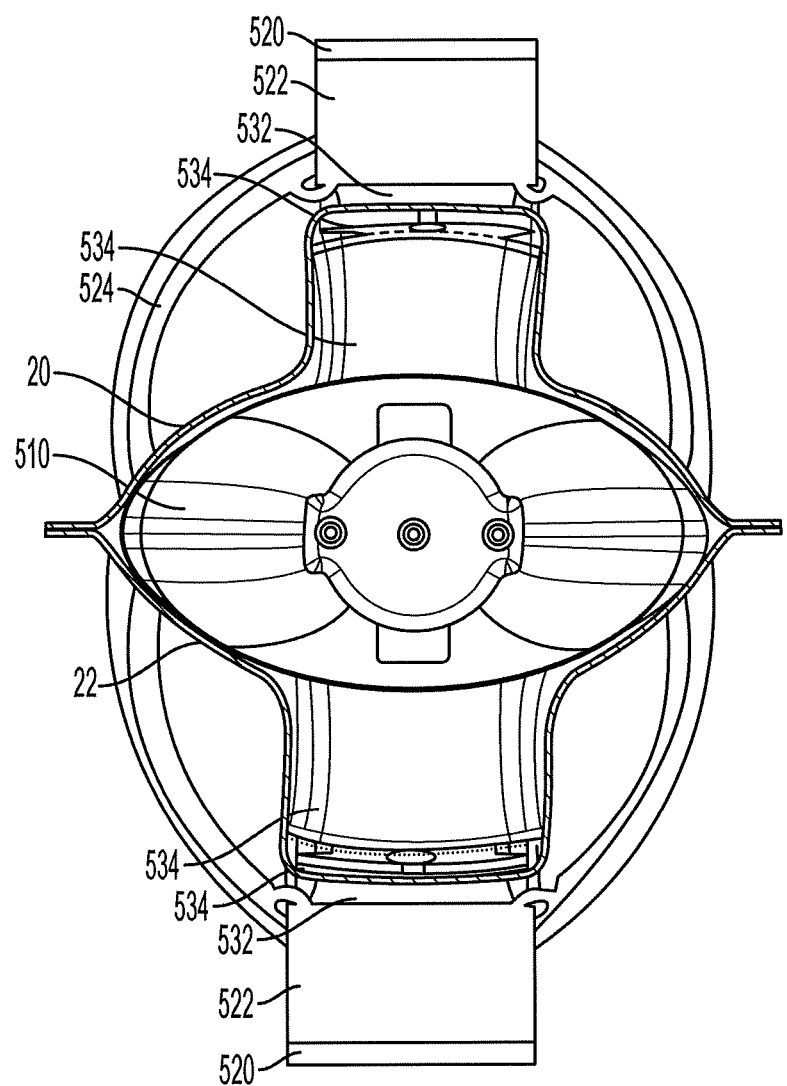
FIG. 48D shows a cross-section of the exemplary embodiment of FIG. 48C.

FIGS. 48A and 48B are also representative of an embodiment where the clasps and paddles remain in an open position during the cardiac cycle. In this embodiment, FIGS. 48A and 48B illustrate the device and mitral valve leaflets during ventricular diastole. In this embodiment, when the leaflets close such as during systole, the clasps and paddles can remain in an "open" position. FIGS. 48C and 48D illustrate the embodiment having fixed open clasps and paddles (i.e. the device itself is fixed in an open position), with closed leaflets during systole. When the leaflets close, the inner and outer clasps 134, 132 and inner and outer paddles 522, 520, remain in an open position. The central region of each of the leaflets remains fixed between the inner and outer clasps, and the sides of the leaflets approximate the coaption element 510 as illustrated in FIG. 48C. The leaflets are closed and a greater portion of the leaflets are coapted together, to the opposing leaflet edge and to the coaption element. As with the other exemplary embodiments described herein, the paddles and/or clasps can be made of a shape memory material or can be mechanically locked open.

FIG. 48D represents a top-down view of the device shown in FIG. 48C. A schematic atrial view depicts the paddle frames (which would not actually be visible from a true atrial view), and the clasps (of which the outer clasps would not be visible in a true atrial view), in an open position. The opposing leaflets 20, 22 (the ends of which would also not be visible in the true atrial view) are each held between an inner clasp 534 and an outer clasp 532. In this view, the leaflets 20, 22 are "closed" and approximated to the coaption element 510, to prevent blood flow from the left atrium to the left ventricle.

In yet another exemplary embodiment, the device 500 is still implanted in a partially open position illustrated by FIGS. 48A and 48B, but the implanted device is configured to open further than the illustrated partially open position as the native valve leaflets open during the cardiac cycle. This is yet another exemplary embodiment of permitting more flexibility of the native valve leaflets upon implantation of a prosthetic implant device to maintain a low-pressure gradient between the atrium and ventricle.

Referring now to FIGS. 49A-50B, exemplary embodiments of an implantable prosthetic device 500 are illustrated, having inner and outer paddles 522, 520, inner and outer clasps 534, 532, and a coaption device 510. The coaption device, paddles, clasps, and frame of the device in FIG. 49A can have the same characteristics as that of the embodiment described with respect to FIG. 47A, but does not have the biasing component that applies a force to close the paddles 522, 520 and attached clasps in the direction towards the coaption element. In this and other exemplary embodiments without an additional biasing component, the paddles and/or clasps can be made of a shape memory material or can be otherwise biased in a closed position toward the center of the device and/or coaption element. In the embodiment of a shape memory metal, the paddles and/or clasps can be set so that they are biased toward the closed position, and open when the force of the blood flow on the leaflets forces the leaflets open. Thus, the force provided by the paddles and/or clasps (or by the biasing component, depending on the embodiment) that holds the clasps shut can be overcome by the pressure of blood on the leaflets during diastole to open the device 500 and the native valve leaflets. The force to close the device, provided by the elements of the device itself and/or the force of the pressure of the blood (during the systolic contraction of the ventricle), is great enough, to close the device closed during systole.

Figure 49A:
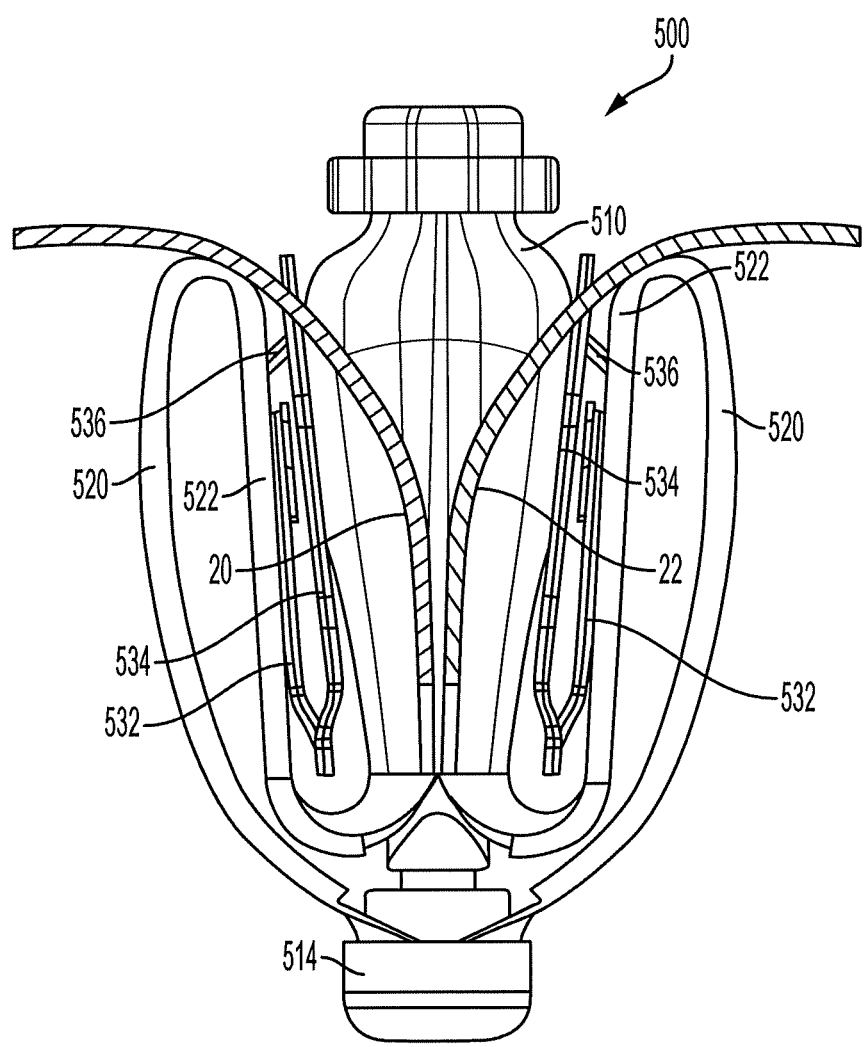
FIG. 49A shows a schematic view of a path of mitral valve leaflets along each side of an exemplary embodiment of a mitral valve repair device having clasps and a coaption element in a closed position.

FIG. 49A illustrates the geometry of the coaption element, taken from a cross-section farther toward a forward facing side view rather than from the center. In this cross-section, offset from the center of the device, the leaflets 20, 22 are shown to be wrapped around the coaption element. In the center, the leaflets 20, 22 are positioned between the inner clasp 534 and outer clasp 532 on each side of the device. As can be seen in this view, the coaption element 510 has a tapered shape being smaller in dimension in the area closer to where the inside surfaces of the leaflets 20, 22 are required to coapt and increase in dimension as the coaption element extends toward the atrium. The depicted native valve geometry is accommodated by a tapered coaption element geometry.

Figure 49B:
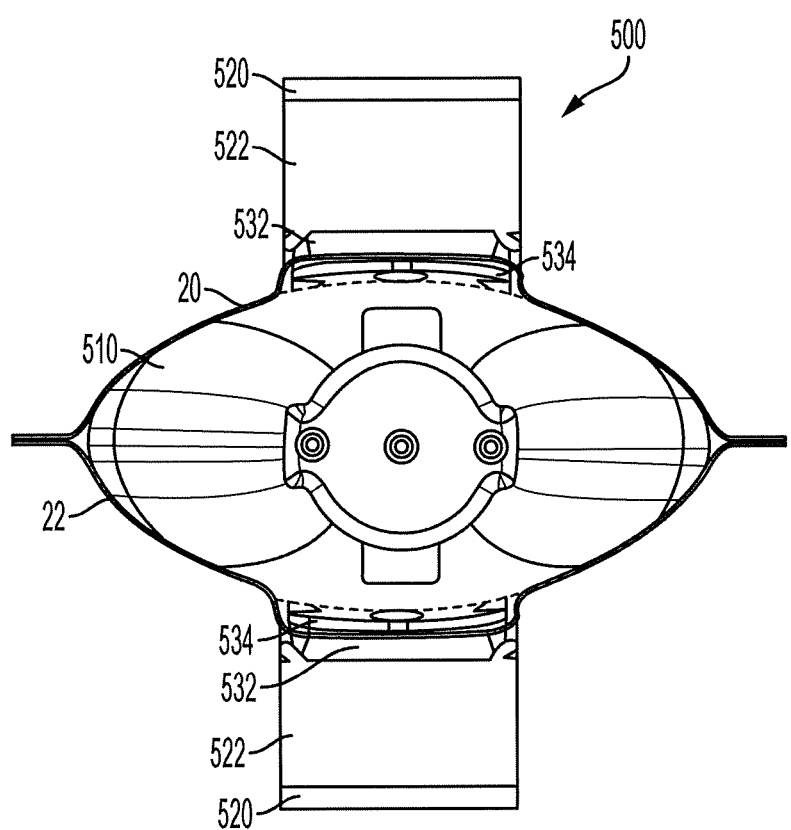
FIG. 49B shows a cross-section of the exemplary embodiment of FIG. 49A.

Referring to FIG. 49B, a schematic atrial view depicts the paddles 522, 520 and the inner and outer clasps 534, 532 (the outer clasps 532 would not actually be visible from a true atrial view), with a central region of each leaflet positioned in between the inner and outer clasps. The sides of the leaflets are not grasped or fixed in between any component of the device and when in a closed position, such as during ventricular systole, surround or "hug" the coaption element and can conform to the geometry of the coaption element.

Figure 50A:
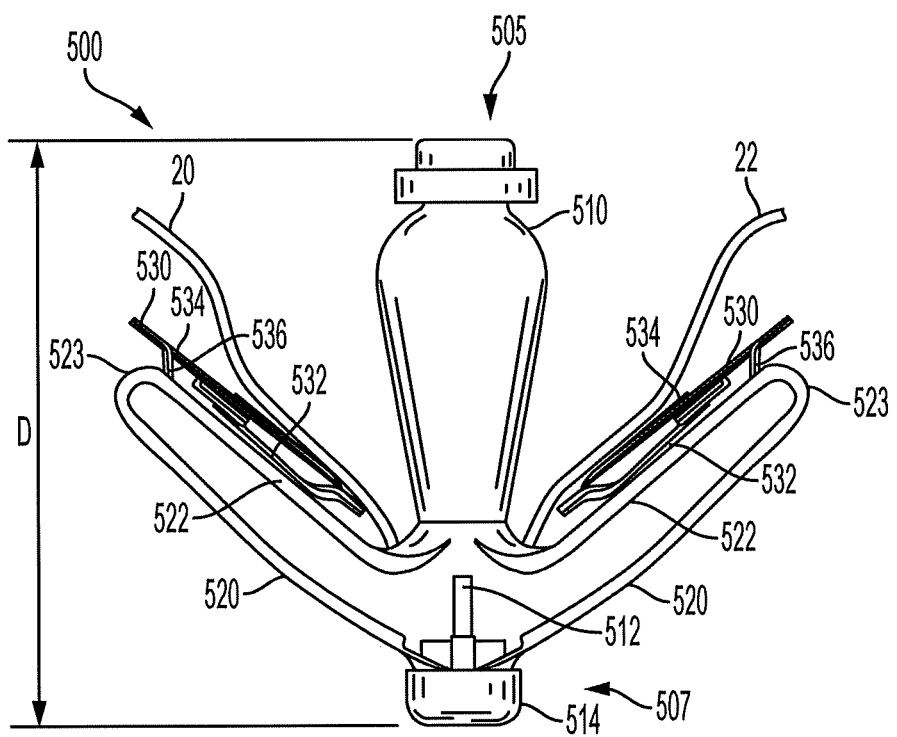
FIG. 50A shows a schematic view of a path of mitral valve leaflets along each side of an exemplary embodiment of a mitral valve repair device having clasps and a coaption element where the device is in an open position and the leaflets are open.
Figure 50B:
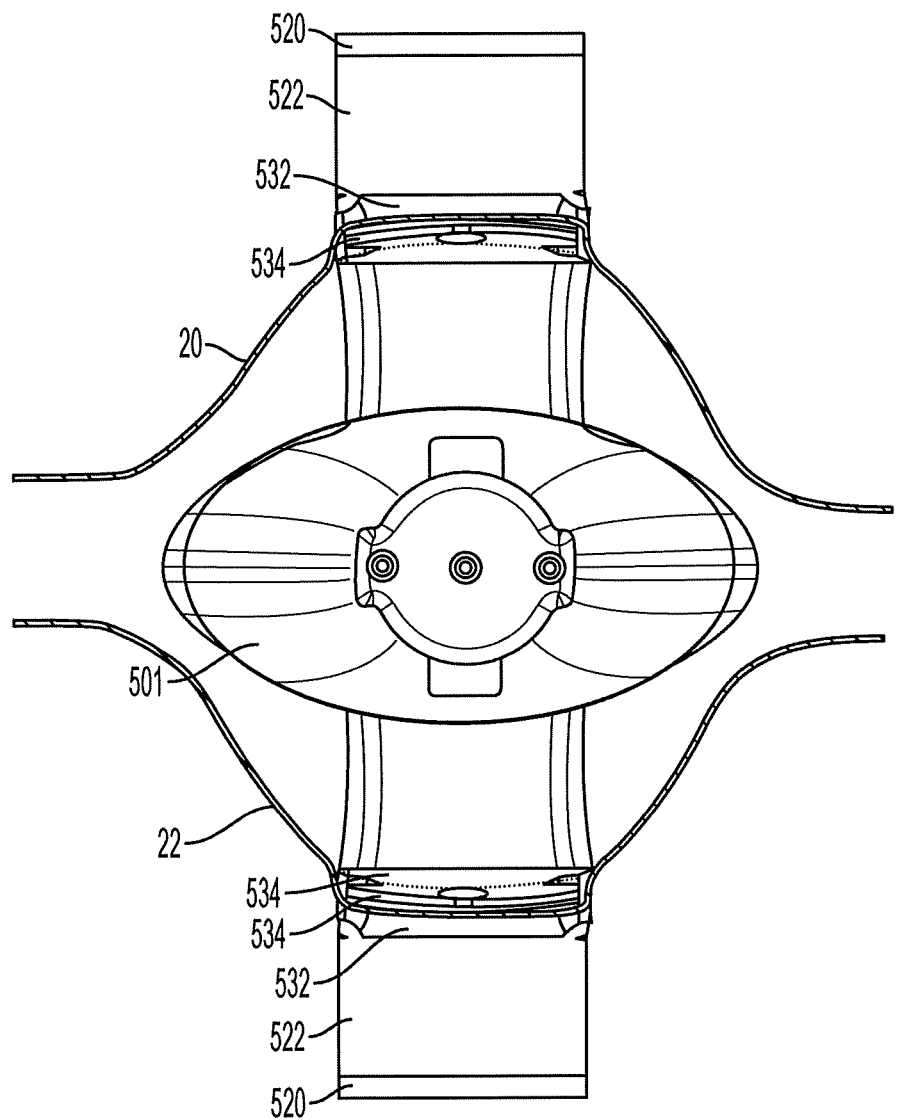
FIG. 50B shows a cross-section of the exemplary embodiment of FIG. 50A.

FIGS. 50A and 50B illustrate the device of FIGS. 49A and 49B where the pair of paddles 522, 520 are in a partially open position. The clasps 532, 534 are moved with the pair of paddles 520, 522 to the coaption element 510 to the illustrated partially open position. In FIG. 50A, a cross-section is taken farther toward a forward facing side of the device, rather than from the center to show the positions of the valve leaflets in front of the device, rather than the portion of the leaflets that is secured by the clasps. In this cross-section, offset from the center of the device, the leaflets 20, 22 are open to permit blood flow from the left atrium to the left ventricle, with the coaption element in the middle of the valve. In the center, as seen from the point of view in FIG. 50B, the leaflets 20, 22 are positioned between the inner clasp 534 and outer clasp 532 on each side of the device. The clasps can be connected to the coaption element and/or cap as in the exemplary embodiments described herein. The clasps are pivoted away from the coaption element by the paddles in the open position illustrated in FIG. 50A.

FIG. 50B illustrates a top-down view of the device shown in FIG. 50A. A schematic atrial view depicts the inner and outer paddles 522, 520, the inner and outer clasps 534, 532 (the outer clasps 532 would not be visible from a true atrial view, but included in this figure for reference), and coaption element 510, with a central region of each leaflet positioned in between the inner and outer clasps in an open position. The opposing leaflets 20, 22 (the ends of which would not be visible in a true atrial view) are each held between an inner clasp 534 and an outer clasp 532. In this view, the leaflets are open to permit blood flow from the left atrium to the left ventricle.

The partially open position illustrated in FIGS. 50A and 50B depicts an embodiment where the paddles can open and close throughout the cardiac cycle. In this embodiment, FIGS. 50A and 50B illustrates the paddles in the "open" position, which occurs during ventricular diastole when the mitral valve leaflets are in an open position to permit blood flow from the left atrium to the left ventricle. As such, the paddles 520, 522 of the device 500 open and close with the opening and closing of the native valve leaflets during the cardiac cycle in one exemplary embodiment.

Figure 50C:
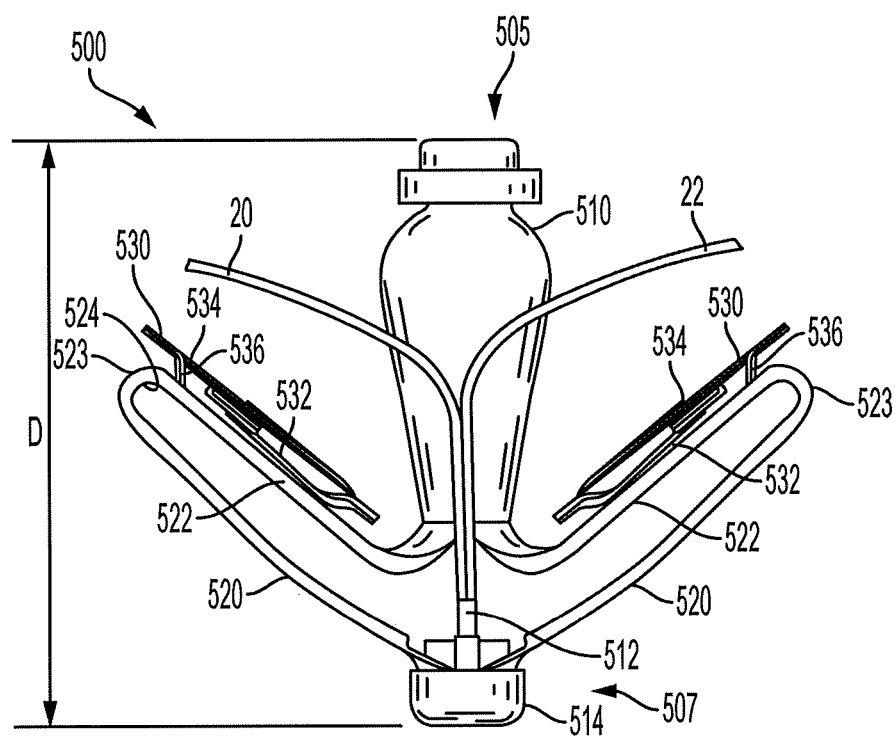
FIG. 50C shows a schematic view of a path of mitral valve leaflets along each side of an exemplary embodiment of a mitral valve repair device having clasps and a coaption element where the device is in an open position and the leaflets are closed.
Figure 50D:
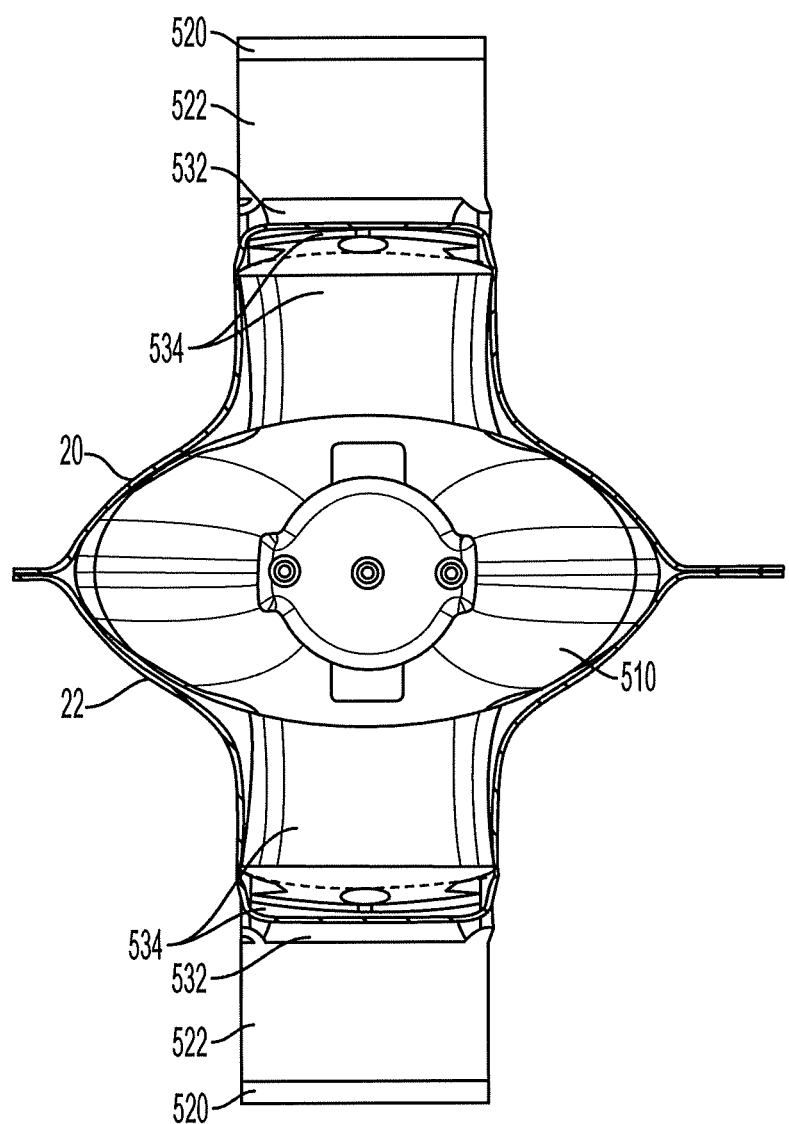
FIG. 50D shows a cross-section of the exemplary embodiment of FIG. 50C.

In another exemplary embodiment, when the leaflets close such as during systole, the paddles can remain in an "open" position. FIGS. 50C and 50D illustrate the embodiment having paddles deployed in a fixed partially open condition, with closed leaflets during systole. When the leaflets close, the paddles 524, 524 remain in the deployed partially open position. The central region of each of the leaflets remains fixed between the inner and outer clasps, and the sides of the leaflets approximate the coaption element 510 as illustrated in FIG. 50C. The leaflets are closed and a greater portion of the leaflets are coapted together and to the coaption element.

FIG. 50D represents a top-down view of the device shown in FIG. 50C. A schematic atrial view depicts the paddles in the deployed, partially open position of FIG. 50C. The opposing leaflets 20, 22 are each held between an inner clasp 534 and an outer clasp 532. In this view, the leaflets 20, 22 are closed and approximated to the coaption element 510, to prevent blood flow from the left atrium to the left ventricle. As such, the native valve leaflets open and close in the cardiac cycle and the deployed device remains in a deployed, partially open position.

In yet another exemplary embodiment, the device 500 is still implanted in a partially open position illustrated by FIGS. 50A and 50B, but the implanted device is configured to open further than the illustrated partially open position as the native valve leaflets open during the cardiac cycle. This is yet another exemplary embodiment of permitting more flexibility of the native valve leaflets upon implantation of a prosthetic implant device to maintain a low-pressure gradient between the atrium and ventricle.

Referring now to FIGS. 51A-52B, exemplary embodiments of an implantable prosthetic device 500 are illustrated, where the device has inner and outer clasps 534, 532, inner and outer paddles 522, 520, and an additional biasing member 524 on each side. The clasps, and paddles of the device in FIG. 51A can have the same characteristics as that of the embodiment described with respect to FIG. 47A, but does not have the coaption element for the leaflets to conform to when the mitral valve is in a closed position. The anatomy of the leaflets 20, 22 is such that the inner sides of the leaflets coapt and the leaflets 20, 22 start receding or spreading apart from each other. The leaflets 20, 22 spread apart in the atrial direction, until each leaflet meets with the mitral annulus.

Figure 51A:
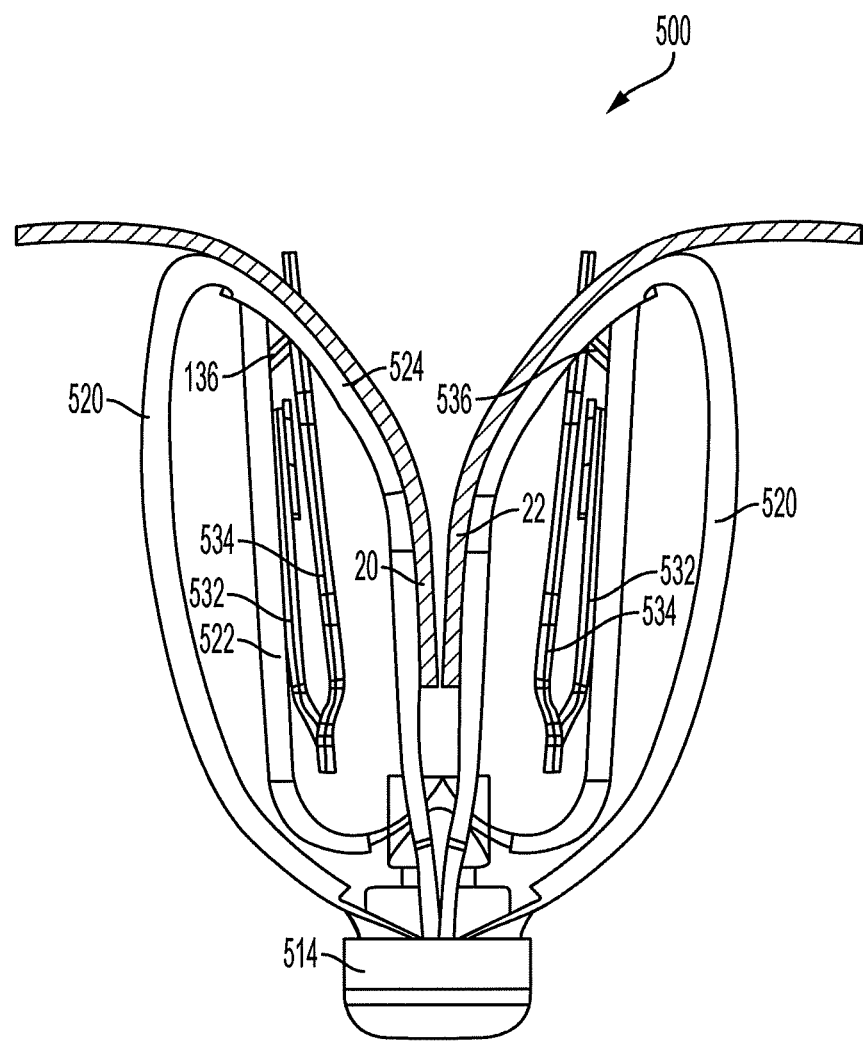
FIG. 51A shows a schematic view of a path of mitral valve leaflets along each side of an exemplary embodiment of a mitral valve repair device having clasps and a paddle frame in a closed position.
Figure 51B:
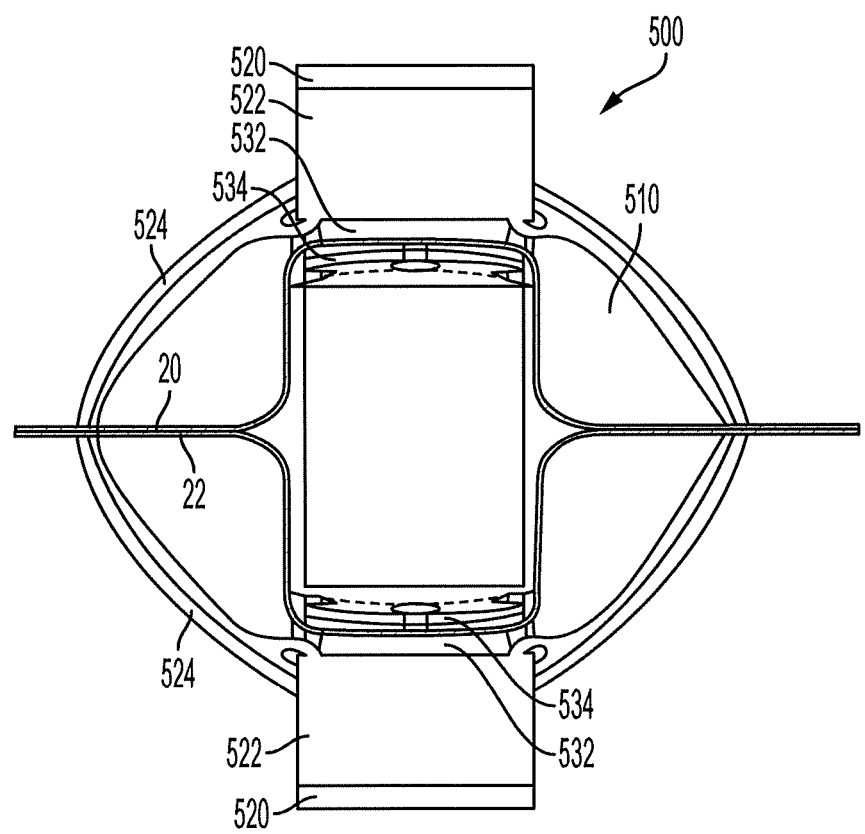
FIG. 51B shows a cross-section of the exemplary embodiment of FIG. 51A.

FIGS. 51A and 51B illustrate an exemplary embodiment of an implantable prosthetic device in a closed position, during ventricular systole when the mitral valve leaflets are closed.

FIG. 51A illustrates the geometry of the clasps 534, 532, paddles 522, 520 and biasing members 524, taken from a cross-section farther toward a forward facing side view rather than from the center. The leaflets 20, 22 are approximated together, and conform to the geometry of the biasing members 524 in this cross-section, which is offset from the center of the device 500. In the center, the leaflets 20, 22 are positioned between the inner clasp 534 and outer clasp 532 on each side of the device.

Referring now to FIG. 51B, a schematic atrial view depicts the inner and outer clasps 534, 532 (the outer clasps 532 would not be visible from a true atrial view) and paddles 522, 520 (in the closed device, closed leaflet configuration, the outer paddles would not be visible from a true atrial view), with a central region of each leaflet fixed between the inner and outer clasps. The sides of the leaflets are not grasped or fixed in between any component of the device and when in a closed position, such as during ventricular systole, close toward and approximate each other, closer together near the edges of the leaflets than at the portion of the leaflets closer to the annulus. The biasing members 524 can provide a force pushing the clasps to the closed position shown in FIGS. 51A and 51B, assisting in approximating the center region of the leaflets together.

Figure 52A:
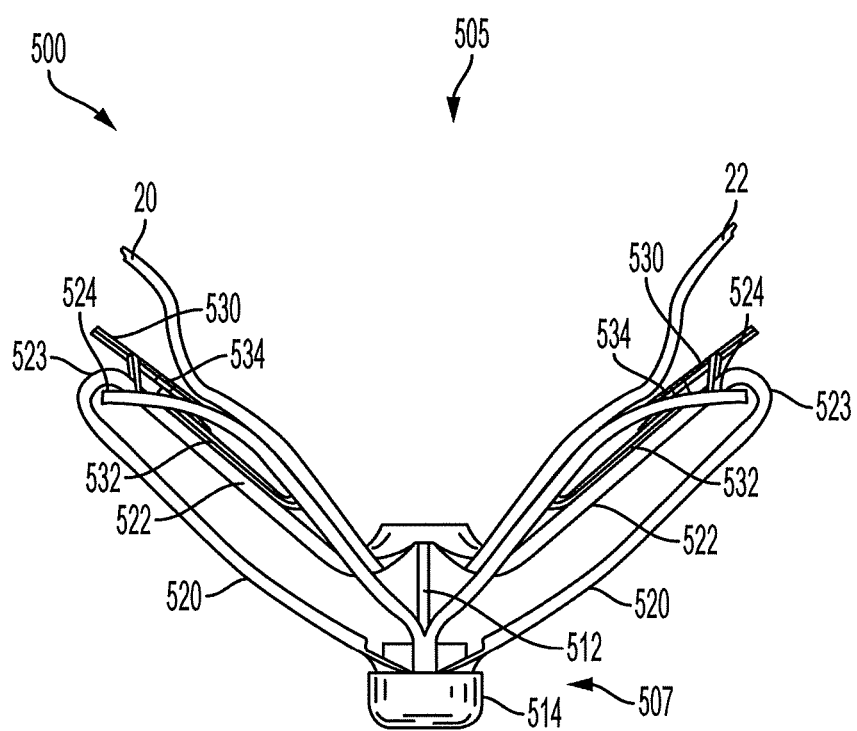
FIG. 52A shows a schematic view of a path of mitral valve leaflets along each side of an exemplary embodiment of a mitral valve repair device having clasps and a paddle frame where the device is in an open position and the leaflets are open.
Figure 52B:
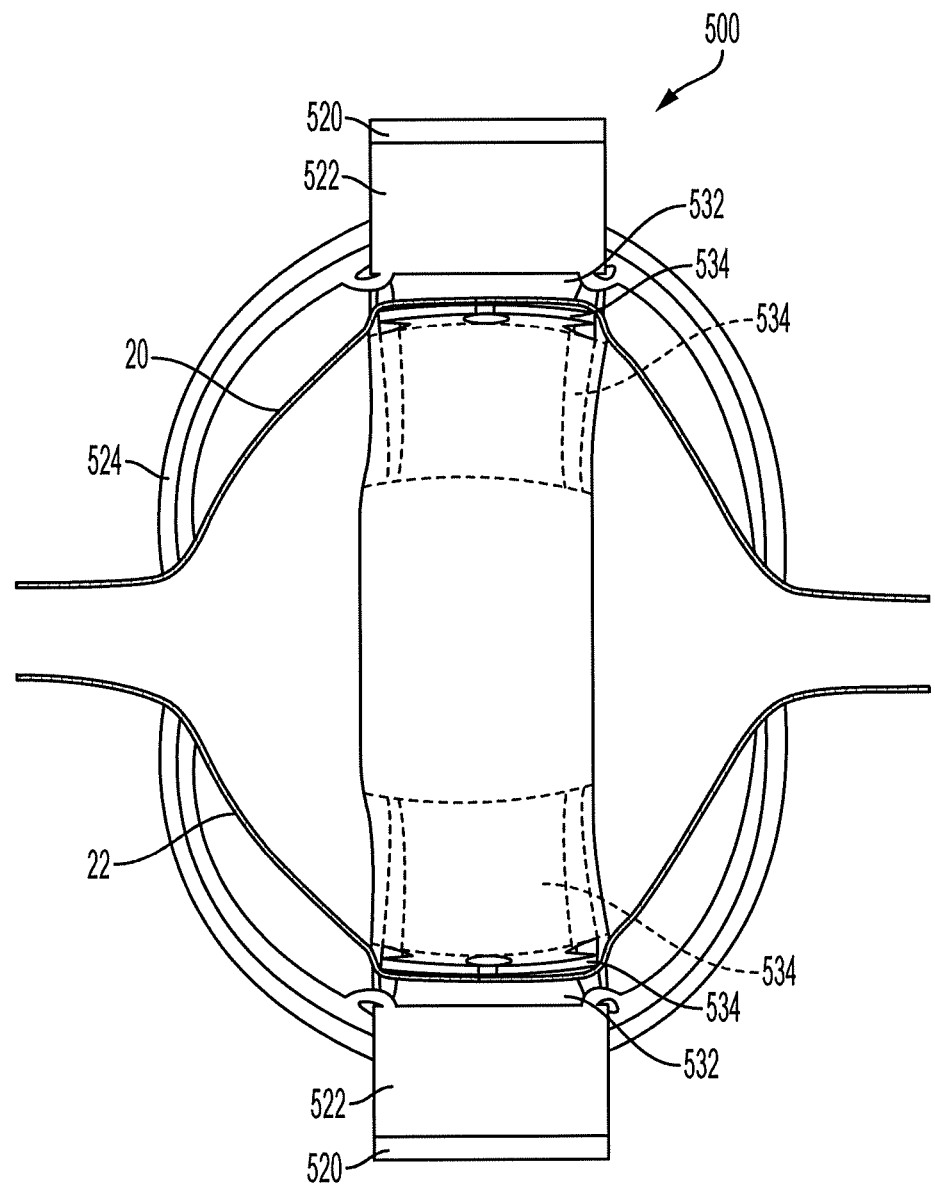
FIG. 52B shows a cross-section of the exemplary embodiment of FIG. 52A.

Referring now to FIGS. 52A and 52B, the device of FIGS. 51A and 51B is illustrated as being in a partially open configuration. In this example, the paddles, and biasing components of the device are in an open position, and the leaflets are open as occurs during ventricular diastole, is illustrated. In FIG. 52A, the coaption element 510 and the biasing members 524 from a cross-sectional view, taken from a cross-section farther toward a forward facing side view rather than from the center. In this cross-section, offset from the center of the device, the side regions of leaflets 20, 22 are shown. In the center, not seen from the point of view in FIG. 52A, the leaflets 20, 22 are positioned between the inner clasp 534 and outer clasp 532 on each side of the device. The clasps, paddles, and biasing members can be connected to the cap 514 or other distal portion of the device 500. The clasps and paddles are pivoted away from the coaption element in the open position illustrated in FIG. 52A.

FIG. 52B illustrates a top-down view of the device shown in FIG. 52A. A schematic atrial view depicts the inner and outer paddles 522, 520 (which would not be visible from a true atrial view), the inner and outer clasps 534, 532 (the outer clasps would not be visible from a true atrial view but are added here for a better understanding of the device), and biasing members 524, in an open position. The opposing leaflets 20, 22 (the ends of which would also not be visible in the true atrial view) are each held between an inner clasp 534 and an outer clasp 532. In FIG. 52B, the leaflets are open as in ventricular diastole so that blood flows from the left atrium to the left ventricle.

The open position of the device 500 illustrated in FIGS. 52A and 52B depicts the open position of an embodiment where the clasps and paddles can open and close throughout the cardiac cycle along with the native valve leaflets 20. The open position can occur during ventricular diastole, where the mitral valve leaflets are in an open position to permit blood flow from the left atrium to the left ventricle. FIGS. 52A and 52B are the open device position and open leaflets of. The closed device and closed leaflets are illustrated in FIGS. 51A and 51B.

FIGS. 52A and 52B are also representative of another embodiment where the clasps and paddles are deployed in a fixed, partially open position that is maintained during the cardiac cycle. In this embodiment, FIGS. 52A and 52B illustrate the device and mitral valve leaflets during ventricular diastole, where blood flows from the atrium to the ventricle.

Figure 52C:
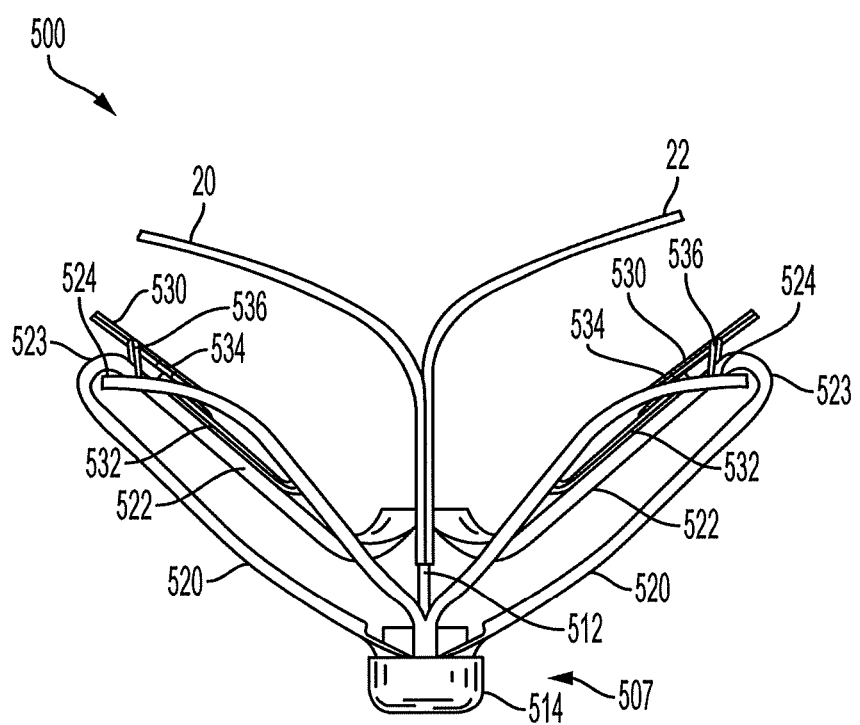
FIG. 52C shows a schematic view of a path of mitral valve leaflets along each side of an exemplary embodiment of a mitral valve repair device having clasps and a paddle frame where the device is in an open position and the leaflets are closed.
Figure 52D:
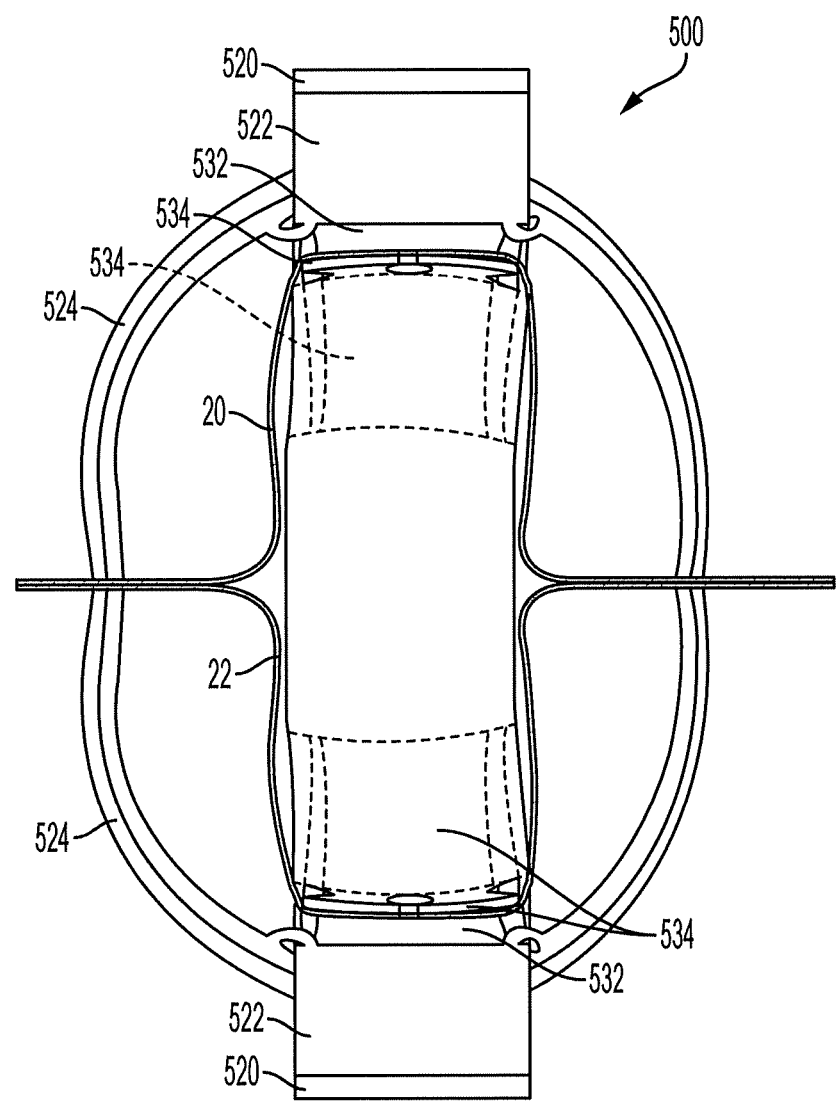
FIG. 52D shows a cross-section of the exemplary embodiment of FIG. 52C.

FIGS. 52C and 52D illustrate the device of FIGS. 52A and 52B according to the exemplary embodiment where the device remains in a partially open position throughout the cardiac cycle, even when the leaflets are closed as occurs during ventricular systole. In this embodiment, when the leaflets close, the inner and outer clasps 534, 532 and inner and outer paddles 522, 520, remain in an open position. As explained above with respect to other embodiments described herein, the leaflets close due to the force applied to the leaflets from the blood pressure in the ventricle, and the force applied by the additional biasing members 524. The central region of each of the leaflets remains fixed between the inner and outer clasps, and the sides of the leaflets approximate each other as illustrated in FIG. 52D.

In yet another exemplary embodiment, the device 500 is still implanted in a partially open position illustrated by FIGS. 52A and 52B, but the implanted device is configured to open further than the illustrated partially open position as the native valve leaflets open during the cardiac cycle. This is yet another exemplary embodiment of permitting more flexibility of the native valve leaflets upon implantation of a prosthetic implant device to maintain a low-pressure gradient between the atrium and ventricle.

Referring now to FIGS. 53A-54B, exemplary embodiments of an implantable prosthetic device 500 are illustrated, having inner and outer clasps 534, 532, and paddles 522, 520 around the clasps for attachment of the clasps to a central cap region of the implantable prosthetic device. The clasps, and paddles of the device in FIG. 53A can have the same characteristics as that of the embodiment described with respect to FIG. 47A, but does not have a coaption element or additional biasing component to hold the clasps in a closed position. In another exemplary embodiment, the clasps and/or paddles can be wider than illustrated in FIGS. 53A-54B. In another exemplary embodiment, the width of each of the clasps and/or paddles can vary along the length of each of the clasps/paddles. By providing these variations in width of the clasps and/or paddles, a greater surface area for the leaflet to contact is provided. The wider clasps and/or paddles, and varying width clasps and/or paddles can be a feature in any of the embodiments described herein.

Figure 53B:
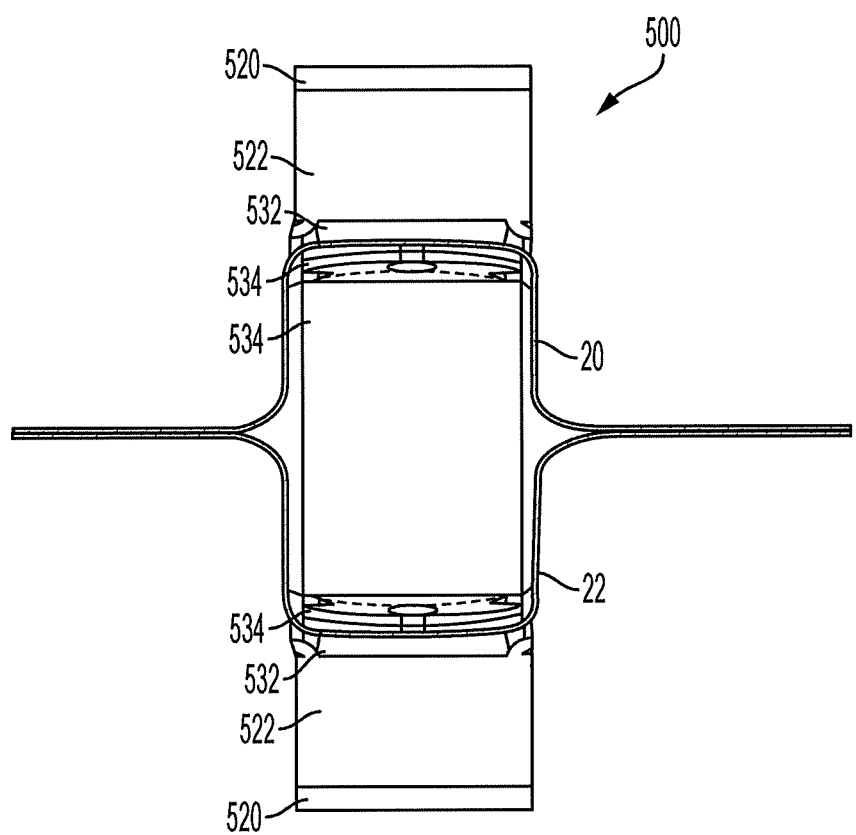
FIG. 53B shows a cross-section of the exemplary embodiment of FIG. 53A.

FIGS. 53A and 53B illustrate an exemplary embodiment of an implantable prosthetic device in a closed position, during ventricular systole when the mitral valve leaflets are closed.

FIG. 53A illustrates the geometry of the paddles 522, 520, taken from a cross-section farther toward a forward facing side view rather than from the center. In this cross-section, offset from the center of the device, the leaflets 20, 22 are shown approximated together. In the center, the leaflets 20, 22 are positioned between the inner clasp 534 and outer clasp 532 on each side of the device.

Referring now to FIG. 53B, a schematic atrial view depicts the inner and outer clasps 534, 532 (the outer clasps 532 would not actually be visible from a true atrial view), with a central region of each leaflet fixed between the inner and outer clasps. The sides of the leaflets are not grasped or fixed in between any component of the device and when in a closed position, such as during ventricular systole, approximate each other, at the edges of the leaflets rather than at the portion of the leaflets closer to the annulus. The leaflets are approximated together during systole by the force of the blood pressure in the ventricle against the ventricular surface of the leaflets.

Figure 54A:
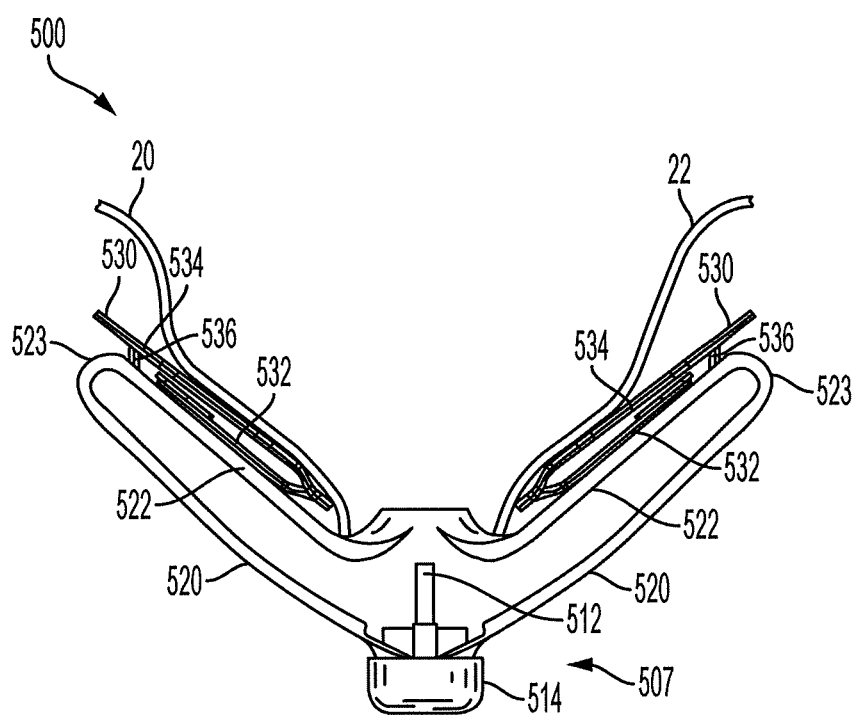
FIG. 54A shows a schematic view of a path of mitral valve leaflets along each side of an exemplary embodiment of a mitral valve repair device having clasps where the device is in an open position and the leaflets are open.
Figure 54B:
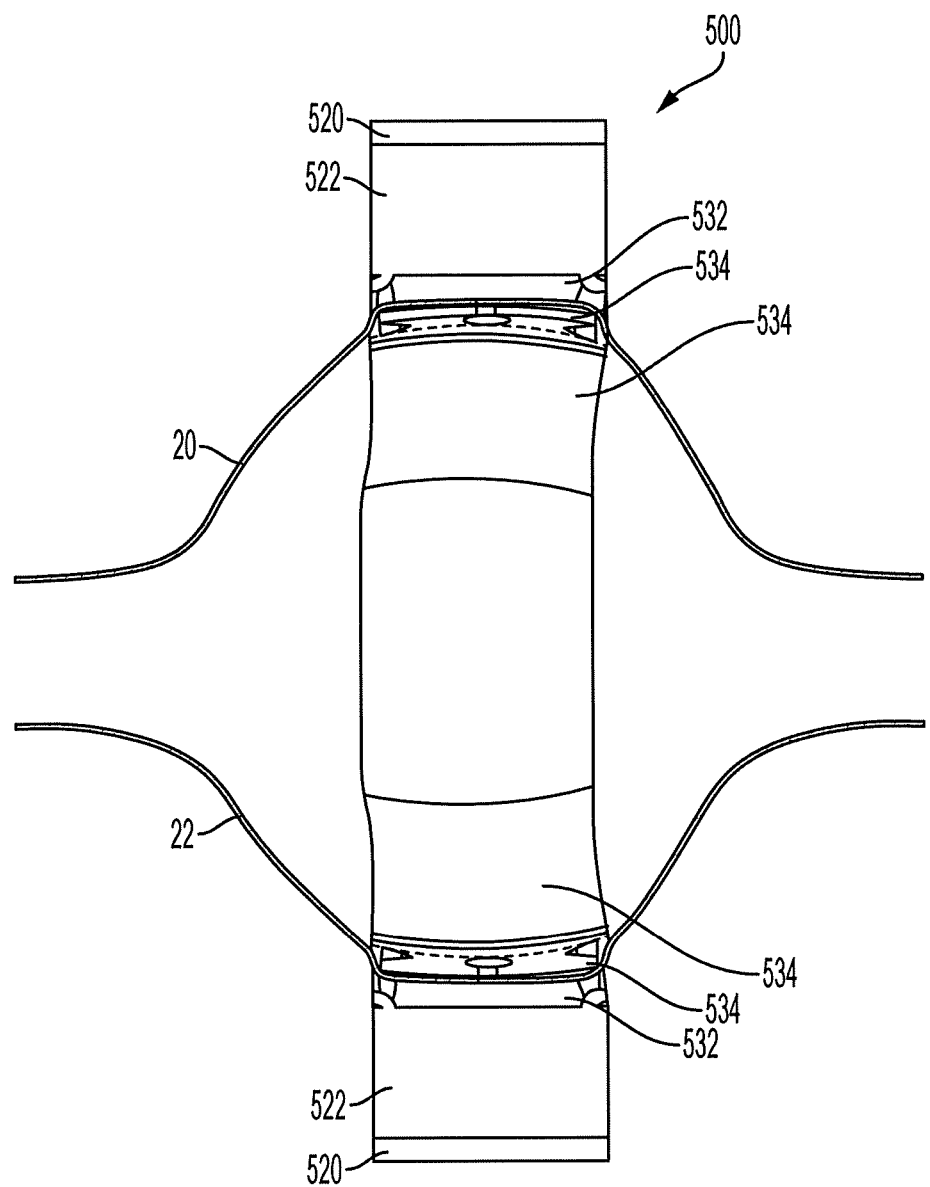
FIG. 54B shows a cross-section of the exemplary embodiment of FIG. 54A.

Referring now to FIGS. 54A and 54B, the device of FIGS. 53A and 53B is illustrated as being in a partially open configuration. In the example illustrated by FIGS. 54A and 54B, the paddles are in the partially open position and the leaflets are open due to the blood flow during ventricular diastole, is illustrated. In FIG. 54A, a cross-section view of the device farther toward a forward facing side, rather than through the center, is illustrated. In this cross-section, offset from the center of the device, the side regions of leaflets 20, 22 are shown, and they are positioned apart from each other. In the center, as shown in FIG. 54B, the leaflets 20, 22 are positioned between the inner clasp 534 and outer clasp 532 on each side of the device. The paddles can be connected to the cap 514 or other distal portion of the device 500. The paddles and attached clasps are pivoted away from the coaption element in the open position illustrated in FIG. 54A.

FIG. 54B illustrates a top-down view of the device shown in FIG. 54A. A schematic atrial view depicts the paddles 522, 520 (which would not actually be visible from a true atrial view), and the inner and outer clasps 534, 532 (the outer clasps would not be visible from a true atrial view), in an open position. The opposing leaflets 20, 22 (the ends of which would also not be visible in the true atrial view) are each held between an inner clasp 534 and an outer clasp 532. In FIG. 54B, the leaflets are open as in ventricular diastole so that blood can flow from the left atrium to the left ventricle.

The open position of the device 500 illustrated in FIGS. 54A and 54B depicts the open position of an embodiment where the clasps can open and close throughout the cardiac cycle. In this embodiment, FIGS. 54A and 54B illustrate when the clasps of the device are in the open position. The open position can occur during ventricular diastole, when the mitral valve leaflets are in an open position to permit blood flow from the left atrium to the left ventricle. FIGS. 54A and 54B the open device position and open leaflets that correspond to diastole. The closed device and closed leaflet that correspond to ventricular systole are illustrated in FIGS. 53A and 53B. As such, the paddles of the device open and close with the native valve leaflets during the cardiac cycle.

FIGS. 54A and 54B are also representative of an embodiment where the clasps and paddles are deployed in and remain fixed in a partially open position during the cardiac cycle. In this embodiment, FIGS. 54A and 54B illustrate the device and mitral valve leaflets during ventricular diastole.

Figure 54C:
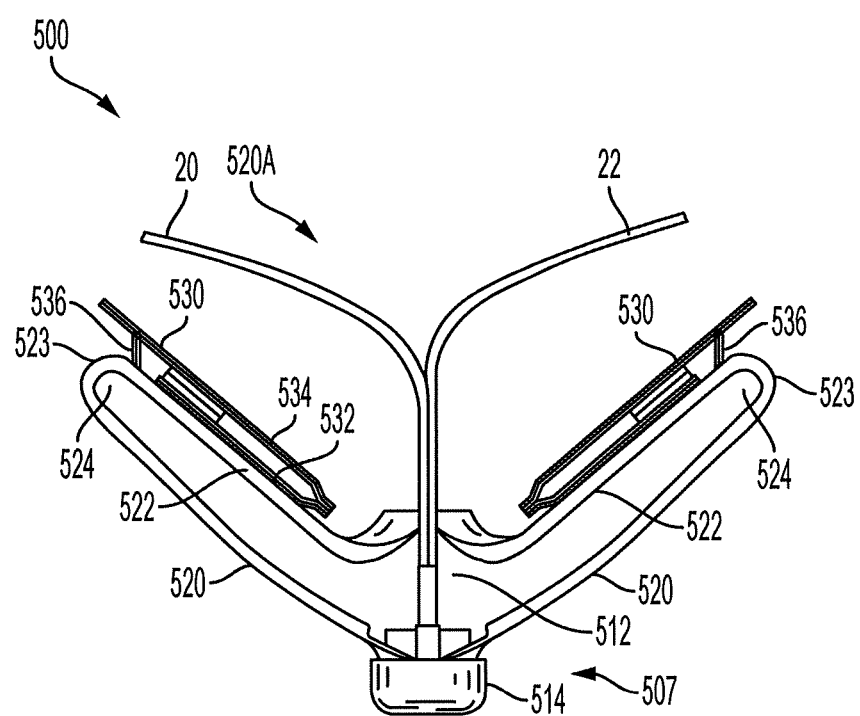
FIG. 54C shows a schematic view of a path of mitral valve leaflets along each side of an exemplary embodiment of a mitral valve repair device having clasps where the device is in an open position and the leaflets are closed.
Figure 54D:
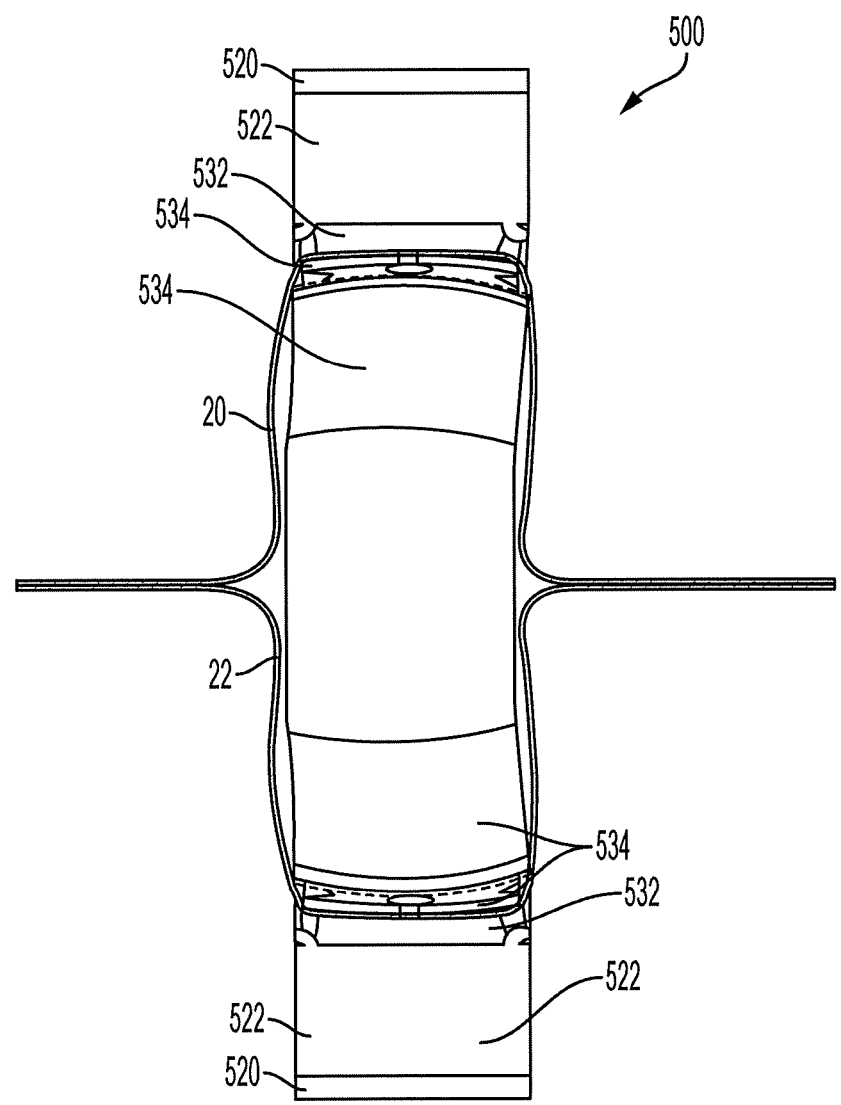
FIG. 54D shows a cross-section of the exemplary embodiment of FIG. 54C.

FIGS. 54C and 54D illustrate the device of FIGS. 54A and 54B when the leaflets are in closed, as occurs during ventricular systole. In this embodiment, when the leaflets close, the paddles remain in an open position. The leaflets close due to the force applied to the leaflets from the blood pressure in the ventricle. The central region of each of the leaflets remains fixed between the inner and outer clasps, and the sides of the leaflets approximate each other.

Figure 55:
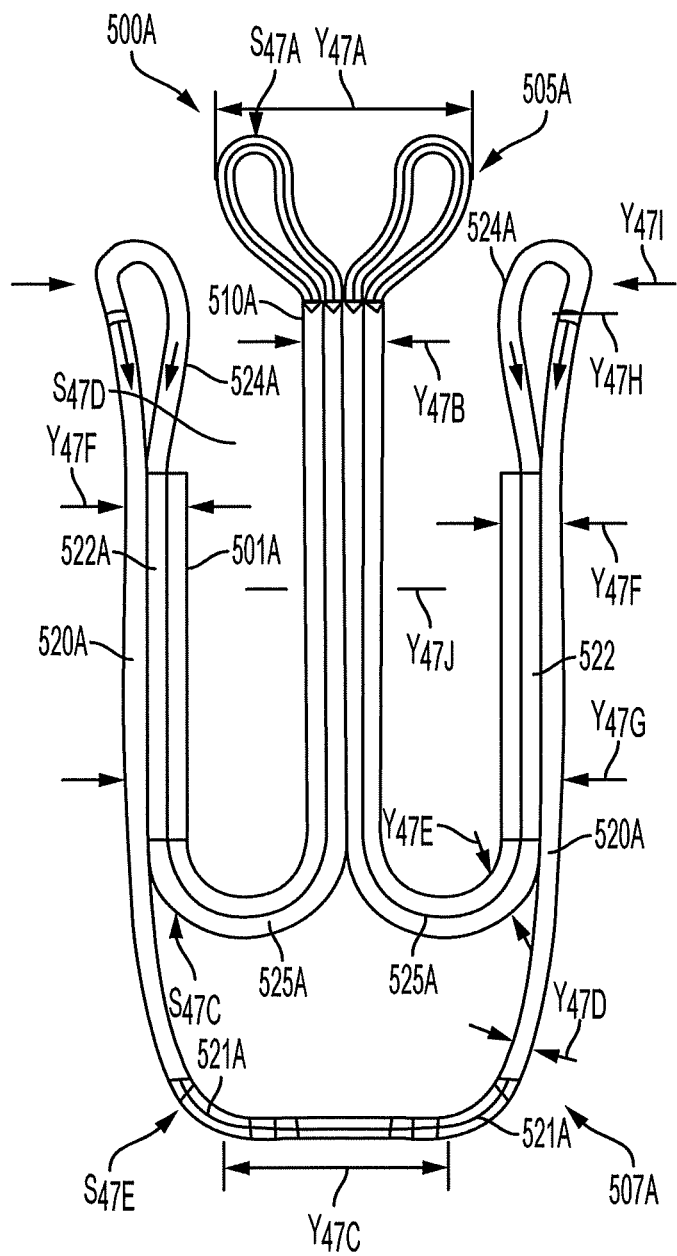
FIG. 55 shows an exemplary implantable prosthetic device without barbed clasps or biasing members in a closed position.

Referring now to FIG. 55, another exemplary embodiment of an implantable prosthetic device is illustrated. FIG. 55 illustrates a device 500A formed from a continuous strip of a braided or woven material, such as braided or woven nitinol wire. The device 500A can be configured to open and close with the native valve leaflets, can be configured to be deployed with the paddles in a partially open position and the paddles remain fixed in the deployed, partially open position during the cardiac cycle, and/or can be configured to be deployed with the paddles in a partially open position and the paddles open further from the partially open position and return to the deployed position during the cardiac cycle in any of the manners described above with respect to any of the other devices described above.

Figure 55A:
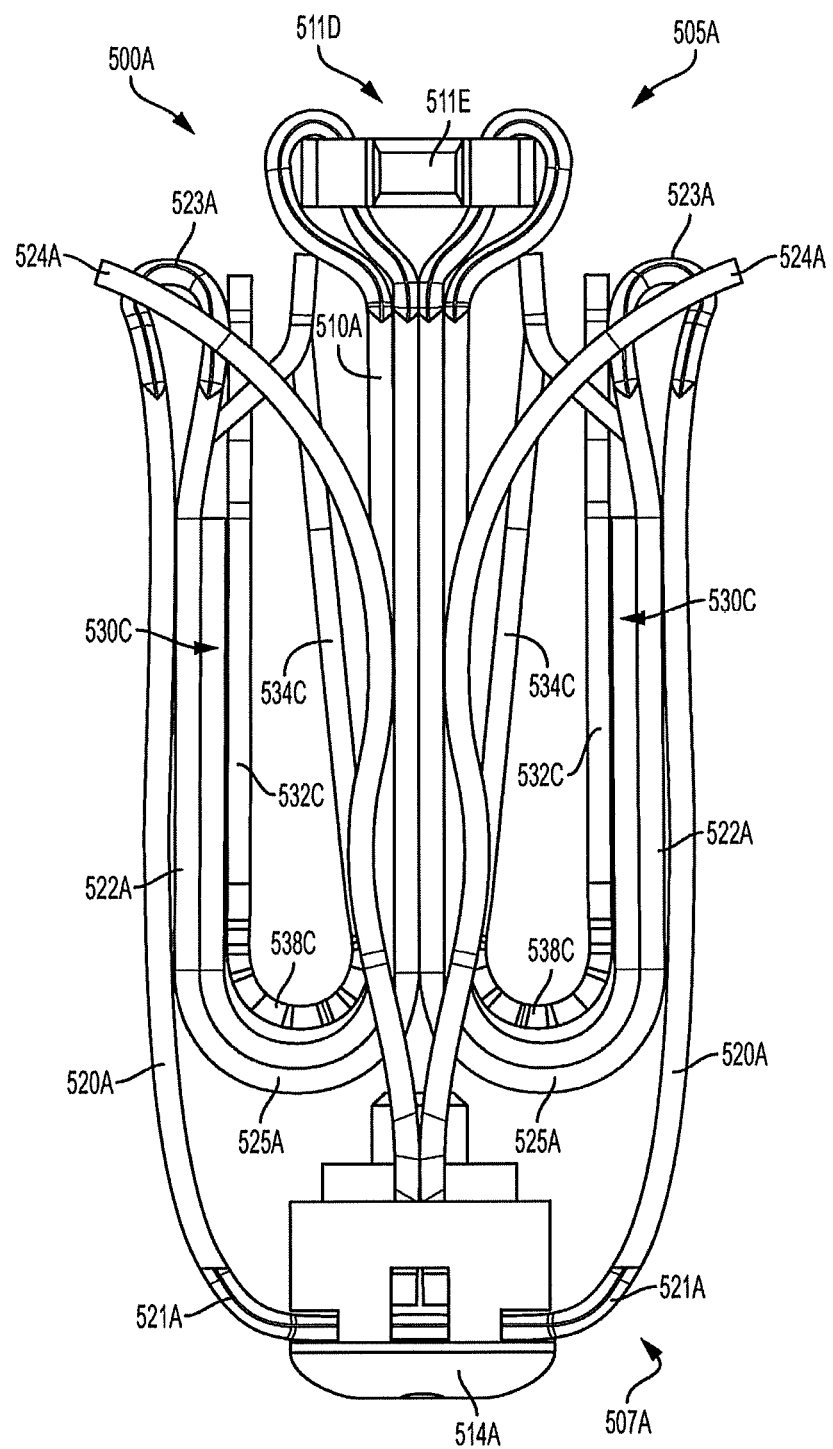
FIG. 55A shows an exemplary implantable prosthetic device with clasps, a collar, and a cap in a closed position.

Referring to FIG. 55A, the continuous strip 501A is attached to a collar 511D, a cap 514A, and clasps 530C. In the illustrated embodiment, the coaption element 510A, hinge portions 521A, 523A, 525A, outer paddles 520A, and inner paddles 522A are formed from the continuous strip 501A. The continuous strip 501A may be a single layer of material or may include two or more layers. In certain embodiments, portions of the device 500A have a single layer of the strip of material 501A and other portions are formed from multiple overlapping or overlying layers of the strip of material 501A. For example, FIG. 55 shows the coaption element 510A and inner paddles 522A formed from multiple overlapping or overlying layers of the strip of material 501A. Consequently, the coaption element 510A and inner paddle 522A have an increased stiffness relative to the outer paddles 520A that are formed from a single layer of material 501A. The single continuous strip of material 501A can start and end in various locations of the device 500A. The ends of the strip of material 501A can be in the same location or different locations of the device 500A. For example, in the illustrated embodiment of FIG. 55, the strip of material begins and ends in the location of the inner paddles 522.

The clasps 530C can comprise attachment or fixed portions 532C, arm or moveable portions 534C, barbs 536C, and joint portions 538C. The attachment or fixed portions 532C can be coupled to the inner paddles 522A in various ways such as with sutures, adhesive, fasteners, welding, stitching, swaging, friction fit and/or other means for coupling with the joint portions 538C disposed proximate the coaption element 510A.

The moveable portions 534C can pivot or flex relative to the fixed portions 532C between an open configuration (e.g., FIG. 49A) and a closed configuration (FIG. 50A). In some embodiments, the clasps 530C can be biased to the closed configuration. In the open configuration, the fixed portions 532C and the moveable portions 534C pivot or flex away from each other such that native leaflets can be positioned between the fixed portions 532C and the moveable portions 534C. In the closed configuration, the fixed portions 532C and the moveable portions 534C pivot or flex toward each other, thereby clamping the native leaflets between the fixed portions 532C and the moveable portions 534C. The fixed arms 532C remain substantially stationary when the moveable arms 534C are opened to open the barbed clasps 530C and expose the barbs 536C. The barbed clasps 530C are opened by applying tension to actuation lines 516A attached to the moveable arms 534C, thereby causing the moveable arms 534C to pivot or flex on the joint portions 538C.

The device 500A in FIG. 55 is shown in a closed position. From the side, the device 500A has a generally inverted trapezoidal shape that is rounded and tapers toward the distal portion 507A of the device 500A.

In the closed configuration of the device 500A, the inner paddles 522A are disposed between the outer paddles 520A and the coaption element 510A. In some embodiments, the device 500A includes clasps or gripping members 530C that can be opened and closed to grasp the native leaflets 20, 22 of the mitral valve MV. The clasps 530C are attached to and move with the inner paddles 522A and are disposed between the inner paddles 522A and the coaption element 510A.

The embodiment shown in FIG. 55 can be used according to any of the exemplary embodiments described herein. That is, the device can open with the opening of the leaflets, for example as illustrated in FIG. 50A. The device can also remain in a partially open position during the cardiac cycle, as illustrated in FIGS. 50A-50D, for example. Further, the device can be implanted with the paddles partially open and the paddles can move back and forth between the deployed position and a further open position with the cardiac cycle. Further, the device can be made of a flexible material such as that described herein with respect to FIGS. 59A-59B.

The device 500A illustrated in FIG. 55, shown in a closed position, can also pivot open, due to flexible regions 525A and 521A. As with the other embodiments described above, when the mitral valve leaflets are closed, the device 500A is in a closed position as shown in FIG. 55. The device in FIG. 55 can be in an open position (not shown) when the leaflets are open such as during ventricular diastole. The device of FIG. 55 can also remain in an open configuration throughout the cardiac cycle. In such an embodiment, the leaflets coapt together during systole, as illustrated with respect to other embodiments described herein (see for example FIGS. 50C-50D).

Figure 56A:
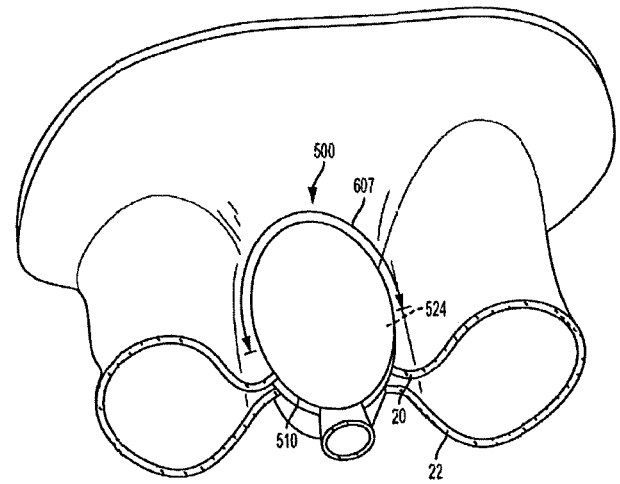
FIGS. 56A-56B each show a perspective view of a valve repair device attached to mitral valve leaflets with a coaption element in the gap of the mitral valve shown from a ventricular side of the heart.
Figure 56B:
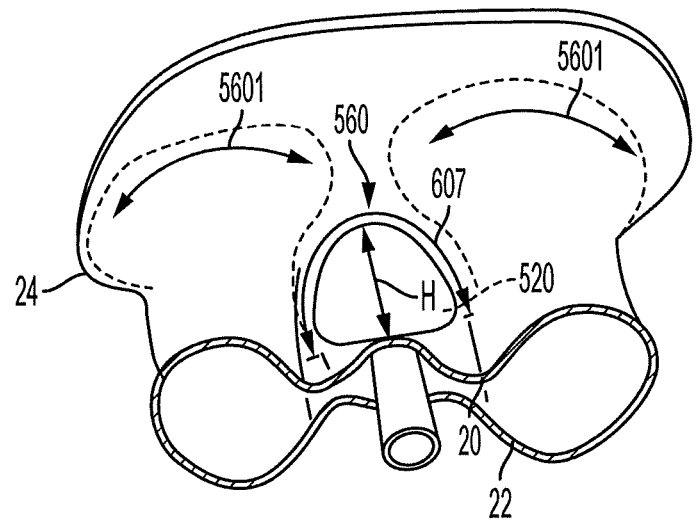

Referring now to FIGS. 56A and 56B, an Intra-Commissural view of a native mitral valve and exemplary embodiments of an implantable prosthetic device are illustrated. The shapes and size of the paddles and the coaption element affect the reduction of stress on the leaflets due to the coaption. To both coapt the valve leaflets 20, 22 against the coaption element 510 and reduce the stress applied to the valve leaflets 20, 22 by the coaption element 510 and/or the outer and inner paddles 520, 522 (inner paddles 522 not visible), the coaption element 510 can have a round or rounded shape. The round shape of the coaption element and/or the illustrated fully rounded shape of each paddle will distribute the stresses on the leaflets 20, 22 across a large, curved engagement area 607. For example, in FIG. 56A, the force on the leaflets 20, 22 by the paddles is spread along the entire rounded length of the paddles, as the leaflets 20 try to open during the diastole cycle.

Referring now to FIG. 56B, another exemplary embodiment of an implantable prosthetic device implanted on a mitral valve, shown from an Intra-Commissural view, is illustrated. The embodiment of FIG. 56B can have outer paddles 520 and inner paddles (not visible in the perspective view of FIGS. 56A and 56B) with a smaller surface area than in FIG. 56A. For example, the height H of the paddles can be less than 75% of the length (from end to annulus) of the native valve leaflets 20, 22, such as less than 50% of the length of the native valve leaflets, such as less than 25% of the length of the native valve leaflets. Further, the coaption element 510 can be smaller than the paddle as illustrated in FIG. 56A. For example, the width (across the native valve leaflet) of the coaption element can be less than 75% of the width (also across the native valve leaflet) of the coaption element, for example, the width of the coaption element can be less than 50% of the width of the paddles, for example, the width of the coaption element can be less than 25% of the width of the paddles. The smaller profiles of the paddles and the coaption element affect the force on the leaflets during the cardiac cycle. The reduction in the engagement area 607 of the paddles and the coaption element on the leaflets permits larger openings between the leaflets during diastole, especially toward the native valve annulus, and therefore increases the effective orifice area as well as leaflet mobility. This is illustrated by arrows 5601 which indicates a broader opening between the leaflets near the valve annulus 24.

Figure 57A:
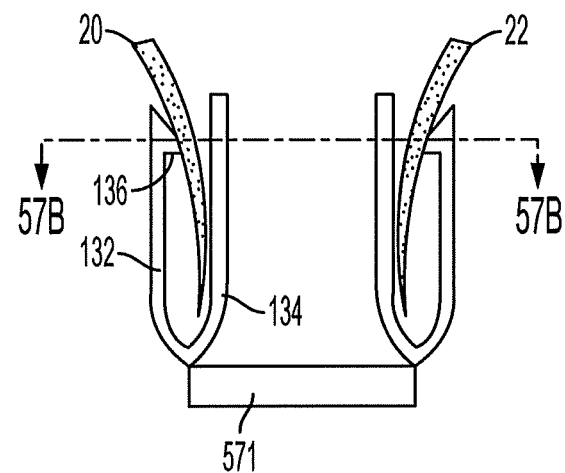
FIG. 57A shows a schematic of an exemplary embodiment of an implantable valve repair device with clasps in a closed position.

Referring now to FIGS. 57A-58B, schematics of an exemplary implantable prosthetic device are illustrated. The schematics in FIG. 57A-58B can be applied to any of the exemplary embodiments described herein. FIGS. 57A and 58A illustrate a cross-section taken from the center of an implantable prosthetic device. In FIG. 57A, leaflets 20, 22 are each held in place between an inner clasp 134 and an outer clasp 132. FIG. 57A illustrates barbs 136 on the outer clasps. Barbs are optional and can be positioned on one or more of the outer clasp or the inner clasp. Barbs on the outer clasp 132 connect to the ventricular side of the leaflets 20, 22. Barbs on the inner clasp 134 (not illustrated) connect to the atrial side of the leaflets 20, 22. The barbs can be on the inner clasp 134 in any of the embodiments described herein, including the embodiments illustrated in FIGS. 59A-61D. The clasps are held together by a base 571, which can be a cap such as cap 114 illustrated in FIG. 11, for example.

Figure 57B:
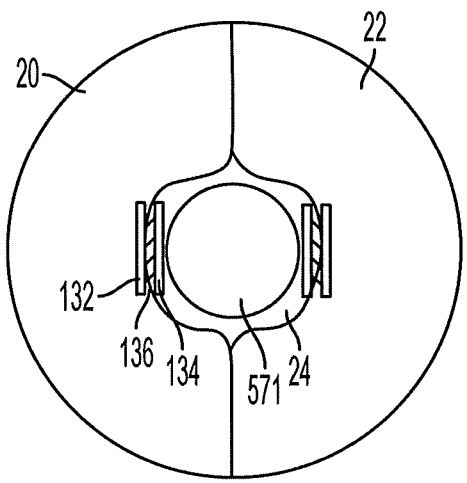
FIG. 57B shows a cross-section of the schematic of FIG. 57A taken along line 57B-57B.

FIG. 57B illustrates a cross-section of the schematic in FIG. 57A, taken along line 57B-57B, from an atrial view looking downward. In FIG. 57B, the leaflets are closed, and therefore coapted together. The central region of each leaflet is captured between an inner clasp 134 and outer clasp 132, and further fixed in position by barbs 136. The leaflets 20, 22 surround the base 571, such that the base will substantially block regurgitant blood flow during ventricular systole.

Figure 58A:
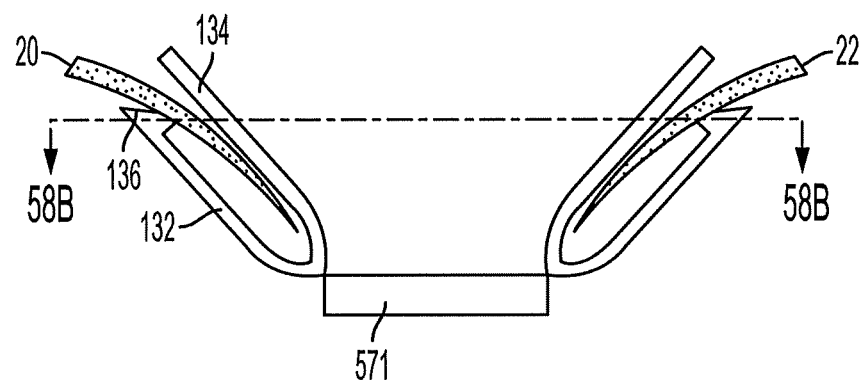
FIG. 58A shows a schematic of an exemplary embodiment of an implantable valve repair device with clasps in an open position.

FIG. 58A shows a schematic illustration of an exemplary embodiment of FIG. 57A where the clasps 132, 134 of the implantable prosthetic device 100 have pivoted to a partially open position with the movement of the native valve leaflets, while maintaining their grip on the native valve leaflets. FIG. 58A is taken from a cross-section view through the middle of the device. Leaflets 20, 22 are each captured and held between inner clasps 134 and outer clasps 132.

Figure 58B:
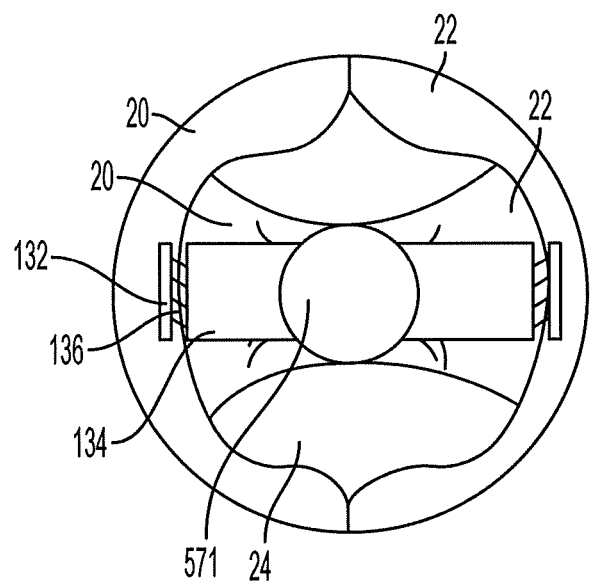
FIG. 58B shows a cross-section of the schematic of FIG. 58A taken along line 58B-58B.

FIG. 58B illustrates a cross-section of the schematic in FIG. 58A, taken along line 58B-58B, from an atrial view looking downward. The leaflets are open, as occurs during ventricular diastole, and the leaflets are connected to the base 571 along the same width of leaflet tissue that is captured in the clasps. When the native valve is open, the blood flows through the openings of the native valve on each side of the base 571.

Figure 59A:
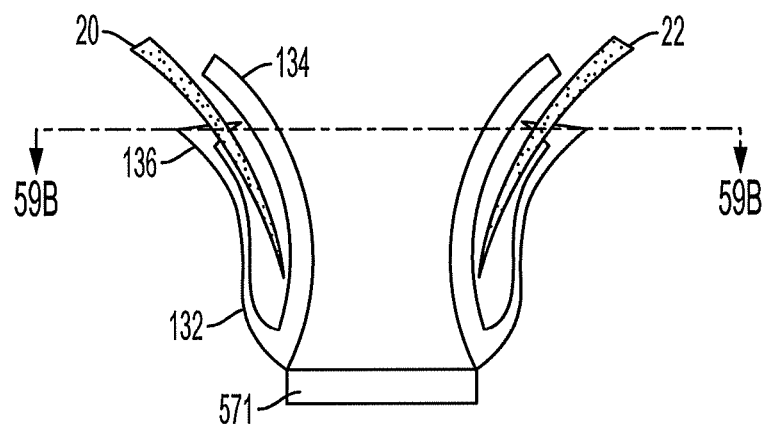
FIG. 59A shows a schematic of an exemplary embodiment of an implantable valve repair device having flexible clasps in an open position.
Figure 59B:
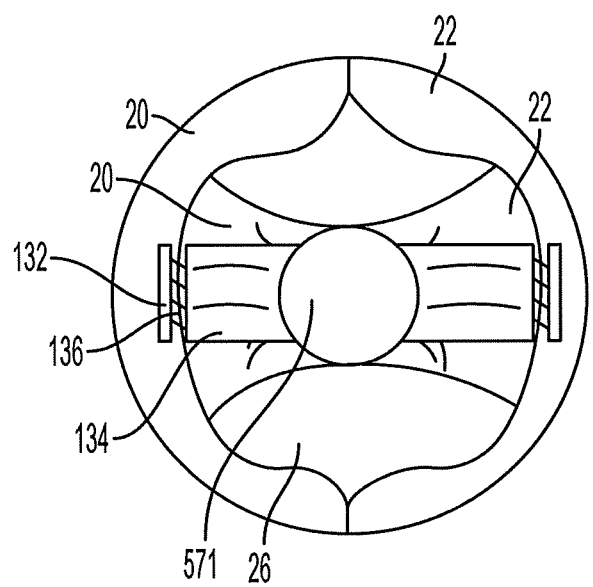
FIG. 59B shows a cross-section of the schematic of FIG. 59A taken along line 59B-59B.

Referring now to FIGS. 59A and 59B, a schematic of an exemplary embodiment of an implantable prosthetic device having flexible clasps is shown. In FIG. 59A, the leaflets 20, 22 are held in place between an inner clasp 134 and an outer clasp 132. Barbs 136 as described according to other exemplary embodiments herein are optional. The clasps are connected to a base 571. This embodiment has a closed clasp position and a partially flexed open clasp position. In the closed clasp position, the clasps and leaflets are positioned as in the schematics of FIG. 57A (and FIG. 57B). FIGS. 59A and 59B show the partially flexed open clasp position and the open position leaflets. In this figure, the clasps can be made of a flexible material. For example, nitinol can be used, with a shape set in the closed configuration, but are flexible enough to flex to the closed position during the cardiac cycle. The flexible clasps (and/or flexible paddles) can be used in place of clasps and paddles that pivoting about joints. Flexibility can also be added by forming the paddles and/or clasps out of a Nitinol braid structure, and/or by laser cutting openings in the paddles and/or clasps.

FIG. 59B illustrates a cross-section of the schematic in FIG. 59A, taken along line 59B-59B and looking down from an atrial point of view. In this open position, the leaflets are open, as occurs during ventricular diastole. The central region edges of the leaflets are approximated toward the base 571 and held in place by the clasps while the rest of the leaflet tissue opens and closes during the cardiac cycle.

Here, open leaflets permit blood flow from the left atrium to the left ventricle. In FIGS. 59A and 59B, the leaflets are open as in ventricular diastole. The leaflets can be approximated to the base in the open configuration, and still permit an effective orifice area sufficient to maintain a low pressure gradient. In an embodiment with a coaption element, the leaflets can be approximated to the coaption element. As illustrated in FIG. 59B, the leaflets are held between the clasps 134, 132 in a central region of each leaflet, and the leaflets are open in regions where they are not held by the clasps. The open leaflets permit blood to flow from the left atrium to the left ventricle. The effective orifice area in this embodiment, as with the other exemplary embodiments described herein, maintains a low pressure gradient between the left atrium and the left ventricle, of less than or equal to 5 mm Hg. In certain exemplary embodiments, there can be a coaption element, in which case the leaflets can be approximated to the coaption element (such as shown in FIGS. 47A and 47B for example). In still other exemplary embodiments, there can be paddles, and/or biasing components. Each combination of features described herein can be used in a flexible clasp embodiment, where one or more of the components are flexible and permit the clasp to move to the partially flexed open position and close instead of relying on joints to move the clasps to a partially open position and a closed position.

Figure 60A:
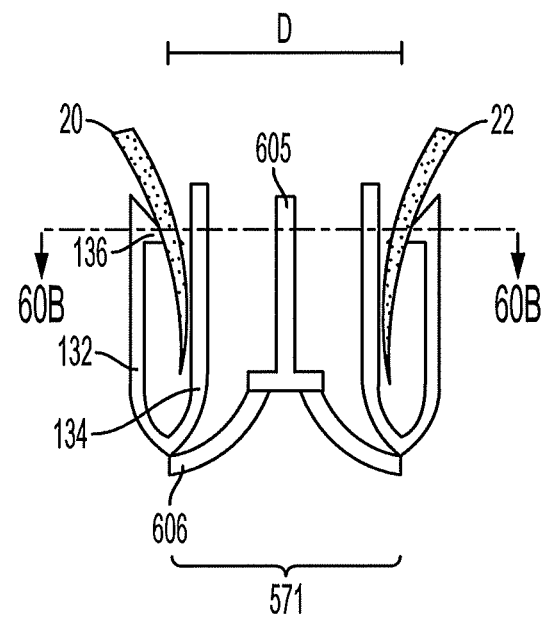
FIG. 60A shows a schematic of an exemplary embodiment of an implantable valve repair device having a center shaft for expanding the distance between clasps, where the device is unexpanded and in a closed position and the leaflets are closed.

Referring now to FIGS. 60A-61B, schematics of an exemplary embodiment are illustrated in which an actuation shaft 605 is used to adjust the distance D between each pair of clasps, where a pair of clasps includes an inner clasp 134 and an outer clasp 132. The actuation shaft 605 can be a shaft, or a wire, or any other actuating means known in the art. The actuation shaft 605 is connected to a base 571, which can have arms 606. The base can be an adjustable base and can be made of a flexible material. In FIG. 60A, the actuation shaft 605 has not yet been actuated, and the clasps and base arms 606 are in a compact position where the distance D has not yet been expanded. The leaflets 20, 22 are held in place between inner and outer clasps, 134, 132 respectively, with optional barbs 136 further holding the leaflet tissue in place between each inner and outer clasp.

Figure 60B:
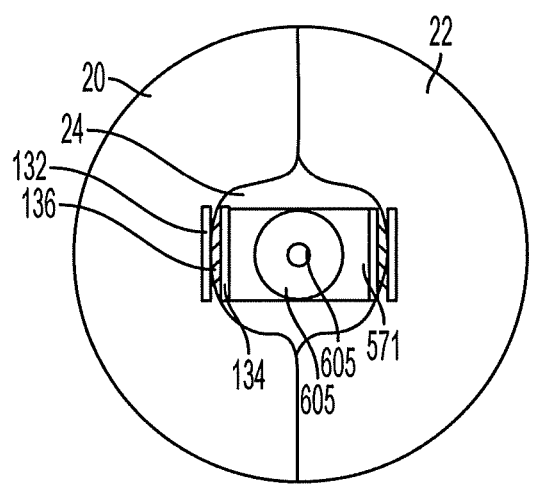
FIG. 60B shows a cross-section of the schematic of FIG. 60B taken along line 60B-60B.

FIG. 60B illustrates a top-down cross-section view taken from line 60B-60B in FIG. 60A. The shaft 605 is connected to a base 571 which has extendable arms 606. The arms 606 can be in a flexed position when the device is in a compact position, as in FIGS. 60A and 60B. In FIG. 60B, the leaflets are in a closed position.

Figure 61A:
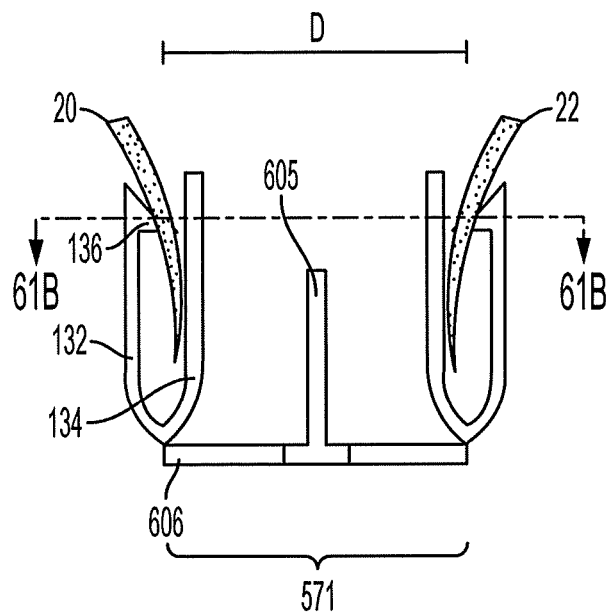
FIG. 61A shows a schematic of an exemplary embodiment of an implantable valve repair device having a center shaft for expanding the distance between clasps, where the device is expanded and in a closed position, and the leaflets are closed.
Figure 61B:
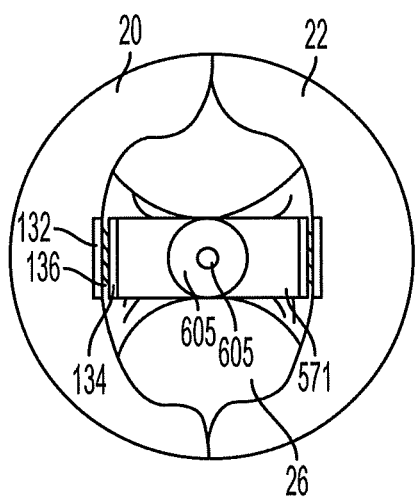
FIG. 61B shows a cross-section of the schematic of FIG. 61A taken along line 61B-61B.

Referring to FIGS. 61A and 61B, an expanded position of the exemplary embodiment is shown. The actuation shaft 605 has been actuated to expand the distance between each pair of clasps. In the expanded position, the extendable arms 606 are straightened from the curved configuration in the compact position of FIG. 60A. FIG. 61B illustrates a top-down cross-section view of the schematic shown in FIG. 61A, taken along line 61B-61B. In FIG. 61B, each leaflet 20, 22 is held between an inner clasp 134 and an outer clasp 132. The central region of the leaflets can be coapted to the arms 606 of the device, held in place by the clasps and optional barbs 136. The device can remain in the expanded configuration as the leaflets open and close. In FIGS. 61A and 61B, the device is in an actuated, expanded position, in a closed position, such that the clasps and leaflets are closed.

Figure 61C:
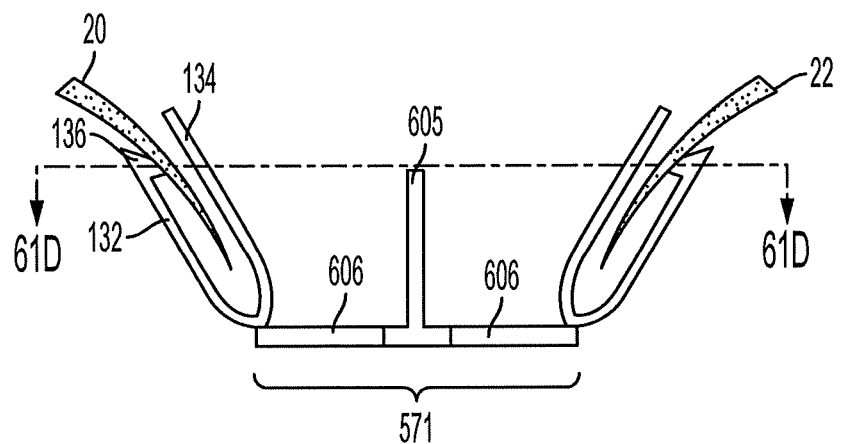
FIG. 61C shows a schematic of an exemplary embodiment of an implantable valve repair device having a center shaft for expanding the distance between clasps, where the device is expanded and in an open position, and the leaflets are open.
Figure 61D:
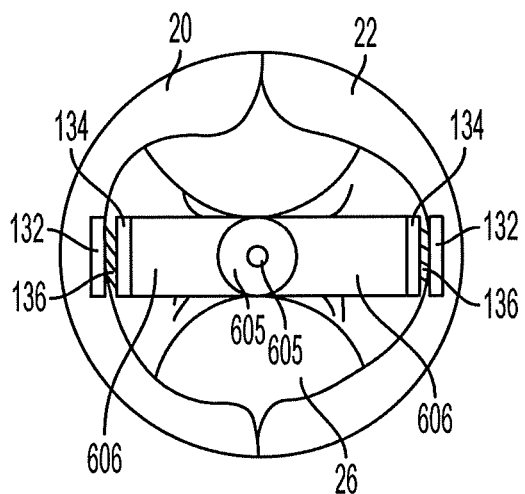
FIG. 61D shows a cross-section of the schematic of FIG. 61C taken along line 61D-61D.

Referring to FIGS. 61C and 61D, the device illustrated by FIGS. 61A and 61B is shown with the clasps expanded apart, the clasps partially pivoted (or flexed) open and the native leaflets are open, as with occur during diastole. FIG. 61C shows the clasps pivoted in a radial outward direction.

Illustrated in FIGS. 61C and 61D, the leaflets are held in place in between the inner and outer clasps. The ends of the leaflets are held in place around the base of the device, in the center region of each leaflet, shown in FIG. 61D. The sides of the leaflets are open in this illustration. The adjustability of this device permits the opening between the leaflets during diastole to be adjusted. This can accommodate different size heart valves and gaps between native leaflets that cause regurgitation. This size adjustment can also be used to optimize the effective orifice area to result in a low pressure gradient after the device is fully implanted.

Figure 62:
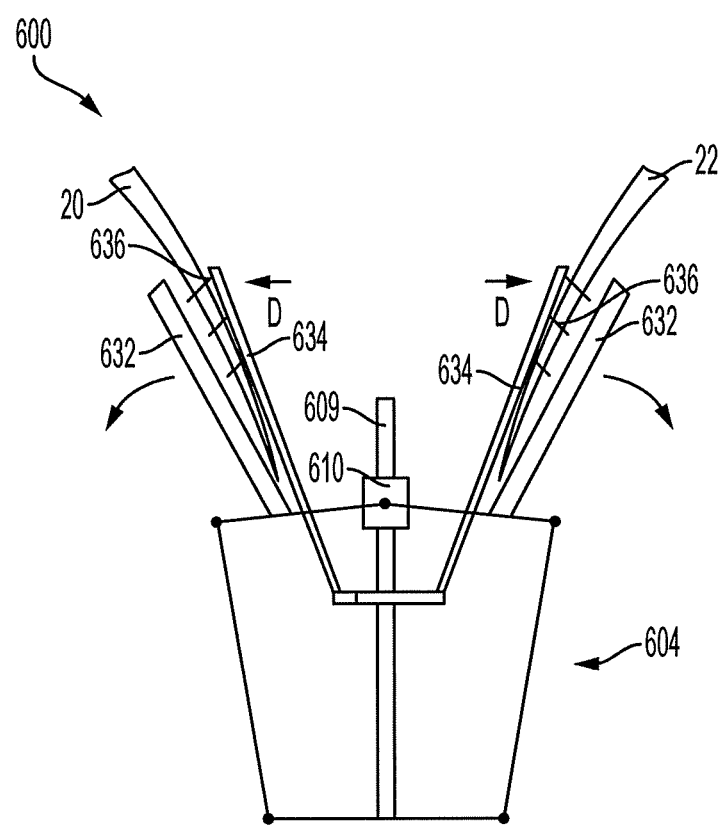
FIG. 62 shows a valve repair device in an open position.
Figure 63:
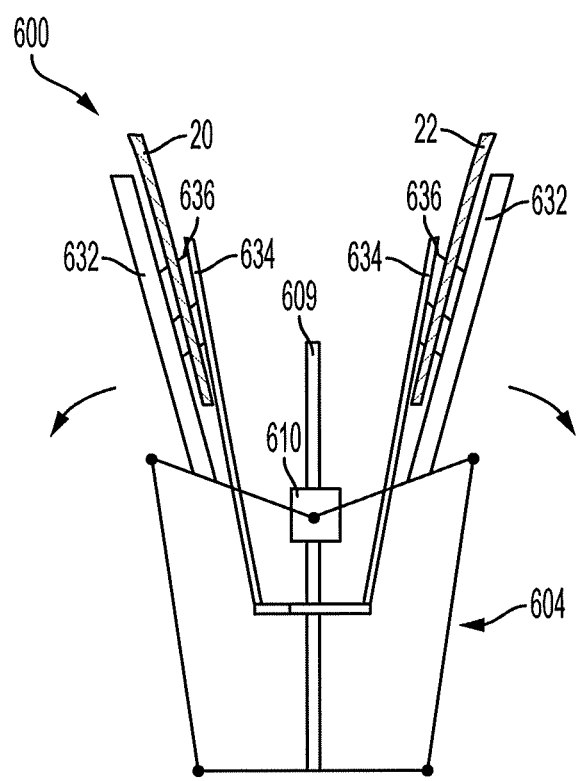
FIG. 63 shows the valve repair device of FIG. 62 in a closed position.

The inventions disclosed herein can be embodied on a wide variety of different valve repair devices. Referring now to FIGS. 62 and 63, an exemplary embodiment of a device 600 operable by a coupler to adjust the distance between the clasps is illustrated, having inner clasps 634, paddles 632, and a coupler 610, such as that described in U.S. application Ser. No. 15/868,890, filed on Jan. 9, 2018, which is incorporated by reference in its entirety herein.

Referring to FIG. 62, the device can have a shaft 609, and a coupler 610 configured to move along the shaft. The coupler 610 is mechanically connected to the paddles 632, such that movement of the coupler 610 along the shaft 609 causes the paddles to move between an open position and a closed position. In this way, the coupler 610 serves as a means for mechanically coupling the outer clasps 632 to the shaft 609 and, when moving along the shaft 609, for causing the outer clasps 632 to move between their open and closed positions. In one exemplary embodiment, the coupler is free to slide up and down on the shaft, allowing the paddles 632 and clasps to move closer together (See FIG. 63) and farther apart (See FIG. 62) with the beating of the heart.

In certain embodiments, the paddles 634 are connected to the base assembly 604, such that the inner clasps can be moved to adjust the width of the opening 614 between the outer paddles 632 and the inner clasps 634. Inner clasps 634 can also have barbed portions 636 on a region thereon, to improve attachment to the leaflets 20, 22. Such a device can be used to grasp leaflet tissue as in the other exemplary embodiments described herein, and can remain open once implanted, or the clasps can open and close with the cardiac cycle.

Referring now to FIG. 63, the coupler 610 has been moved to bring the clasps closer toward the center of the device. The coupler can be fixed in a position as shown In FIG. 62, or it can move between the "partially open device" position in FIG. 62 and the "closed device" position illustrated in FIG. 63 to open and close the clasps of the device with the cardiac cycle as in other exemplary embodiments described herein.

Figure 64:
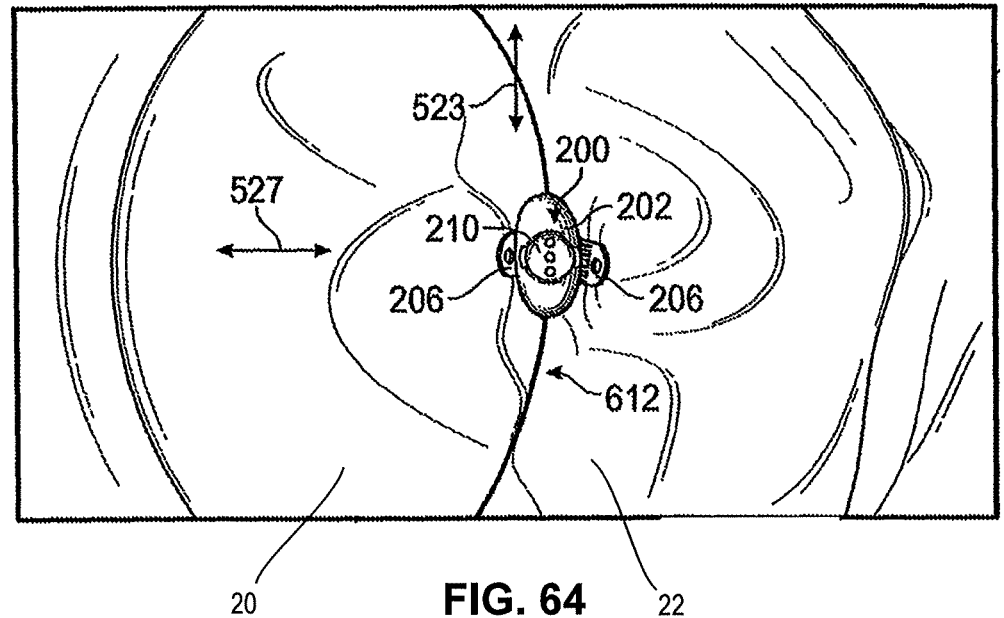
FIG. 64 shows a valve repair device according to an exemplary embodiment implanted in a native valve when closed.
Figure 65:
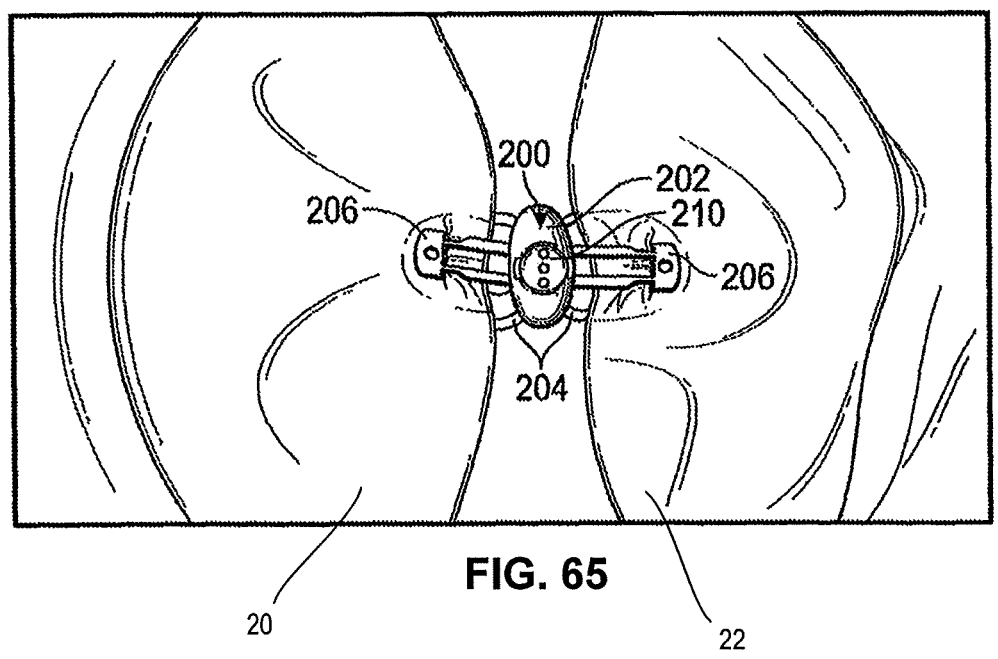
FIG. 65 shows the valve repair device of FIG. 64 when a native valve is open.

Referring now to FIGS. 64 and 65, an exemplary embodiment of a device having anchors 204 and a spacer member 202 is illustrated, such as that described in U.S. provisional application Ser. No. 62/659,253, incorporated by reference in its entirety herein. The illustrations in FIGS. 64 and 65 are taken from a bottom point of view taken from within a ventricle, when the device 200 is implanted on the leaflets of a mitral valve. In this embodiment, the anchors 204 can move radially outwardly relative to the spacer member 202 to a partially open configuration during ventricular diastole such that the native mitral valve has a single orifice, as shown in FIG. 65. The anchors 204 can move radially inwardly relative to the spacer member 202 to a closed configuration during ventricular systole such that the native leaflets 608 coapt together and/or against the prosthetic device 200 to prevent or reduce mitral regurgitation, as shown in FIG. 64. As the anchors 204 open and close during the natural cardiac cycles, the clasps 206 can retain the native leaflets 20, 22 against the anchors 204, as shown in FIGS. 64-65.

Configuring the prosthetic device 200 in this manner allows the native leaflets 20, 22 to move naturally upon implantation. This can, for example, promote antegrade blood flow during ventricular diastole, while still reducing or preventing retrograde blood flow during ventricular systole. It can also reduce or prevent native tissue damage to the native leaflets. Over time, endothelialization can form a tissue bridge between the anchoring paddles and the spacer member.

While various inventive aspects, concepts and features of the disclosures may be described and illustrated herein as embodied in combination in the exemplary embodiments, these various aspects, concepts, and features may be used in many alternative embodiments, either individually or in various combinations and sub-combinations thereof. Unless expressly excluded herein all such combinations and sub-combinations are intended to be within the scope of the present application. Still further, while various alternative embodiments as to the various aspects, concepts, and features of the disclosures—such as alternative materials, structures, configurations, methods, devices, and components, alternatives as to form, fit, and function, and so on—may be described herein, such descriptions are not intended to be a complete or exhaustive list of available alternative embodiments, whether presently known or later developed. Those skilled in the art may readily adopt one or more of the inventive aspects, concepts, or features into additional embodiments and uses within the scope of the present application even if such embodiments are not expressly disclosed herein.

Additionally, even though some features, concepts, or aspects of the disclosures may be described herein as being a preferred arrangement or method, such description is not intended to suggest that such feature is required or necessary unless expressly so stated. Still further, exemplary or representative values and ranges may be included to assist in understanding the present application, however, such values and ranges are not to be construed in a limiting sense and are intended to be critical values or ranges only if so expressly stated.

Moreover, while various aspects, features and concepts may be expressly identified herein as being inventive or forming part of a disclosure, such identification is not intended to be exclusive, but rather there may be inventive aspects, concepts, and features that are fully described herein without being expressly identified as such or as part of a specific disclosure, the disclosures instead being set forth in the appended claims. Descriptions of exemplary methods or processes are not limited to inclusion of all steps as being required in all cases, nor is the order that the steps are presented to be construed as required or necessary unless expressly so stated. The words used in the claims have their full ordinary meanings and are not limited in any way by the description of the embodiments in the specification.

What is claimed is:

1. A valve repair device for repairing a native heart valve of a patient, the valve repair device comprising:
    a pair of clasps, wherein each clasp is configured to attach to a native valve leaflet;
    wherein ends of the pair of clasps are configured to move away from one another to a partially open position when the native valve leaflets open during a diastolic phase of a cardiac cycle; and
    wherein ends of the pair of clasps are configured to move toward one another when the native valve leaflets close during a ventricular systole of the cardiac cycle; and
    a pair of paddles, wherein each clasp is fixed to one of the paddles.

2. The device of claim 1, wherein the ends of the clasps are angled away from one another when the clasps are in the partially open position.

3. The device of claim 1, wherein the paddles move toward and away from one another during the cardiac cycle to move the ends of the clasps toward and away from one another during the cardiac cycle.

4. The valve repair device of claim 1, further comprising a coaption element connected to the pair of clasps, wherein the movement of the clasps causes the native valve leaflets to coapt against the coaption element when the native valve closes and causes the native valve leaflets to separate from the coaption element when the native valve opens.

5. The valve repair device of claim 1 wherein the device further comprises a pair of biasing members, wherein the biasing members bias the paddles toward one another.

6. A valve repair device for repairing a native valve of a patient, the valve repair device comprising:
    a pair of paddles; and
    a pair of clasps, wherein each pair of clasps comprises an inner clasp member, an outer clasp member, and an end,
    wherein the inner clasp member of each clasp is connected to one of the paddles;
    wherein each clasp is configured to attach to a leaflet of the native valve;
    wherein the paddles and connected clasps are moveable between a closed position and an open position;
    wherein the paddles are configured to be implanted on the native valve leaflets in a partially open position; and
    wherein the paddles are configured to further open from the partially open position when a force is applied to the clasps by the leaflets opening during diastole.

7. The valve repair device of claim 6, further comprising a coaption element connected to the pair of paddles, wherein the movement of the paddles and clasps causes the native valve leaflets to coapt against the coaption element when the native valve closes and causes the native valve leaflets to separate from the coaption element when the native valve opens.

8. The valve repair device of claim 6 wherein the device further comprises a pair of biasing members, wherein the biasing members bias the paddles toward one another.

9. A valve repair device for repairing a native heart valve of a patient, the valve repair device comprising:
    a pair of flexible clasps, wherein each clasp is configured to attach to a native valve leaflet;
    wherein the clasps are configured to flex such that ends of the pair of clasps move away from one another to a partially open position when the native valve leaflets open during a diastolic phase of a cardiac cycle;
    wherein the clasps are configured to flex such that ends of the pair of clasps move toward one another when the native valve leaflets close during a ventricular systole of the cardiac cycle; and
    wherein the device further comprises a pair of biasing members, wherein the biasing members bias the clasps toward one another.

10. The device of claim 9, wherein the ends of the clasps are angled away from one another when the clasps are in the partially open position.

11. The valve repair device of claim 9, further comprising a coaption element connected to the pair of clasps, wherein the movement of the clasps causes the native valve leaflets to coapt against the coaption element when the native valve closes and causes the native valve leaflets to separate from the coaption element when the native valve opens.

12. A valve repair device for repairing a native heart valve of a patient, the valve repair device comprising:
- a pair of clasps, wherein each clasp is configured to attach to a native valve leaflet;
- wherein ends of the pair of clasps are configured to move away from one another to a partially open position when the native valve leaflets open during a diastolic phase of a cardiac cycle;
- wherein ends of the pair of clasps are configured to move toward one another when the native valve leaflets close during a ventricular systole of the cardiac cycle; and
- wherein the device further comprises a pair of biasing members, wherein the biasing members bias the clasps toward one another.

13. A valve repair device for repairing a native valve of a patient, the valve repair device comprising:
- a pair of paddles; and
- a pair of clasps, wherein each pair of clasps comprises an inner clasp member, an outer clasp member, and an end;
- wherein the inner clasp member of each clasp is connected to one of the paddles;
- wherein each clasp is configured to attach to a leaflet of the native valve;
- wherein the paddles and connected clasps are moveable between a closed position and an open position;
- wherein the paddles are configured to be implanted on the native valve leaflets in a partially open position; and
- wherein the paddles are configured to further open from the partially open position when a force is applied to the clasps by the leaflets opening during diastole and wherein the paddles are configured to return to the partially open position when a force is applied to the clasps by the leaflets closing during systole.

* * * * *